United States Patent
Vogt et al.

(10) Patent No.: US 7,039,997 B2
(45) Date of Patent: May 9, 2006

(54) APPARATUS AND METHOD FOR SECURING ENGAGEMENT BETWEEN FASTENING COMPONENTS OF PRE-FASTENED GARMENTS

(75) Inventors: Brian Robert Vogt, Oshkosh, WI (US); Jason Gene Csida, Reno, TX (US); Michael Lee Lohoff, Oshkosh, WI (US); Charles Robert Tomsovic, Omro, WI (US); Wade L. Behnke, Little Chute, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 571 days.

(21) Appl. No.: 10/158,443

(22) Filed: May 30, 2002

(65) Prior Publication Data
US 2003/0225390 A1 Dec. 4, 2003

(51) Int. Cl.
*B23P 11/02* (2006.01)
*B25B 27/14* (2006.01)
*D02G 1/12* (2006.01)
*A61F 13/15* (2006.01)

(52) U.S. Cl. .................... 29/449; 29/281.5; 28/269; 604/391

(58) Field of Classification Search .............. 29/429, 29/428, 449, 450, 335, 700, 281.5; 28/269; 604/391, 385.1, 386, 390; 26/78; 156/163, 156/164
See application file for complete search history.

(56) References Cited

U.S. PATENT DOCUMENTS 2,957,512 A 10/1960 Wade et al.
3,319,307 A 5/1967 Marforio
3,577,607 A 5/1971 Ikoma et al.
3,694,867 A 10/1972 Stumpf
3,800,796 A 4/1974 Jacob (Continued)

FOREIGN PATENT DOCUMENTS

| EP | 0 217 032 A2 | 7/1986 |
|---|---|---|
| EP | 0 463 276 A1 | 1/1992 |
| EP | 0 638 304 B1 | 2/1995 |
| EP | 0 800 379 B1 | 10/1997 |
| EP | 0812584 A2 | 12/1997 |

(Continued)

OTHER PUBLICATIONS

International Search Report for PCT/US 02/40780 dated Apr. 22, 2003.
International Search Report for PCT/US 03/11793 dated Sep. 1, 2003.

*Primary Examiner*—John C. Hong
(74) *Attorney, Agent, or Firm*—Senniger Powers

(57) ABSTRACT

In a method and apparatus for securing engagement between fastening components of a pre-fastened garment the fastening components are aligned in at least partially overlapping relationship with each other and engaged with each other to define an engagement seam. The fastening components are then flexed at the engagement seam to generate a shear stress at the seam to thereby promote increased engagement between the fastening components. In another embodiment, the fastening components are delivered in a predetermined direction to a nip and then drawn into the nip at a speed greater than the speed at which the fastening components are delivered to the nip. The fastening components are passed through the nip generally to squeeze the fastening components together at the engagement seam for promoting enhanced engagement between the fastening components.

53 Claims, 27 Drawing Sheets

U.S. PATENT DOCUMENTS

| | | |
|---|---|---|
| 3,943,981 A | 3/1976 | DeBrabander |
| 4,051,853 A | 10/1977 | Egan, Jr. |
| 4,145,763 A | 3/1979 | Abrams et al. |
| 4,205,679 A | 6/1980 | Repke et al. |
| 4,402,690 A | 9/1983 | Redfern |
| 4,543,141 A | 9/1985 | Bradley et al. |
| 4,606,964 A | 8/1986 | Wideman |
| 4,610,680 A | 9/1986 | LaFleur |
| 4,615,695 A | 10/1986 | Cooper |
| 4,657,802 A | 4/1987 | Morman |
| 4,663,220 A | 5/1987 | Wisneski et al. |
| 4,699,622 A | 10/1987 | Toussant et al. |
| 4,704,116 A | 11/1987 | Enloe |
| 4,705,710 A | 11/1987 | Matsuda |
| 4,714,096 A | 12/1987 | Guay |
| 4,739,635 A | 4/1988 | Conley et al. |
| 4,761,318 A | 8/1988 | Ott et al. |
| 4,826,499 A | 5/1989 | Ahr |
| 4,834,742 A | 5/1989 | Wilson et al. |
| 4,834,820 A | 5/1989 | Kondo et al. |
| 4,847,134 A | 7/1989 | Fahrenkrug et al. |
| 4,850,990 A | 7/1989 | Huntoon et al. |
| 4,894,060 A | 1/1990 | Nestegard |
| 4,900,384 A | 2/1990 | Sanders et al. |
| 4,936,840 A | 6/1990 | Proxmire |
| 4,940,464 A | 7/1990 | Van Gompel et al. |
| 4,963,140 A | 10/1990 | Robertson et al. |
| 5,019,073 A | 5/1991 | Roessler et al. |
| 5,032,122 A | 7/1991 | Noel et al. |
| 5,046,272 A | 9/1991 | Vogt et al. |
| 5,087,253 A | 2/1992 | Cooper |
| 5,104,116 A | 4/1992 | Pohjola |
| 5,110,403 A | 5/1992 | Ehlert et al. |
| 5,116,662 A | 5/1992 | Morman |
| 5,176,670 A | 1/1993 | Roessler et al. |
| 5,176,671 A | 1/1993 | Roessler et al. |
| 5,224,405 A | 7/1993 | Pohjola |
| 5,226,992 A | 7/1993 | Morman |
| 5,246,433 A | 9/1993 | Hasse et al. |
| 5,256,231 A | 10/1993 | Gorman et al. |
| 5,286,543 A | 2/1994 | Ungpiyakul et al. |
| 5,318,555 A | 6/1994 | Siebers et al. |
| 5,326,612 A | 7/1994 | Goulait |
| 5,359,525 A | 10/1994 | Weyenberg |
| 5,370,634 A | 12/1994 | Ando et al. |
| 5,380,313 A | 1/1995 | Goulait |
| 5,386,595 A | 2/1995 | Kuen et al. |
| 5,407,439 A | 4/1995 | Goulait |
| 5,500,063 A | 3/1996 | Jessup |
| 5,547,531 A | 8/1996 | Allen et al. |
| 5,552,007 A | 9/1996 | Rajala et al. |
| 5,586,371 A | 12/1996 | Thomas |
| 5,595,567 A | 1/1997 | King et al. |
| 5,615,460 A | 4/1997 | Weirich et al. |
| 5,616,394 A | 4/1997 | Gorman et al. |
| 5,624,427 A | 4/1997 | Bergman et al. |
| 5,626,711 A | 5/1997 | Herrmann |
| 5,647,864 A | 7/1997 | Allen et al. |
| 5,660,666 A | 8/1997 | Dilnik et al. |
| 5,669,900 A | 9/1997 | Bullwinkel et al. |
| 5,669,901 A | 9/1997 | LaFortune et al. |
| 5,681,302 A | 10/1997 | Melbye et al. |
| 5,693,401 A | 12/1997 | Sommers et al. |
| 5,699,593 A | 12/1997 | Jackson |
| 5,707,707 A | 1/1998 | Burnes et al. |
| 5,735,840 A | 4/1998 | Kline et al. |
| 5,755,902 A | 5/1998 | Reynolds |
| 5,763,041 A | 6/1998 | Leak et al. |
| 5,766,389 A | 6/1998 | Brandon et al. |
| 5,772,825 A | 6/1998 | Schmitz |
| 5,779,831 A | 7/1998 | Schmitz |
| 5,785,699 A | 7/1998 | Schmitz |
| 5,786,062 A | 7/1998 | Callahan, Jr. et al. |
| 5,795,350 A | 8/1998 | Schmitz |
| 5,818,719 A | 10/1998 | Brandon et al. |
| 5,830,206 A | 11/1998 | Larsson |
| 5,830,298 A | 11/1998 | Jackson |
| 5,855,574 A | 1/1999 | Kling et al. |
| 5,858,515 A | 1/1999 | Stokes et al. |
| 5,879,500 A | 3/1999 | Herrin et al. |
| 5,888,607 A | 3/1999 | Seth et al. |
| 5,891,547 A | 4/1999 | Lawless |
| 5,897,545 A | 4/1999 | Kline et al. |
| 5,897,547 A | 4/1999 | Schmitz |
| 5,901,419 A | 5/1999 | Widlund et al. |
| 5,916,207 A | 6/1999 | Toyoda et al. |
| 5,953,797 A | 9/1999 | Provost et al. |
| 5,961,761 A | 10/1999 | Heindel et al. |
| 5,964,742 A | 10/1999 | McCormack et al. |
| 5,997,981 A | 12/1999 | McCormack et al. |
| 6,018,852 A | 2/2000 | Coslovi et al. |
| 6,027,485 A | 2/2000 | Matsushita et al. |
| 6,036,805 A | 3/2000 | McNichols |
| 6,086,571 A | 7/2000 | Guevara et al. |
| 6,102,901 A | 8/2000 | Lord et al. |
| 6,113,717 A | 9/2000 | Vogt et al. |
| 6,136,405 A | 10/2000 | Young et al. |
| 6,146,738 A | 11/2000 | Tsuji et al. |
| 6,192,556 B1 | 2/2001 | Kikko et al. |
| 6,210,389 B1 | 4/2001 | Long et al. |
| 6,287,287 B1 | 9/2001 | Elsberg |
| 6,328,725 B1 | 12/2001 | Fernfors |
| 6,329,016 B1 | 12/2001 | Shepard et al. |
| 6,332,250 B1 | 12/2001 | Igaue et al. |
| 6,395,115 B1 | 5/2002 | Popp et al. |
| 6,409,858 B1 | 6/2002 | Popp et al. |
| 6,432,243 B1 | 8/2002 | Popp et al. |
| 6,432,248 B1 | 8/2002 | Popp et al. |
| 6,443,937 B1 | 9/2002 | Matsushita |
| 6,447,628 B1 | 9/2002 | Couillard et al. |
| 6,458,115 B1 | 10/2002 | Lindqvist et al. |
| 6,461,344 B1 | 10/2002 | Widlund et al. |
| 6,481,362 B1 | 11/2002 | Hietpas et al. |
| 6,497,032 B1 | 12/2002 | Maxton et al. |
| 6,513,221 B1 | 2/2003 | Vogt et al. |
| 6,514,187 B1 | 2/2003 | Coenen et al. |
| 2002/0002358 A1 | 1/2002 | Durrance et al. |

FOREIGN PATENT DOCUMENTS

| | | |
|---|---|---|
| EP | 0757550 B1 | 9/1998 |
| FR | 1.371.254 | 9/1964 |
| GB | 1520740 | 8/1978 |
| JP | 409191908 | 7/1997 |
| WO | WO 95/27462 A1 | 10/1995 |
| WO | WO 96/09027 A1 | 3/1996 |
| WO | WO 98/15246 | 4/1998 |
| WO | WO 99/65441 A1 | 12/1999 |
| WO | WO 00/23025 A1 | 4/2000 |
| WO | WO 00/35395 A3 | 6/2000 |
| WO | WO 00/35395 A2 | 6/2000 |
| WO | WO 00/35398 A1 | 6/2000 |
| WO | WO 00/37009 A2 | 6/2000 |
| WO | WO 01/83347 A1 | 11/2001 |
| WO | WO 01/87206 | 11/2001 |
| WO | WO 01/87208 | 11/2001 |
| WO | WO 01/87209 | 11/2001 |
| WO | WO 01/87210 A1 | 11/2001 |
| WO | WO 01/87218 A2 | 11/2001 |
| WO | WO 01/87562 | 11/2001 |
| WO | WO 01/87753 A2 | 11/2001 |

APPARATUS AND METHOD FOR SECURING ENGAGEMENT BETWEEN FASTENING COMPONENTS OF PRE-FASTENED GARMENTS

BACKGROUND OF THE INVENTION

The present invention relates generally to apparatus and methods for making pre-assembled or pre-fastened garments, and more particularly to apparatus and methods for promoting a secure engagement between fastening components of pre-fastened garments during the making of such garments.

Garments, and more particularly disposable absorbent garments, have numerous applications including diapers, training pants, feminine care products, medical garments and adult incontinence products. A typical disposable absorbent garment is formed as a composite structure including an absorbent assembly disposed between a liquid permeable bodyside liner and a liquid impermeable outer cover. These components can be combined with other materials and features such as elastic materials and containment structures to form a product which is specifically suited to its intended purposes. A number of such garments include fastening components which are intended to be secured together (e.g., pre-fastened) during manufacture of the garment so that the product is packaged in its fully assembled form.

For example, one such pre-fastened garment is a pair of children's training pants which has a central absorbent chassis and front and rear side panels extending laterally out from each side of the absorbent chassis. Each of the front and rear side panels has a fastening component thereon, such as a hook or a loop type fastener. During manufacture of the training pants, the central absorbent chassis is initially formed generally flat and then folded over so that the front and rear side panels face each other. The fastening components of the front and rear side panels on each side of the absorbent chassis are then aligned and engaged with each other to pre-fasten the training pants in its fully assembled three-dimensional form.

However, existing techniques for making conventional garments such as the training pants described above or other pre-fastened garments which engage fastening components together during manufacture are in some respects inadequate. For example, weak engagement strength between hook and loop fasteners, partial or whole separation of the fastening components during manufacture, and packaging problems resulting from poorly fastened or otherwise unfastened components are some of the shortcomings of existing pre-fastened garment making techniques. There is a need, therefore, for apparatus and methods which increase the engagement strength between fastening components while making a pre-fastened garment.

SUMMARY OF THE INVENTION

In general, a method for securing engagement between fastening components of a pre-fastened garment upon initial assembly thereof comprises arranging the fastening components in at least partially opposed relationship with each other and engaging the fastening components with each other to define an engagement seam. The fastening components are flexed at the engagement seam to generate a shear stress at the seam to thereby promote increased engagement between the fastening components.

In another embodiment, a method for securing engagement between fastening components of a pre-fastened garment upon initial assembly thereof generally comprises arranging the fastening components in at least partially opposed relationship with each other and engaging the fastening components with each other to define an engagement seam. The garment is mechanically handled to generate a shear stress along the engagement seam to promote increased engagement between the fastening components.

In yet another embodiment, a method for securing engagement between fastening components of a pre-fastened garment generally comprises aligning the fastening components in at least partially opposed relationship with each other and engaging the fastening components with each other to define an engagement seam. The fastening components are delivered to the nip at the engagement seam and then drawn into the nip at the engagement seam at a speed greater than the speed at which the fastening components are delivered to the nip. The fastening components are then passed through the nip generally at the engagement seam to urge the fastening components together for promoting increased engagement between the fastening components.

Apparatus for making a pre-fastened garment of the type comprising an absorbent chassis having a front waist region, a back waist region and a crotch region extending longitudinally therebetween, a front side panel extending laterally out from the front waist region and a back side panel extending laterally out from the back waist region generally comprises an assembly section adapted to at least partially assemble the garment such that the garment exits the assembly section with fastening components of the front and back side panels generally disconnected from each other. A seaming section is adapted to orient the front and back side panels relative to each other such that the fastening components are in at least partially opposed relationship with each other, and to engage the fastening components together to form an engagement seam of the garment. A flexing assembly of the apparatus generally flexes the fastening components at the engagement seam to generate a shear stress at said engagement seam to thereby promote increased engagement between the fastening components.

A nip assembly for securing engagement between fastening components of a pre-fastened garment generally comprises a first roller rotatable on a first rotation axis and a second roller rotatable on a second rotation axis. The second roller is in generally closely spaced relationship with the first roller transverse to a predetermined direction in which the fastening components are received by the nip assembly to define a nip therebetween through which the fastening components pass following receipt of the fastening components into the nip assembly. The rollers of the nip assembly thereby urge the fastening components together generally at the engagement seam. The second rotation axis is spaced downstream from the first rotation axis in the predetermined direction such that the nip between the first and second rollers is generally skewed relative to the predetermined direction.

BRIEF DESCRIPTION OF THE DRAWINGS

Corresponding parts are designated by corresponding reference characters and numerals throughout the several views of the drawings.

Definitions

Figure 1:
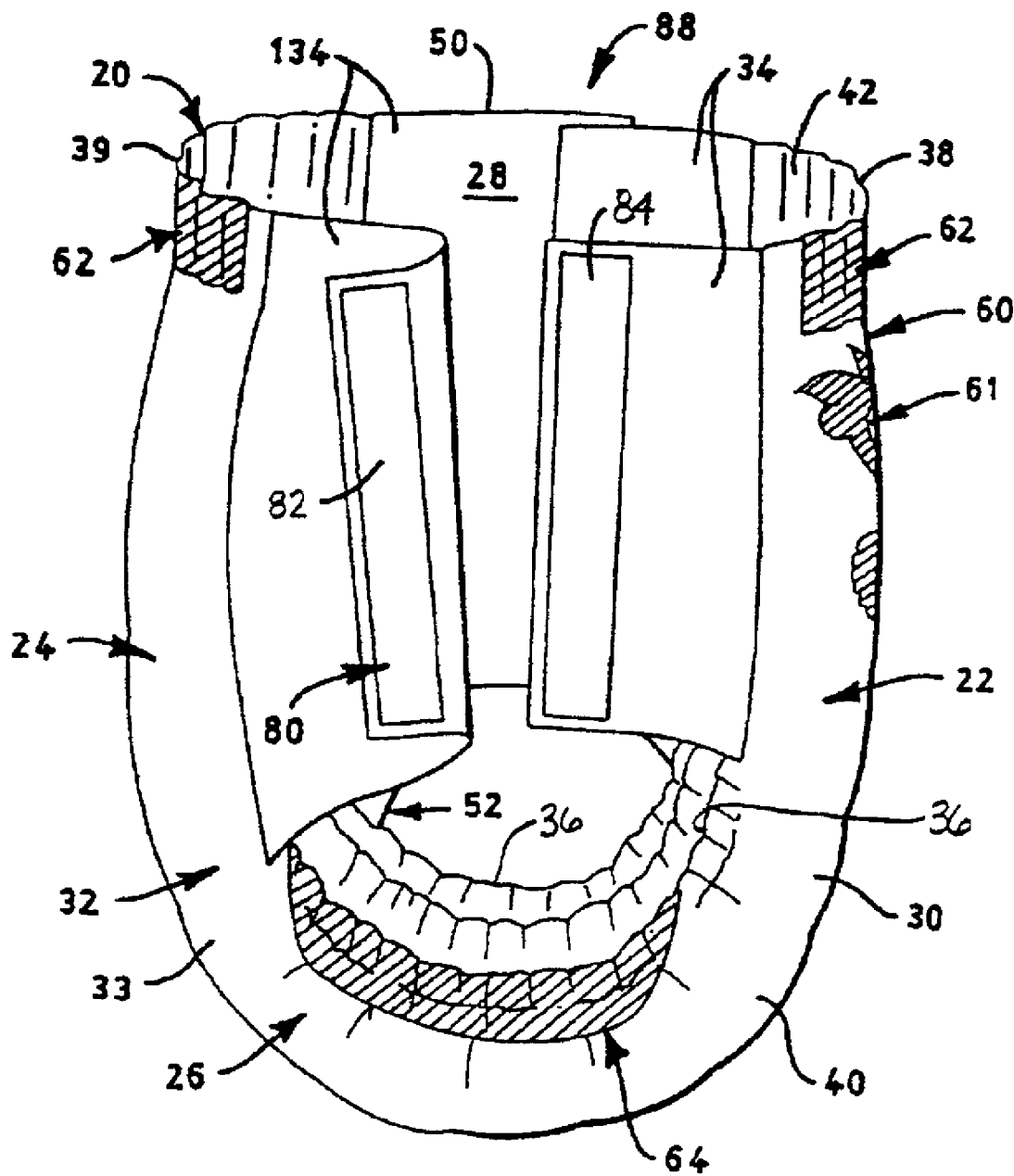
FIG. 1 is a side view of a pair of training pants with a fastening system of the training pants shown engaged on one side and connected on the other side thereof.

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed, disposed on," and variations thereof are intended to mean that one element can be integral with another element, or that one element can be a separate structure bonded to or placed with or placed near another element.

"Elastic, elasticized and elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Flexible" refers to materials which are compliant and which will readily conform to the general shape and contours of the wearer's body.

"Force" includes a physical influence exerted by one body on another which produces acceleration of bodies that are free to move and deformation of bodies that are not free to move. Force is expressed in grams per unit area.

"Graphic" refers to any design, pattern, or the like that is visible on an absorbent article.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated wettable or hydrophilic, while fibers having contact angles greater than 90° are designated non-wettable or hydrophobic.

"Integral" is used to refer to various portions of a single unitary element rather than separate structures bonded to or placed with or placed near one another.

"Inward" and "outward" refer to positions relative to the center of an absorbent article, and particularly transversely and/or longitudinally closer to or away from the longitudinal and transverse center of the absorbent article.

"Layer," when used in the singular, can have the dual meaning of a single element or a plurality of elements.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable when used herein.

"Longitudinal" and "transverse" have their customary meanings. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Member," when used in the singular, can have the dual meaning of a single element or a plurality of elements.

"Nonwoven" and "nonwoven web" refer to materials and webs of material which are formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Outer cover graphic" refers to a graphic that is directly visible upon inspection of the exterior surface of a garment, and for a refastenable garment is in reference to inspection of the exterior surface of the garment when the fastening system is engaged as it would be during use.

"Permanently bonded" refers to the joining, adhering, connecting, attaching, or the like, of two elements of an absorbent garment such that the elements tend to be and remain bonded during normal use conditions of the absorbent garment.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Rupture" means the breaking or tearing apart of a material; in tensile testing, the term refers to the total separation of a material into two parts either all at once or in stages, or the development of a hole in some materials.

"Stretch bonded" refers to an elastic member being bonded to another member while the elastic member is extended at least about 25 percent of its relaxed length. Desirably, the term stretch bonded refers to the situation wherein the elastic member is extended at least about 100 percent, and more desirably at least about 300 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

"Surface" includes any layer, film, woven, nonwoven, laminate, composite, or the like, whether pervious or impervious to air, gas, and/or liquids.

"Tension" includes a uniaxial force tending to cause the extension of a body or the balancing force within that body resisting the extension.

"Thermoplastic" describes a material that softens when exposed to heat and which substantially returns to a non-softened condition when cooled to room temperature.

These terms may be defined with additional language in the remaining portions of the specification.

DETAILED DESCRIPTION

The methods and apparatus of the present invention can be used to make a variety of garments. Examples of such garments include disposable absorbent articles such as diapers, training pants, feminine hygiene products, incontinence products, other personal care or health care garments; medical garments; swim pants; athletic clothing; pants and shorts; or the like. For ease of explanation, the methods and apparatus of the present invention are hereafter described in connection with making pre-fastened children's training pants, generally indicated in FIG. 1. In particular, the methods and apparatus will be described in terms of those for making pre-fastened disposable training pants as described in U.S. patent application Ser. No. 09/444,083 titled "Absorbent Articles With Refastenable Side Seams" and filed Nov. 22, 1999 (corresponding to PCT application WO 00/37009 published Jun. 29, 2000) by A. L. Fletcher et al., the disclosure of which is incorporated herein by reference. Training pants can also be constructed using the methods and apparatus disclosed in U.S. Pat. No. 4,940,464 issued Jul. 10, 1990 to Van Gompel et al.; and U.S. Pat. No. 5,766,389 issued Jun. 16, 1998 to Brandon et al.; the disclosures of which are also incorporated herein by reference.

With reference now to the drawings, and in particular to FIG. 1, the pair of training pants 20 is illustrated in a partially fastened condition and comprises an absorbent chassis 32 and a fastening system 80. The absorbent chassis 32 defines a front waist region 22, a back waist region 24, a crotch region 26 interconnecting the front and back waist regions, an inner surface 28 which is configured to contact the wearer, and an outer surface 30 opposite the inner surface which is configured to contact the wearer's clothing. With additional reference to FIGS. 2 and 3, the absorbent chassis 32 also defines a pair of transversely opposed side edges 36 and a pair of longitudinally opposed waist edges, which are designated front waist edge 38 and back waist edge 39. The front waist region 22 is contiguous with the front waist edge 38, and the back waist region 24 is contiguous with the back waist edge 39.

Figure 2:
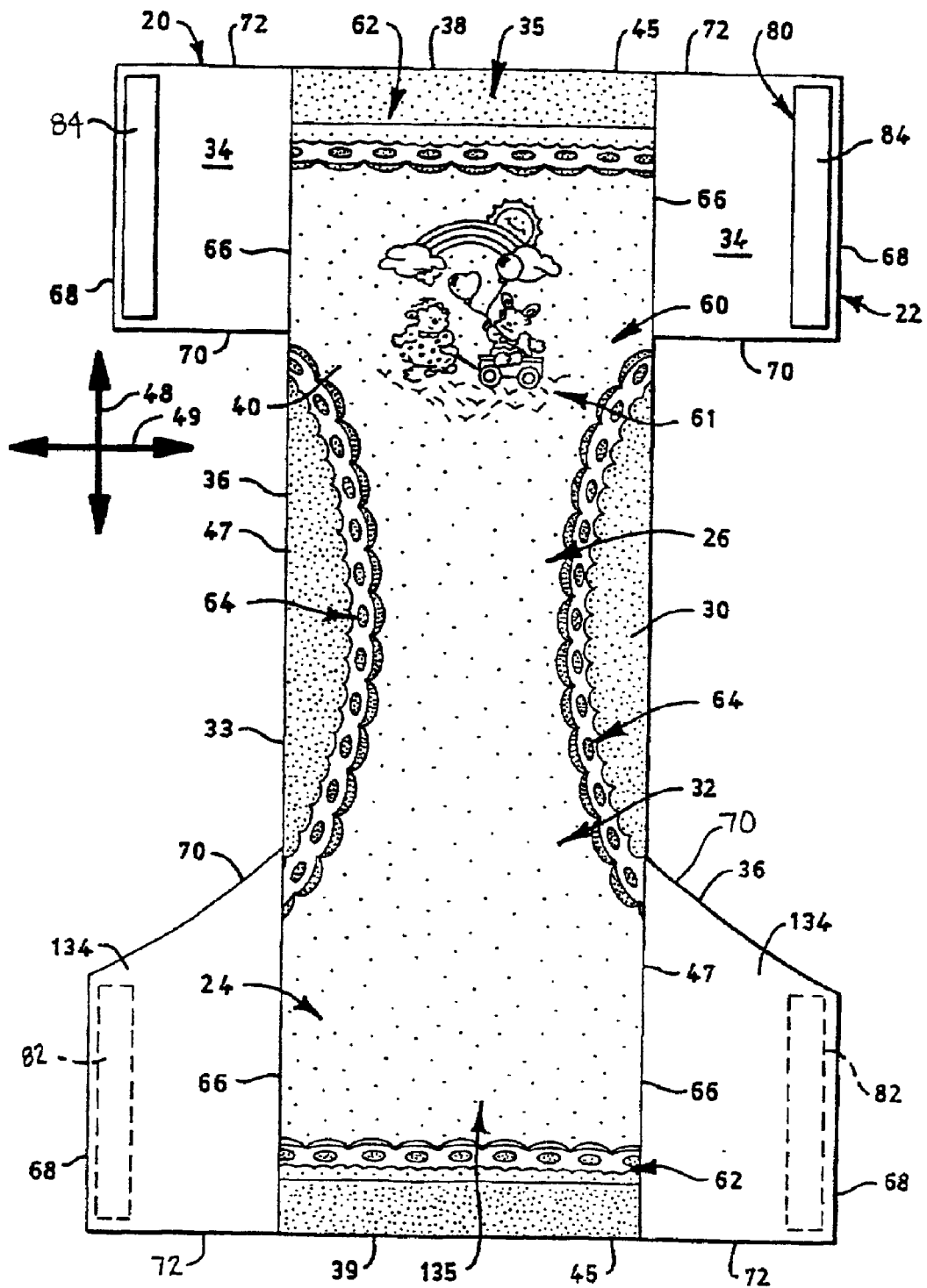
FIG. 2 is a bottom plan view of the training pants of FIG. 1 shown in an unfastened, stretched and laid flat condition and showing a surface of the training pants which faces away from the wearer.
Figure 3:
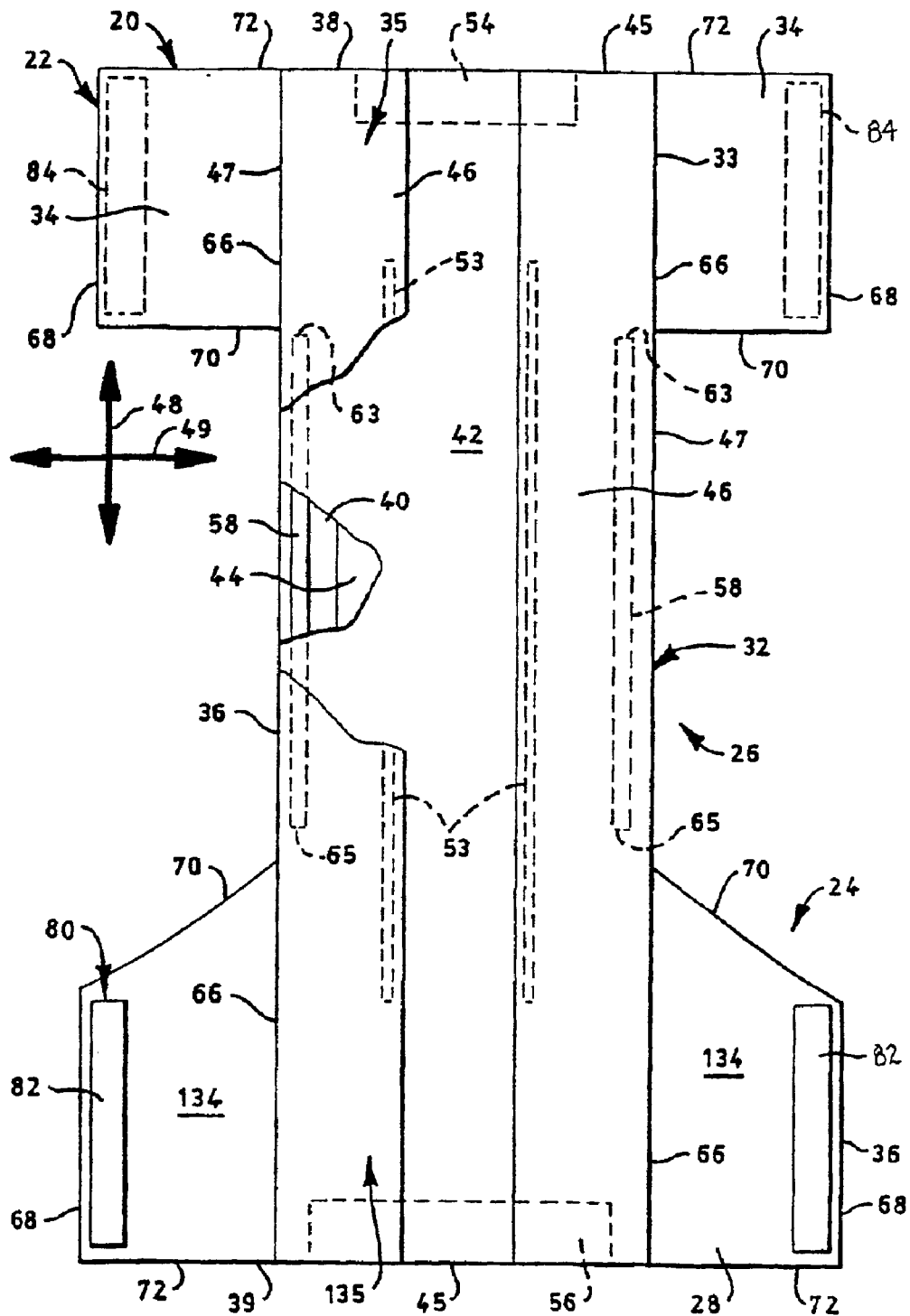
FIG. 3 is a top plan view similar to FIG. 2 but showing a surface of the training pants which faces the wearer, and with portions cut away to reveal underlying features.

The illustrated absorbent chassis 32 comprises a composite structure 33 (FIG. 3), which when laid flat can be rectangular or any other desired shape, a pair of laterally opposite front side panels 34, and a pair of laterally opposite back side panels 134. The composite structure 33 and side panels 34 and 134 may comprise two or more separate elements, as shown in FIG. 1, or be integrally formed. Integrally formed side panels and composite structure would comprise at least some common materials, such as the bodyside liner, flap composite, outer cover, other materials and/or combinations thereof, and could define a one-piece elastic, stretchable, or nonstretchable pants. The illustrated composite structure 33 comprises an outer cover 40, a bodyside liner 42 (FIGS. 1 and 3) which is connected to the outer cover in a superposed relation, an absorbent assembly 44 (FIG. 3) which is located between the outer cover and the bodyside liner, and a pair of containment flaps 46 (FIG. 3). The illustrated composite structure 33 has opposite linear end edges 45 that form portions of the front and back waist edges 38 and 39, and opposite linear side edges 47 that form portions of the side edges 36 of the absorbent chassis 32 (FIGS. 2 and 3). For reference, arrows 48 and 49 depicting the orientation of the longitudinal axis and the transverse or lateral axis, respectively, of the training pants 20 are illustrated in FIGS. 2 and 3.

With the training pants 20 in the fastened position as partially illustrated in FIG. 1, the front and back waist regions 22 and 24 are joined together to define a three-dimensional pants configuration having a waist opening 50 and a pair of leg openings 52. The front waist region 22 comprises the portion of the training pants 20 which, when worn, is positioned on the front of the wearer while the back waist region 24 comprises the portion of the training pants which, when worn, is positioned on the back of the wearer. The crotch region 26 of the training pants 20 comprises the portion of the training pants which, when worn, is positioned between the legs of the wearer and covers the lower torso of the wearer. The front and back side panels 34 and 134 comprise the portions of the training pants 20 which, when worn, are positioned on the hips of the wearer.

The front waist region 22 of the absorbent chassis 32 includes the transversely opposite front side panels 34 and a front center panel 35 (FIGS. 2 and 3) positioned between and interconnecting the side panels. The back waist region 24 of the absorbent chassis 32 includes the transversely opposite back side panels 134 and a back center panel 135 (FIGS. 2 and 3) positioned between and interconnecting the back side panels. The waist edges 38 and 39 of the absorbent chassis 32 are configured to encircle the waist of the wearer when worn and together define the waist opening 50 (FIG. 1). Portions of the side edges 36 in the crotch region 26 generally define the leg openings 52.

The absorbent chassis 32 is configured to contain and/or absorb any exudates discharged from the wearer. For example, the absorbent chassis 32 desirably although not necessarily comprises the pair of containment flaps 46 which are configured to provide a barrier to the transverse flow of body exudates. A flap elastic member 53 (FIG. 3) can be operatively joined with each containment flap 46 in any suitable manner as is well known in the art. The elasticized containment flaps 46 define an unattached edge which assumes an upright configuration in at least the crotch region 26 of the training pants 20 to form a seal against the wearer's body. The containment flaps 46 can be located along the side edges 36 of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the pair of training pants 20 desirably although not necessarily includes a front waist elastic member 54, a rear waist elastic member 56, and leg elastic members 58, as are known to those skilled in the art (FIG. 3). The waist elastic members 54 and 56 can be operatively joined to the outer cover 40 and/or the bodyside liner 42 along the opposite waist edges 38 and 39, and can extend over part or all of the waist edges. The leg elastic members 58 can be operatively joined to the outer cover 40 and/or the bodyside liner 42 along the opposite side edges 36 and positioned in the crotch region 26 of the training pants 20. The leg elastic members 58 can be longitudinally aligned along each side edge 47 of the composite structure 33. Each leg elastic member 58 has a front terminal point 63 and a back terminal point 65, which represent the longitudinal ends of the elastic gathering caused by the leg elastic members.

The front terminal points 63 can be located adjacent the longitudinally innermost parts of the front side panels 34, and the back terminal points 65 can be located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic constrictive forces are imparted to the substrate. In one particular embodiment, for example, the leg elastic members 58 comprise a plurality of dry-spun coalesced multifilament spandex elastomeric threads sold under the trade name LYCRA® and available from E. I. Du Pont de Nemours and Company, Wilmington, Del., U.S.A.

The outer cover 40 desirably comprises a material which is substantially liquid impermeable, and can be elastic, stretchable or nonstretchable. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J. U.S.A. The liquid permeable outer layer can be any suitable material and desirably one that provides a generally cloth-like texture. One example of such a material is a 20 gsm (grams per square meter) spunbond polypropylene non-woven web. The outer layer may also be made of those materials of which the liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Huntsman Packaging of Newport News, Va. U.S.A. If the outer cover 40 is a single layer of material, it can be embossed and/or matte finished to provide a more cloth-like appearance. As earlier mentioned, the liquid impermeable material can permit water vapors to escape from the interior of the disposable absorbent article, while still preventing liquids from passing through the outer cover 40. A suitable breathable material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn. U.S.A.

As shown in FIGS. 1 and 2, the training pants 20 and in particular the outer cover 40 desirably comprises one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product.

The illustrated training pants 20, which is designed for use by young girls, includes a registered outer cover graphic 60 (FIGS. 1 and 2). In this design, the registered graphic 60 includes a primary pictorial image 61, simulated waist ruffles 62, and simulated leg ruffles 64. The primary pictorial image 61 includes a rainbow, sun, clouds, animal characters, wagon and balloons. Any suitable design can be utilized for training pants intended for use by young girls, so as to be aesthetically and/or functionally pleasing to them and the caregiver. The appearance-related components are desirably positioned on the training pants 20 at selected locations, which can be carried out using the methods disclosed in U.S. Pat. No. 5,766,389 issued Jun. 16, 1998 to Brandon et al., the entire disclosure of which is incorporated herein by reference. The primary pictorial image 61 is desirably positioned in the front waist region 22 along the longitudinal center line of the training pants 20.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness. Alternatively, the bodyside liner 42 can be more hydrophilic or can have essentially the same affinity for moisture as the absorbent assembly 44 to present a relatively wet surface to the wearer to increase the sensation of being wet. This wet sensation can be useful as a training aid. The hydrophilic/hydrophobic properties can be varied across the length, width and depth of the bodyside liner 42 and absorbent assembly 44 to achieve the desired wetness sensation or leakage performance.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture comprising Ahcovel-62 from Hodgson Textile Chemicals of Mount Holly, N.C., U.S.A. and Glucopan 220UP from Henkel Corporation of Ambler, Pa. in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal center line.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. The outer cover 40, bodyside liner 42 and other materials used to construct the pants can comprise elastomeric or nonelastomeric materials.

The absorbent assembly 44 (FIG. 3) is positioned between the outer cover 40 and the bodyside liner 42, which can be joined together by any suitable means such as adhesives, ultrasonic bonds, thermal bonds, or the like. The absorbent assembly 44 can be any structure which is generally compressible, conformable, non-irritating to the child's skin, and capable of absorbing and retaining liquids and certain body wastes, and may be manufactured in a wide variety of sizes and shapes, and from a wide variety of liquid absorbent materials commonly used in the art. For example, the absorbent assembly 44 can suitably comprise a matrix of hydrophilic fibers, such as a web of cellulosic fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 which can be rectangular or any other desired shape comprises a blend of wood pulp fluff and superabsorbent material. One preferred type of pulp is identified with the trade designation CR1654, available from U.S. Alliance, Childersburg, Ala., U.S.A., and is a bleached, highly absorbent sulfate wood pulp containing primarily soft wood fibers and about 16 percent hardwood fibers. As a general rule, the superabsorbent material is present in the absorbent assembly 44 in an amount of from 0 to about 90 weight percent based on total weight of the absorbent assembly. The absorbent assembly 44 suitably has a density within the range of about 0.10 to about 0.35 grams per cubic centimeter. The absorbent assembly 44 may or may not be wrapped or encompassed by a suitable tissue wrap that may help maintain the integrity and/or shape of the absorbent assembly.

The absorbent chassis 32 can also incorporate other materials designed primarily to receive, temporarily store, and/or transport liquid along the mutually facing surface with absorbent assembly 44, thereby maximizing the absorbent capacity of the absorbent assembly. One suitable material is referred to as a surge layer (not shown) and comprises a material having a basis weight of about 50 to about 120 grams per square meter, and comprising a through-air-bonded-carded web of a homogenous blend of 60 percent 3 denier type T-256 bicomponent fiber comprising a polyester core/polyethylene sheath and 40 percent 6 denier type T-295 polyester fiber, both commercially available from Kosa Corporation of Salisbury, N.C., U.S.A.

As noted previously, the illustrated pair of training pants 20 has front and back side panels 34 and 134 disposed on each side of the absorbent chassis 32. The front side panels 34, 36 can be permanently bonded along seams 66 to the composite structure 33 of the absorbent chassis 32 in the respective front and back waist regions 22 and 24. More particularly, as seen best in FIGS. 2 and 3, the front side panels 34 can be permanently bonded to and extend transversely outward beyond the linear side edges 47 of the composite structure 33 in the front waist region 22, and the back side panels 134 can be permanently bonded to and extend transversely outward beyond the linear side edges of the composite structure in the back waist region 24. The side panels 34 and 134 may be bonded to the composite structure using attachment means known to those skilled in the art such as adhesive, thermal or ultrasonic bonding. Alternatively, the side panels 34 and 134 can be formed as an integral portion of a component of the composite structure 33. For example, the side panels can comprise a generally wider portion of the outer cover 40, the bodyside liner 42, and/or another component of the absorbent chassis. The front and back side panels 34 and 134 can be permanently bonded together or be releasably attached to one another as illustrated by the fastening system 80.

The illustrated side panels 34 and 134 each define a distal edge 68 that is spaced from the seam 66, a leg end edge 70 disposed toward the longitudinal center of the training pants 20, and a waist end edge 72 disposed toward a longitudinal end of the training pants. The leg end edge 70 and waist end edge 72 extend from the side edges 47 of the composite structure 33 to the distal edges 68. The leg end edges 70 of the side panels 34 and 134 form part of the side edges 36 of the absorbent chassis 32. In the back waist region 24, the leg end edges 70 are desirably although not necessarily curved and/or angled relative to the transverse axis 49 to provide greater coverage toward the back of the pants as compared to the front of the pants. The waist end edges 72 are desirably parallel to the transverse axis 49. The waist end edges 72 of the front side panels 34 form part of the front waist edge 38 of the absorbent chassis 32, and the waist end edges 72 of the back side panels 134 form part of the back waist edge 39 of the absorbent chassis.

In particular embodiments for improved fit and appearance, the side panels 34 and 134 desirably have an average length measured parallel to the longitudinal axis 48 that is about 20 percent or greater, and particularly about 25 percent or greater, of the overall length of the absorbent article, also measured parallel to the longitudinal axis 48. For example, in training pants which have an overall length of about 54 centimeters, the side panels 34 and 134 desirably have an average length of about 10 centimeters or greater, such as about 15 centimeters. While each of the side panels 34 and 134 extend from the waist opening 50 to one of the leg openings 52, the illustrated back side panels 134 have a continually decreasing length dimension moving from the attachment line 66 to the distal edge 68, as is best shown in FIGS. 2 and 3.

Each of the side panels 34 and 134 can include one or more individual, distinct pieces of material. In particular embodiments, for example, each side panel 34 and 134 can include first and second side panel portions that are joined at a seam, or can include a single piece of material which is folded over upon itself (not shown).

The side panels 34 and 134 desirably although not necessarily comprise an elastic material capable of stretching in a direction generally parallel to the transverse axis 49 of the training pants 20. Suitable elastic materials, as well as one process of incorporating elastic side panels into a pair of training pants 20, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No, 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may comprise other woven or nonwoven materials, such as those described above as being suitable for the outer cover 40 or bodyside liner 42; mechanically pre-strained composites; or stretchable but inelastic materials.

The illustrated training pants 20 includes a fastening system 80 for refastenably securing the training pants about the waist of the wearer. The illustrated fastening system 80 includes first fastening components 82 that are adapted to refastenably connect to mating second fastening components 84. In one embodiment, one surface of each of the first fastening components 82 comprises a plurality of engaging elements that project from that surface. The engaging elements of the first fastening components 82 are adapted to repeatedly engage and disengage engaging elements of the second fastening components 84.

In one particular embodiment, the first fastening components 82 each comprise hook type fasteners and the second fastening components 84 each comprise complementary loop type fasteners. In another particular embodiment, the first fastening components 82 each comprise loop type fasteners and the second fastening components 84 each comprise complementary hook type fasteners. Alternatively, the fastening components can comprise interlocking similar surface fasteners, adhesive or cohesive fastening elements such as an adhesive fastener and an adhesive-receptive landing zone or material, or the like. Although the training pants of FIG. 1 illustrates the back waist region 24 overlapping the front waist region 22, which is convenient, the training pants 20 can also be configured so that the front waist region overlaps the back waist region.

Loop type fasteners typically comprise a fabric or material having a base or backing structure and a plurality of loop members extending upwardly from at least one surface of the backing structure. The loop material can be formed of any suitable material, such as acrylic, nylon, polypropylene or polyester, and can be formed by methods such as warp knitting, stitch bonding or needle punching. Loop type materials can also comprise any fibrous structure capable of entangling or catching hook type materials, such as carded, spunbonded or other nonwoven webs or composites, including elastomeric and nonelastomeric composites. Suitable loop materials are available from Guilford Mills, Inc., Greensboro, N.C., U.S.A. under the trade designation No. 36549. Another suitable loop material can comprise a pattern un-bonded web as disclosed in U.S. Pat. No. 5,858,515 issued Jan. 12, 1999 to Stokes et al.

Hook type fasteners typically comprise a fabric or material having a base or backing structure and a plurality of hook members extending upwardly from at least one surface of the backing structure. In contrast to the loop type fasteners which desirably comprise a flexible fabric, the hook material advantageously comprises a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded from nylon, polypropylene or another suitable material. Suitable single-sided hook materials for the fastening components 82, 84 are available from commercial vendors such as Velcro Industries B.V., Amsterdam, Netherlands or affiliates thereof, and are identified as Velcro HTH-829 with a uni-directional hook pattern and having a thickness of about 0.9 millimeters (35 mils) and HTH-851 with a uni-directional hook pattern and having a thickness of about 0.5 millimeters (20 mils); and Minnesota Mining & Manufacturing Co., St. Paul, Minn. U.S.A., including specific materials identified as CS-600.

With particular reference to FIG. 3, the fastening components 82 are disposed on the inner surface 28 of the training pants 20 in the back waist region 24. The fastening components 82 are desirably positioned along the distal edges 68 of the back side panels 134, and abutting or adjacent to the waist end edge 72. In certain embodiments, for example, the first fastening components 82 can be located within about 2 centimeters, and more particularly within about 1 centimeter, of the distal edges 68, the waist end edges 72, and the leg end edges 70.

With particular reference to FIG. 2, the second fastening components 84 are disposed on the outer surface 30 of the front side panels 34. The second fastening components 84 are sized to receive the first fastening components 82 and are desirably positioned along the distal edges 68 of the front side panels 34, and abutting or adjacent to the waist end edge 72. As an example, the second fastening components 84 can be located within about 2 centimeters, and more particularly within about 1 centimeter, of the distal edges 68, the waist end edges 72, and the leg end edges 70. Where the first fastening components 82 comprise loop type fasteners disposed on the inner surface 28 and the second fastening components 84 comprise hook type fasteners disposed on the outer surface 30, the first fastening components can be sized larger than the second fastening components to ensure coverage of the rigid, outwardly-directed hooks.

The fastening components 82, 84 can be adhered to the respective side panels 134, 34 by any means known to those skilled in the art such as adhesive bonds, ultrasonic bonds or thermal bonds. The fastening components may comprise separate fastening elements or distinct regions of an integral material. For example, the training pants 20 can include an integral second fastening material disposed in the front waist region 22 for refastenably connecting to the first fastening components 82 at two or more different regions, which define the second fastening components 84 (FIG. 1). In a particular embodiment, the fastening components can comprise integral portions of the waist regions. For instance, one of the elastomeric front or back side panels can function as second fastening components 84 in that they can comprise a material that is releasably engageable with fastening components disposed in the opposite waist region.

The fastening components of the illustrated embodiments are rectangular, although they may alternatively be square, round, oval, curved or otherwise non-rectangularly shaped. In particular embodiments, each of the fastening components 82, 84 has a length aligned generally parallel to the longitudinal axis 48 of the training pants 20 and a width aligned generally parallel to the transverse axis 49 of the training pants. For a child of about 9 to about 15 kilograms (20–30 pounds), for example, the length of the fastening components is desirably from about 5 to about 13 centimeters, such as about 10 centimeters, and the width is desirably from about 0.5 to about 3 centimeters, such as about 1 centimeter. With particular embodiments, the fastening components can have a length-to-width ratio of about 2 or greater, such as about 2 to about 25, and more particularly about 5 or greater, such as about 5 to about 8. For other embodiments such as for adult products, it may be desirable for one or more of the fastening components to comprise a plurality of relatively smaller fastening elements. In that case, a fastening component or individual fastening elements may have an even smaller length-to-width ratio, for example, of about 2 or less, and even about 1 or less.

As shown in FIG. 1 when the fastening components 82, 84 are releasably engaged, the side edges 36 of the absorbent chassis 32 in the crotch region 26 define the leg openings 52, and the waist edges 38 and 39 of the absorbent chassis, including the waist end edges 72 of the side panels 34, 134, define the waist opening 50. For improved formation of the leg openings 52, it can be desirable in some embodiments for the front side panels 34 to be longitudinally spaced from the back side panels 134 (see FIGS. 2 and 3). For example, the front side panels 34 can be longitudinally spaced from the back side panels 134 by a distance equal to about 20 percent or greater, particularly from about 20 to about 60 percent, and more particularly from about 35 to about 50 percent, of the overall length of the absorbent article.

When engaged, the fastening components 84, 82 define refastenable engagement seams 88 (FIG. 1) at which the respective front and back side panels 34, 134 are connected. In the illustrated embodiment the fastening components 82, 84 are sized relative to each other such that the engagement seams 88 extend substantially the entire distance between the waist opening 50 and the leg openings 52. More specifically, the engagement seams 88 can cover about 80 to 100 percent, and particularly about 90 to about 98 percent, of the distance between the waist opening 50 and each leg opening 52, which distance is measured parallel to the longitudinal axis 48. To construct the engagement seams 88 to extend substantially the entire distance between the waist and leg openings 50 and 52, the fastening components 82, 84 can be formed to cover about 80 to 100 percent, and more particularly about 90 to about 98 percent, of the distance between the waist end edge 72 and the leg end edge 70 of the side panels 34 and 134. However, it is contemplated that the fastening components 82, 84 may instead comprise one or more smaller fasteners covering a smaller portion of the distance between the waist opening 50 and the leg openings 52, for example, about 20 to about 70 percent of the distance between the waist opening and the leg openings.

For the engagement seams 88 to be located at the sides of the wearer, it can be particularly desirable for the transverse distance between the first fastening components 82 to be substantially equal to the transverse distance between the second fastening components 84. The transverse distance between a set of fastening components 82 or 84 is measured parallel to the transverse axis 49 between the longitudinal center lines of the fastening components, measured with the side panels 134 or 34 in an unstretched condition.

Figure 4:
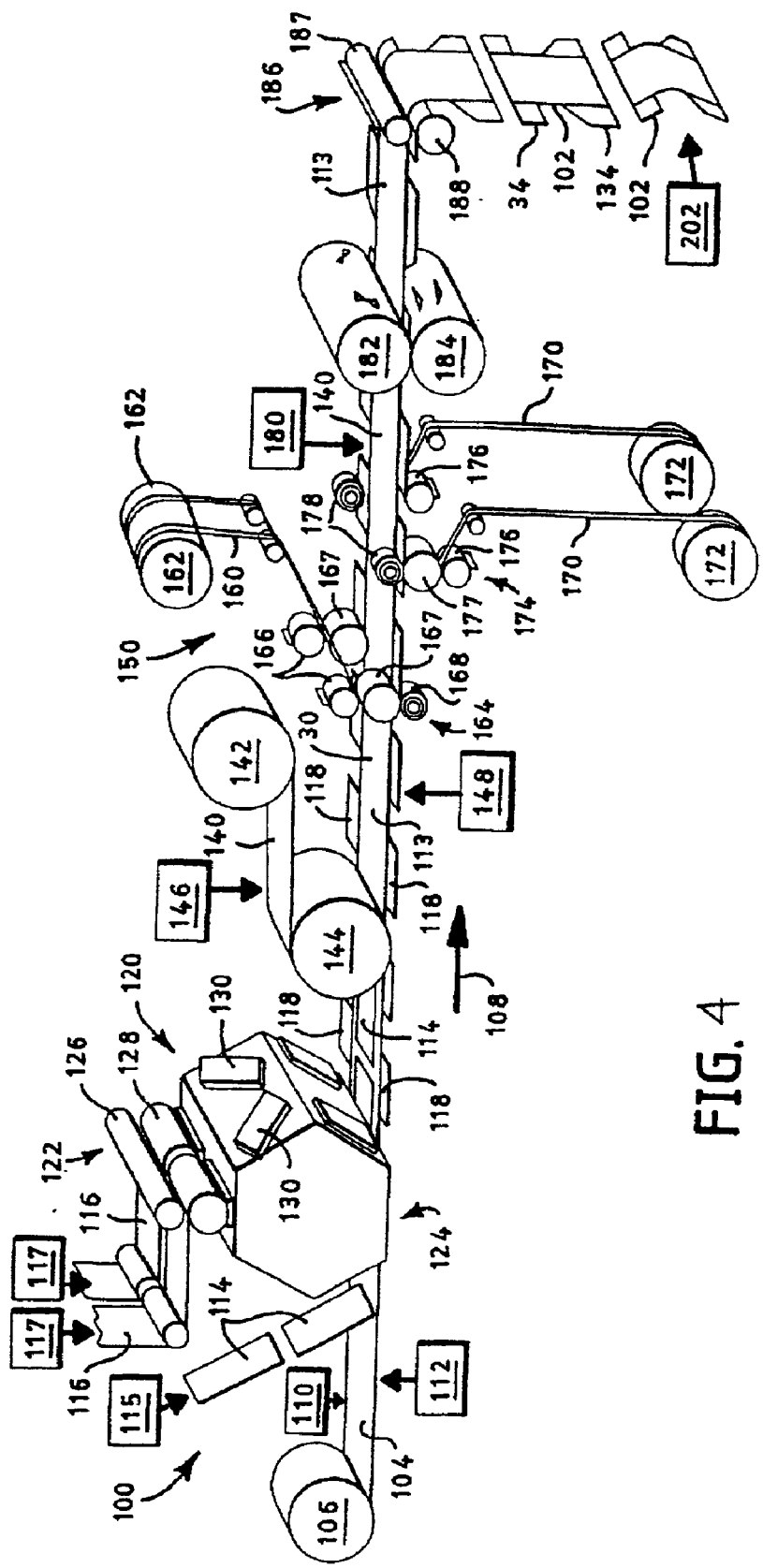
FIG. 4 is a schematic of an assembly section of apparatus of the present invention for making garments such as training pants.
Figure 5:
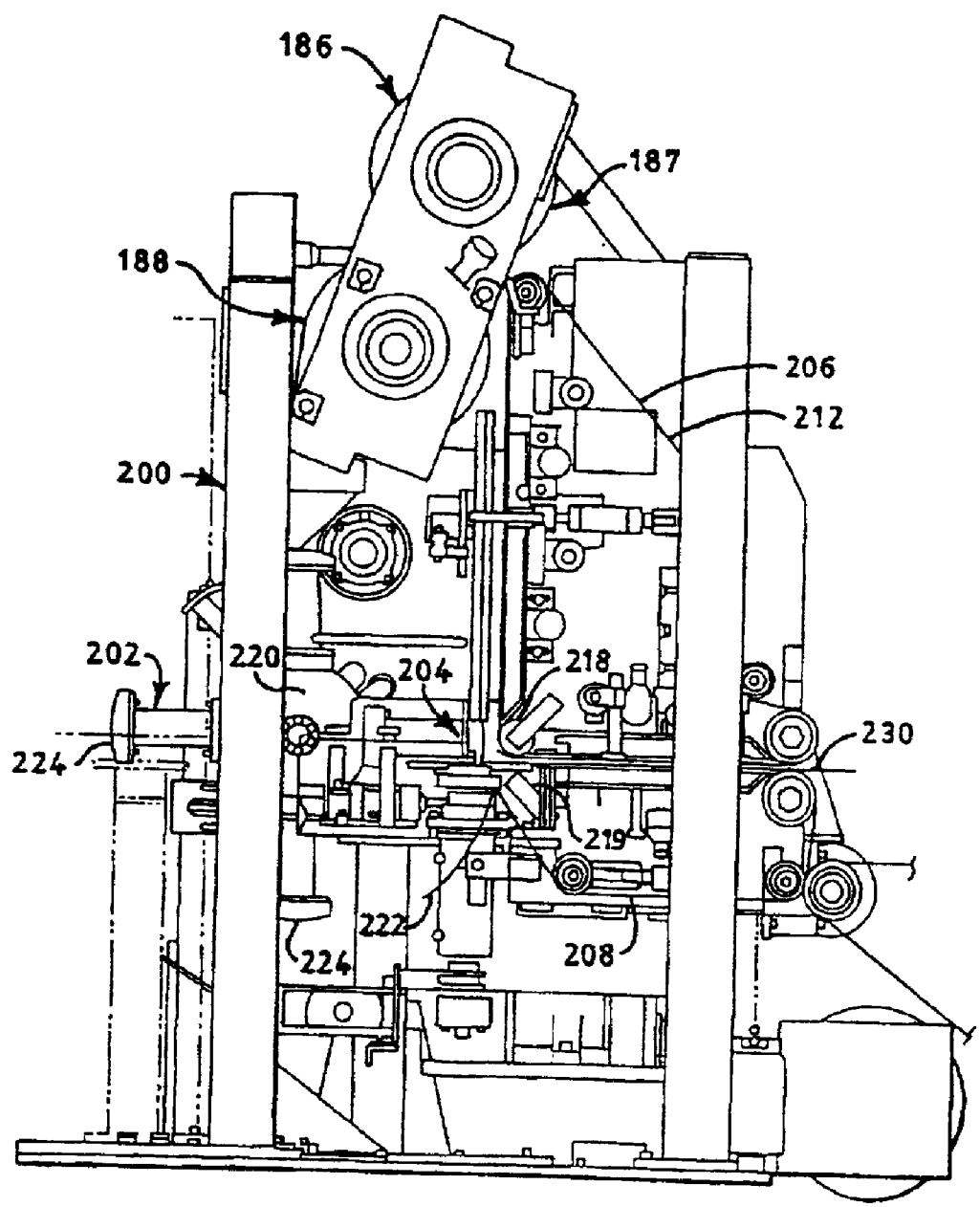
FIG. 5 is a schematic side elevation of a folding section of the apparatus, the folding section following the assembly section shown in FIG. 4.
Figure 6:
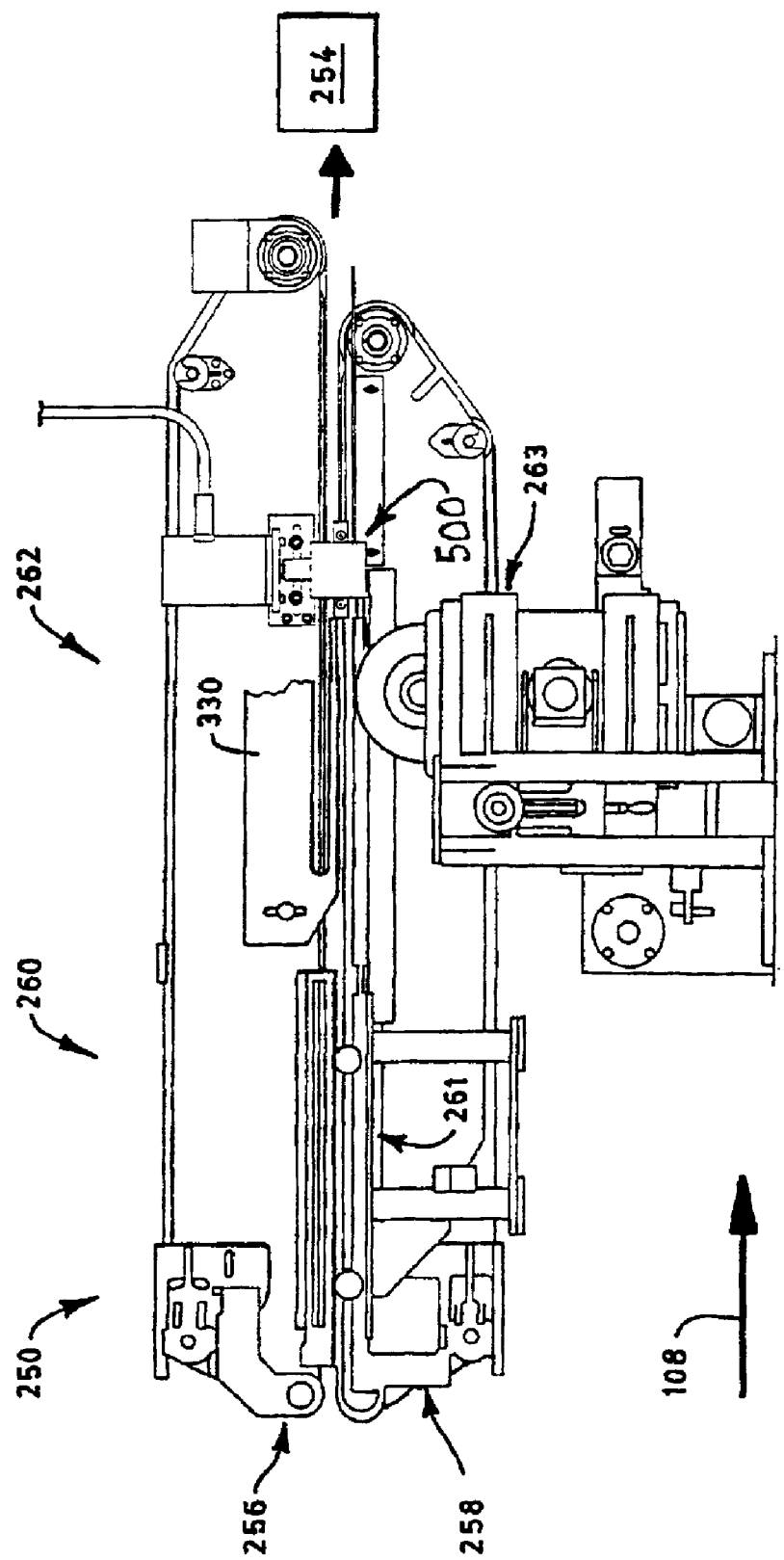
FIG. 6 is a schematic side elevation of a seaming section and nip assembly of the apparatus, the seaming section following the folding section shown in FIG. 5.

FIGS. 4–6 generally illustrate apparatus of the present invention for making a pre-fastened garment, and more particularly for making the training pants 20 shown in FIG. 1. The apparatus comprises an assembly section, generally indicated at 100 in FIG. 4, for making partially assembled pants in an unfolded configuration, a folding section, generally indicated at 200 in FIG. 5, for folding the partially assembled part generally at it crotch region, and a seaming section, generally indicated at 250 in FIG. 6, for engaging the fastening components of the front and back side panels to form the pre-fastened training pants.

The various components of the training pants can be connected together in the assembly section 100 by any means known to those skilled in the art such as, for example, adhesive, thermal and/or ultrasonic bonds. Desirably, most of the components are connected using ultrasonic bonding for improved manufacturing efficiency and reduced raw material costs. Certain garment manufacturing equipment which is readily known and understood in the art, including frames and mounting structures, ultrasonic and adhesive bonding devices, transport conveyors, transfer rolls, guide rolls, tension rolls, and the like, have not been shown in FIGS. 4 and 5. Suitable absorbent supply mechanisms, web unwinds, conveyor systems, registration systems, drive systems, control systems and the like, for use with the present apparatus are disclosed in U.S. Pat. No. 5,766,389 issued Jun. 16, 1998 to Brandon et al., the entire disclosure of which is incorporated herein by reference. Also, the outer cover graphics 60 are not shown in FIGS. 4–7.

With particular reference to the assembly section shown in FIG. 4, a continuous supply of material 104 used to form the bodyside liner 42 is provided from a supply source 106. The supply source 106 can comprise for example any standard unwind mechanism, which generally includes a pair of spindles, a festoon assembly, and a dancer roll for providing bodyside liner material 104 at a desired speed and tension.

Various components can be disposed on and/or bonded to the bodyside liner material 104 as the material travels in a machine direction identified by arrow 108. In particular, a surge layer can be provided at an application station 110 and disposed on and/or bonded to the bodyside liner material 104. The surge layer can comprise either a continuous web or discrete sheets. Additionally, a containment flap module 112 can be provided downstream from the supply source 106 for attaching pre-assembled containment flaps to the bodyside liner material 104. As various components are added in the assembly section 100, a continuously moving product assemblage 113 is formed. The product assemblage 113 will be cut downstream to form the partially assembled, discrete training pants 102.

A plurality of absorbent assemblies 114 can be provided from a suitable supply source 115. The supply source 115 can be any conventional mechanism for supplying the absorbent assemblies 114. Generally, a conventional supply source can include a hammermill for forming fluff fibers and, if desired, for providing an enclosure for mixing superabsorbent material with the fluff fibers, and then depositing the fluff and superabsorbent material on a forming drum having a desired absorbent design. The individual absorbent assemblies 114 can be disposed intermittently on the continuously moving bodyside liner material 104, one for each pair of training pants. The position of the absorbent assemblies 114 can be registered with the position of the surge material, if employed. The absorbent assemblies 114 can be bonded to one or more other components using adhesives or other suitable means. Alternatively, composite absorbent materials can be fed into the converting process from rolls or compressed packages, such as festooned bales.

Continuous webs of material 116 used to form the side panels 34 and 134 can be provided from suitable supply sources 117. The supply sources 117 can comprise one or more standard unwind mechanisms. The side panel material 116 can be cut into individual strips 118 and positioned partially on the bodyside liner material 104 using an applicator device 120. In the cross machine direction, the individual strips 118 desirably extend laterally outward from the bodyside liner material 104 (see FIGS. 4 and 7) and overlap the bodyside liner material by an amount such as about 2 or more centimeters to permit bonding of the strips to the bodyside liner and/or the containment flap material. In the machine direction 108, the position of the strips 118 can be registered relative to the absorbent assemblies 114 so that the product assemblage 113 can be cut between the absorbent assemblies with each strip 118 of side panel material 116 forming both a front side panel 34 and a back side panel 134 of consecutive garments 102.

One suitable applicator device 120 is disclosed in U.S. Pat. No. 5,104,116 issued Apr. 14, 1992 and U.S. Pat. No. 5,224,405 issued Jul. 6, 1993 both to Pohjola, which are incorporated herein by reference. The applicator device 120 can comprise a cutting assembly 122 and a rotatable transfer roll 124. The cutting assembly 122 employs a rotatable knife roll 126 and a rotatable vacuum anvil roll 128 to cut individual strips 118 from the continuous side panel material 116. The strips 118 are cut by a blade on the knife roll 126 and can be maintained on the anvil roll 128 by vacuum and transferred to the transfer roll 124.

The rotatable transfer roll 124 can comprise a plurality of rotatable vacuum pucks 130. The vacuum pucks 130 receive the strips 118 of material 116 from the cutting assembly 122 and rotate and transfer the strips to the continuously moving bodyside liner material 104. When the strips 118 are positioned as desired relative to the bodyside liner material 104, the strips are released from the pucks 130 by extinguishing the vacuum in the pucks. The pucks 130 can continue to rotate toward the cutting assembly 122 to receive other strips.

As disclosed by Van Gompel et al., the material 116 used to form the side panels can alternatively be provided in continuous form and pressurized fluid-jets or a rotary die cutter can be employed to cut the material to form leg openings 52. Still alternatively, the side panels 34 and 134 of the training pants 20 can be provided by portions of the bodyside liner 42 and/or outer cover 40.

A continuous supply of material 140 used to form the outer cover 40 can be provided from a supply roll 142 or other suitable source. The outer cover material 140 can be transported over a laminator roll 144 and bonded to the bodyside liner material 104. The absorbent assemblies 114 are thereby sandwiched between the continuous materials 104 and 140. The inward portions of the strips 118 of side panel material 116 can also be disposed between the bodyside liner material 104 and the outer cover material 140. Alternative configurations for attaching the side panel material 116 are disclosed by Van Gompel et al. Various components such as leg elastics 58 or waist elastics 54 and 56 can be bonded to the outer cover material 140 at an application station 146 prior to uniting the bodyside liner and outer cover materials 104 and 140. Alternatively, leg elastics or waist elastics can be initially bonded to the bodyside liner material 104 or another material.

Bonding devices 148 such as ultrasonic bonders can be employed downstream from the laminator roll 144 to bond the bodyside liner material 104, side panel material 116 and outer cover material 140. For example, these materials can be transported between a rotary ultrasonic horn and an anvil roll. Suitable rotary ultrasonic horns are described in U.S. Pat. No. 5,110,403 to Ehlert, which is incorporated herein by reference. Such rotary ultrasonic horns generally have a diameter of from about 5 to about 20 centimeters and a width of from about 2 to about 15 centimeters. Alternatively, the ultrasonic horn may be a stationary ultrasonic horn as is also known to those skilled in the art. Other suitable ultrasonic horns and ultrasonic bonders are commercially available from Branson Sonic Power Company, Danbury, Conn., U.S.A. The bonding devices 148 could otherwise be a thermal or adhesive bonder as are well known.

The continuously moving product assemblage 113 next advances to a fastener application station 150 where fastening components 82, 84 are bonded to the strips 118 of side panel material 116. The location of the fastening components on the composite is a function in part of the configuration of the assembly section 100. As shown in FIG. 4, the assembly section 100 of the illustrated embodiment is configured so that the upward facing surface of the product assemblage 113 will become the outer surface 30 of the training pants 20 and the downward facing surface will become the inner surface 28. Moreover, the illustrated assembly section 100 is configured to produce partially assembled training pants 102 having the front waist region 22 of a leading garment connected to the back waist region 24 of a trailing garment. However, it is understood that the assembly section 100 could alternatively employ any combination of different orientations. For example, the upward facing surface of the product assemblage 113 could form the inner surface 28 of finished garments. Additionally or alternatively, the back waist region 24 of a leading garment can be connected to the front waist region 22 of a trailing garment, or the garments can be arranged in a front-to-front/back-to-back relationship. Still alternatively, the assembly section 100 could be constructed as a cross-machine direction process wherein the longitudinal axis 48 of each garment could be perpendicular to the machine direction 108 during part or all of the assembly process.

Figure 7:
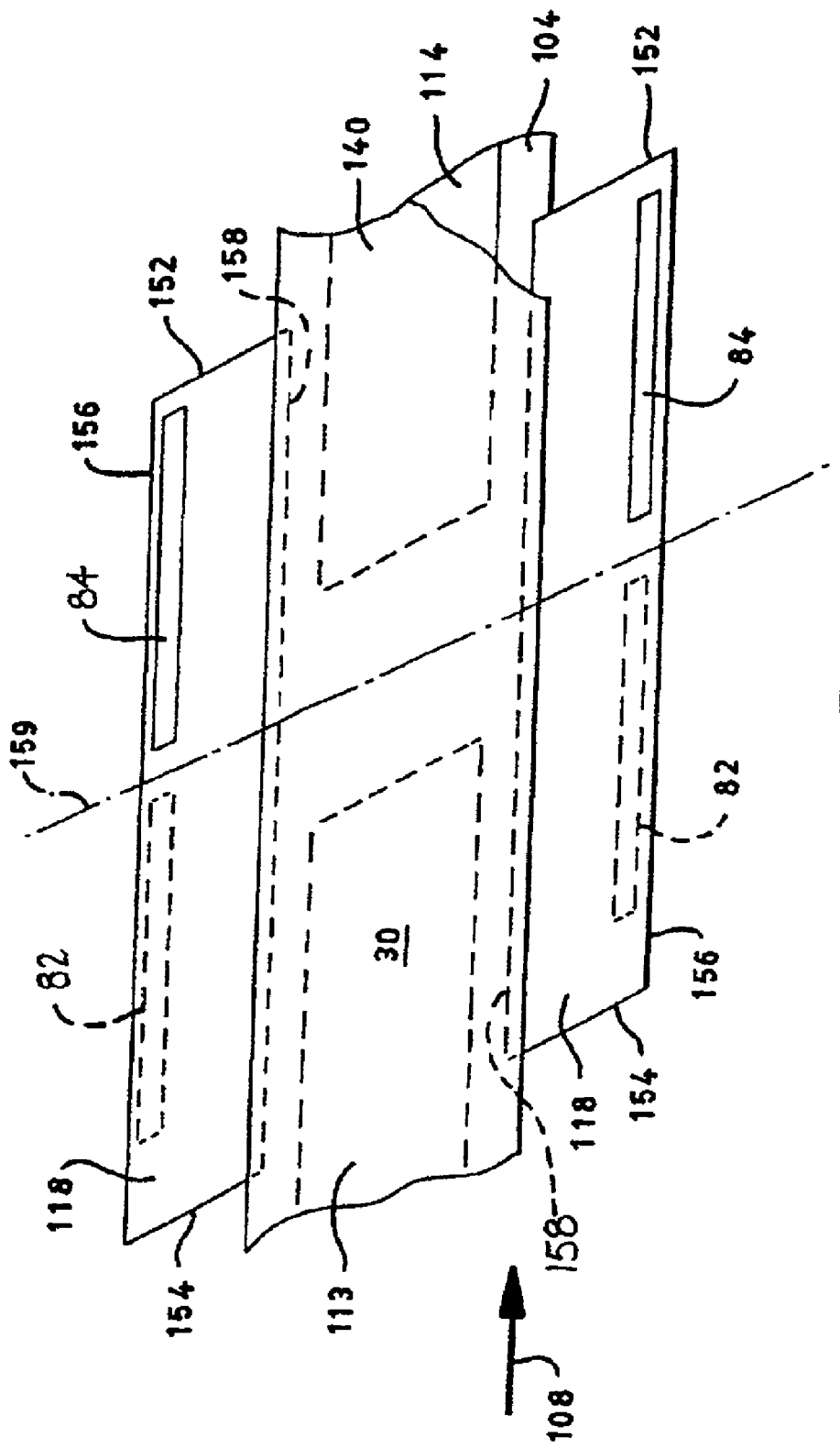
FIG. 7 is a schematic of a portion of a continuously moving assemblage at one point in the assembly section illustrated in FIG. 4.

The locations of the fastening components 82, 84 in this embodiment are best illustrated in FIG. 7, which shows a portion of the product assemblage 113 moving in the direction of arrow 108 immediately following the fastener application station 150. Each individual strip 118 of side panel material 116 defines a leading edge 152, a trailing edge 154, a distal edge 156 and an interior edge 158. A dashed line 159 illustrates the location at which the product assemblage 113 can subsequently be cut to provide the discrete training pants 102. Based on the illustrated orientation of the continuously moving product assemblage 113, the first fastening components 82 can be bonded to the underside of the strips 118 and the second fastening components 84 can be bonded to the top of the strips. Additionally, the first fastening components 82 can be disposed relatively closer to the trailing edge 154 and the second fastening components 84 can be disposed relatively closer to the leading edge 152. The first fastening components 82 can be spaced in the machine direction 108 from the second fastening components 84 so that the cut line 159 passes therebetween.

With reference again to FIG. 4, continuous webs of a second fastener material 160 used to form the second fastening components 84 can be provided from supply rolls 162 or other suitable sources. The second fastener materials 160 can be cut into individual second fasteners 84 by cutting assemblies 164 or other suitable devices. The illustrated cutting assemblies 164 include rotatable knife rolls 166, rotatable vacuum anvil rolls 167, and rotatable backing rolls 168. The continuous second fastener materials 160 can be cut by blades on the knife rolls 166, maintained on the anvil rolls 167 by vacuum, and disposed on the top surfaces of the strips 118 of side panel material 116.

Similarly, continuous webs of first fastener material 170 used to form the first fastening components 82 can be provided from supply rolls 172 or other suitable sources. The first fastener materials 170 can be cut into individual first fasteners 82 by cutting assemblies 174 or other suitable devices. The illustrated cutting assemblies 174 include rotatable knife rolls 176, rotatable vacuum anvil rolls 177, and rotatable backing rolls 178. The continuous first fastener materials 170 can be cut by blades on the knife rolls 176, maintained on the anvil rolls 177 by vacuum, and disposed on the undersides of the strips 118 of side panel material 116.

It is contemplated that other arrangements can be used to attach the fastening components 82, 84. For example, the fastening components 82, 84 can be applied to the side panel material 116 prior to uniting the side panel material with the bodyside liner material 104 and/or the outer cover material 140; the fastening components can be applied to the bodyside liner material 104 and/or outer cover material 140, whether separate side panels 34, 134 are used or not; portions of other components such as the bodyside liner and/or outer cover can form one or more of the fastening components; the separate side panels or integral side panels can themselves form one or more of the fastening components; the fastening components can be attached as pre-engaged composites 82, 84; or the like without departing from the scope of this invention.

After the fastening components are disposed on the strips 118 of side panel material 116, bonding devices 180 such as ultrasonic bonders can be employed to bond the fastening components to the strips. For example, the strips 118 can be transported between a rotary ultrasonic horn and an anvil roll, which devices are positioned on each side of the process at the cross machine direction location of the fastening components 82, 84. Particular ultrasonic bond patterns comprising individual, circular bonds which are compatible with mechanical fastening materials are disclosed in U.S. Pat. No. 5,660,666 issued Aug. 26, 1997 to Dilnik et al., which is incorporated herein by reference. Efficient arrangements for attaching the fastening components with nonadhesive bonding devices are further described in published U.S. patent application No. US2002-0000291, filed on May 15, 2001 by J. D. Coenen et al. and titled "Methods For Making Garments With Fastening Components," which is incorporated herein by reference. For secure attachment, it may be desirable to attach the fastening components with both adhesive and thermal bonds. Suitable attachment adhesives are available from commercial vendors such as Findley Adhesive, Inc., Wauwatosa, Wis., U.S.A.

In particular embodiments, the bonding devices 180 can provide timed, non-uniform bonding of the fastening components to the side panel material 116. The degree of bonding, such as the number of bonds per unit area or the bond strength per unit area, can be greater in certain target areas compared to non-target areas. Enhanced bonding in target areas can be beneficial particularly near the waist and leg openings 50 and 52 to reduce delamination of the fastening components from the side panel material 116. Thus, the bonding devices 180 can be adapted to create relatively more bonds or stronger bonds between the fastening components 82, 84 and the side panel material 116 when the side panel material 116 reaches a particular machine direction 108 location. In one particular embodiment, the target areas correspond to portions of the fastening components 82, 84 near the waist edges 38 and 39. The bonding devices 180 can be registered to provide a relatively higher degree of bonding which begins while disposed on one fastening component (such as the fastening component 84 in FIG. 7), continues through the region where the product assemblage 113 will subsequently be cut (see cut line 159 in FIG. 7), and ends after being disposed on another fastening component (such as fastening component 82). Alternatively, the bonding devices 180 can destroy engaging elements of the fastening components 82, 84 in the target areas, so that the fastening components will be less able to aggressively attach to one another in the target areas.

The strips 118 of side panel material 116 can be trimmed if desired, for example to provide angled and/or curved leg end edges 70 in the back waist region 24 (FIGS. 2 and 3). To this end, the assembly section 100 can include a die cutting roll 182 and a backing roll 184. In the illustrated embodiment, a portion of each strip 118 is trimmed from the trailing edge 154 (FIG. 7) in order to form the angled and/or curved leg end edges 70 in the back waist region 24.

The method and apparatus to this point provides a continuous web of interconnected and partially assembled pairs of training pants 102 moving in the direction indicated by arrow 108. This continuously moving product assemblage 113 is passed through a cutter 186 which selectively cuts the web into discrete, partially assembled training pants 102. Such cutters 186 are generally known to those skilled in the art and can include, for example, the combination of a cutting roll 187 and an anvil roll 188 through which the web travels. The anvil roll 188 can include a hardened steel rotating roll while the cutting roll 187 can include one or more flexible hardened steel blades clamped onto another rotating roll. The pinching force between the blade on the cutting roll 187 and the anvil roll 188 creates the cut. The cutting roll 187 can have one or more blades depending upon the desired distance between the cuts. The cutter 186 can further be configured to provide a spacing between the individual cut pieces after they are cut. Such a spacing can be provided by transferring the cut pieces away from the cutter at a higher speed than the speed at which the web is provided to the cutter.

Figure 8:
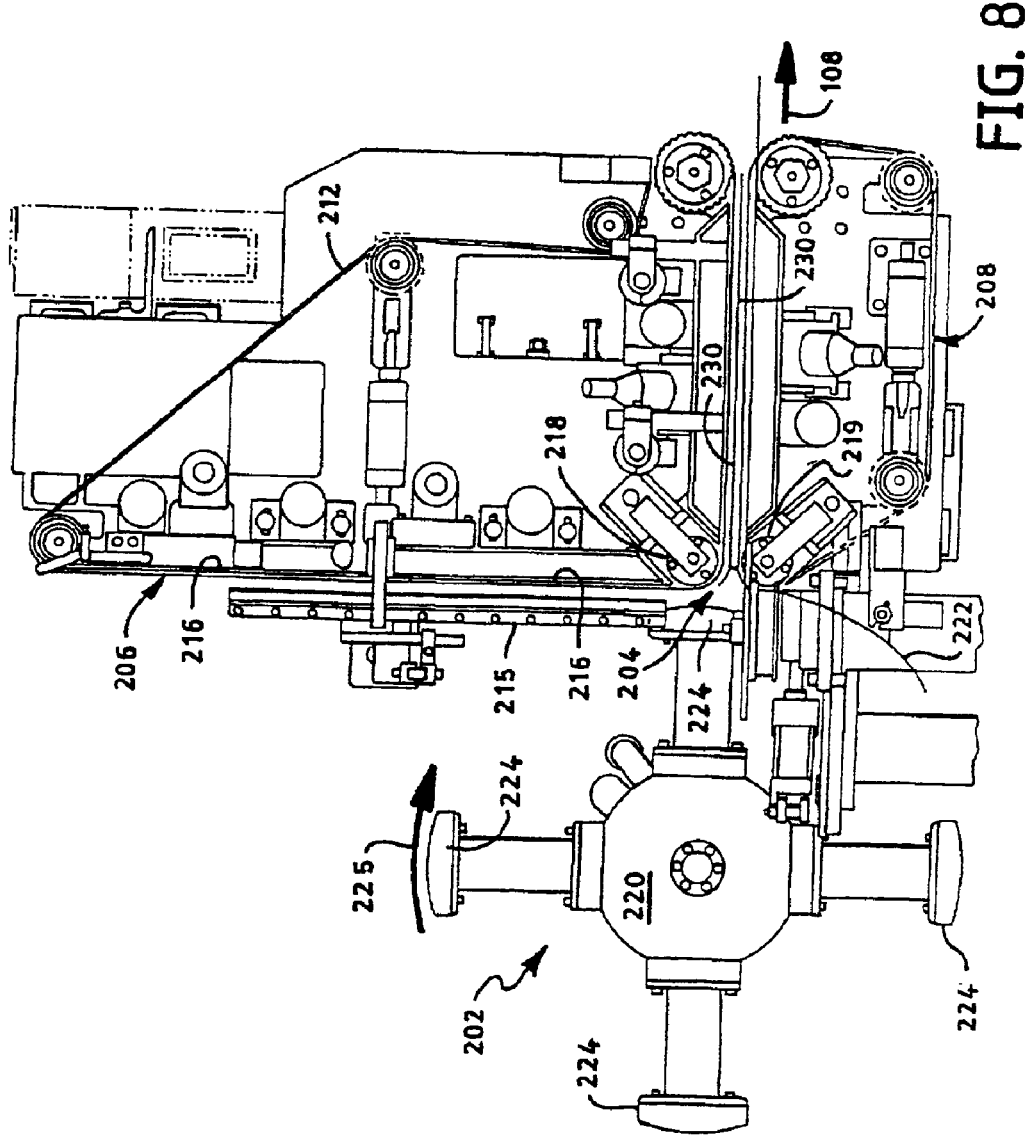
FIG. 8 is an enlarged side elevation of the folding section shown in FIG. 5.
Figure 9:
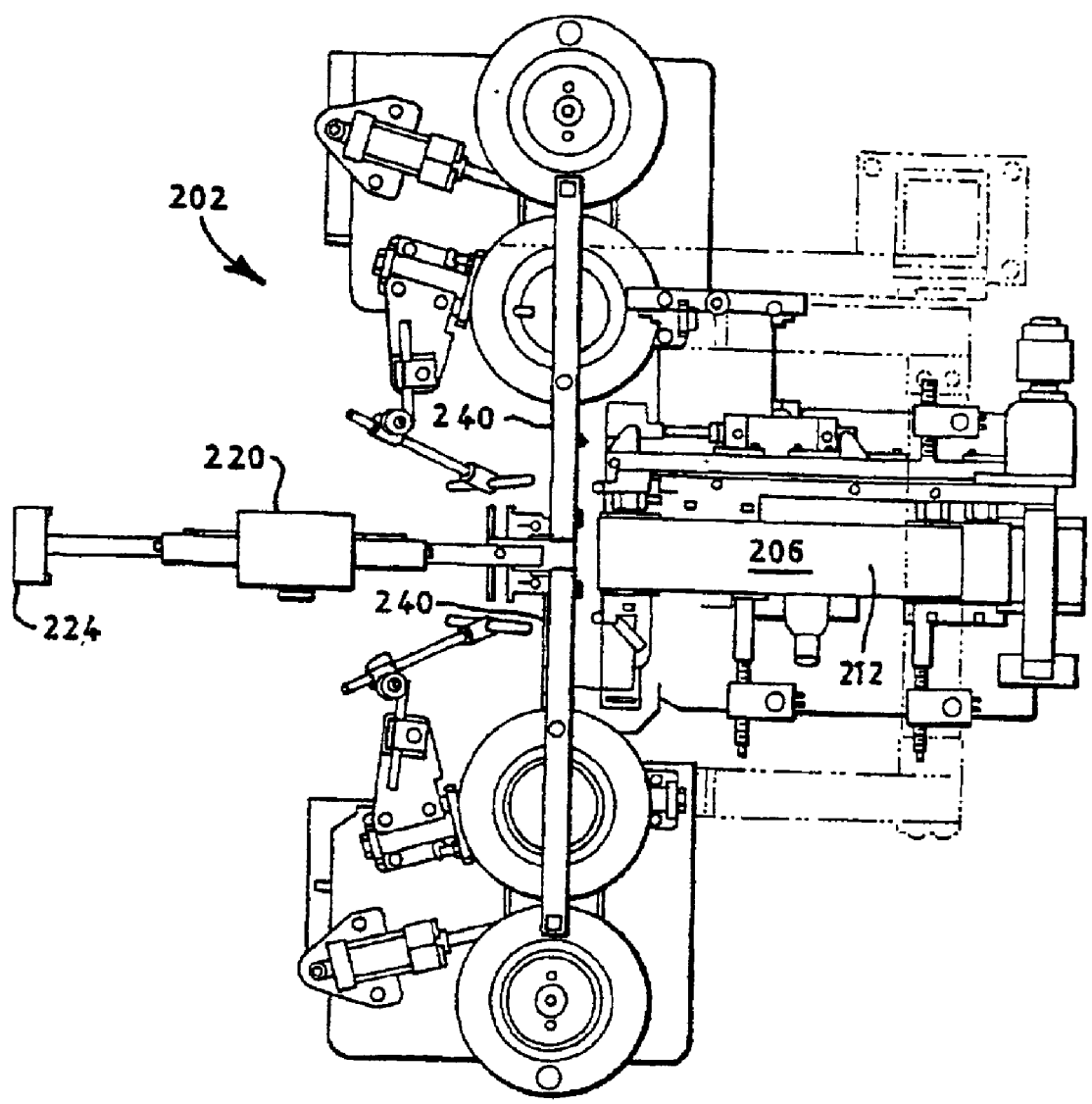
FIG. 9 is a top plan view of a portion of the folding section of FIG. 5.

With particular reference now to FIGS. 5, 8 and 9, the discrete training pants 102 are delivered to and folded at the folding section 200 using any suitable folding mechanism 202. For example, each pair of training pants 102 can be folded about a fold line generally bisecting the training pants such as through the crotch region 26. As such, the waist regions 22 and 24 of the training pants 102 are positioned in facing relationship with the side panels 34 and 134 extending laterally outward parallel to the transverse axis 49 of the training pants. The fold line can extend in a lateral direction through the crotch region 26 of the training pants. Desirably, each of the training pants 102 is consistently folded about the fold line such that the front and back waist edges 38 and 39 of the training pants align with each other.

A variety of folding mechanisms 202 can be used, such as blade folders, linear folders, book folders, tucker blades or the like. The specific type selected for a given application may depend upon the type of garment being manufactured and the type of fastening mechanism used to secure the garment in a pants configuration. In the illustrated embodiment, the folding mechanism 202 controls the side panels 34, 134 during folding so that the refastenable fastening components 82, 84 are inhibited against engaging one another or engaging another material during the folding operation. Other arrangements for maintaining separation of the side panels 34, 134 and fastening components 82, 84 during folding are disclosed in PCT Application No. WO 01/87210, filed by J. D. Coenen et al. and titled "Folding And Manufacture Of Pants," which is incorporated herein by reference.

The illustrated blade folding mechanism 202 comprises a plurality of rotating folding or tucker blades 240 (FIG. 9) which are configured to contact the training pants 102 along the fold line. Rotation of the folding blades 240 can force the training pants 102 into a nip 204 (FIGS. 5 and 8) between two rotating folding conveyors 206 and 208 causing the training pants to fold about the fold line. The folding conveyors 206 and 208 can form part of a transport system for moving the folded training pants 102 in the machine direction 108 (FIG. 8). The folded pair of training pants 102 is illustrated as being transported in the machine direction 108 with the crotch region 26 leading the waist regions 22 and 24. Alternatively, the process and apparatus could be modified so that the waist regions lead the crotch region (not shown).

The series of unfolded, discrete training pants 102 can be transferred from the vacuum anvil roll 188 (FIG. 4) of the cutter 186 to the upper folding conveyor 206 (FIGS. 5, 8 and 9). The training pants 102 can be held by vacuum on the upper folding conveyor 206 and transported toward the nip 204 formed between the folding conveyors 206 and 208. While being transported toward the nip 204, the side panels 34 and 134 can be smoothed out or straightened if desired by various means including fluid stabilizing devices. For example, air knives 215 (FIG. 8), air bars, air nozzles or the like can be mounted in proximity to the upper folding conveyor to provide a stream of fluid directed toward the side panels to stabilize and/or straighten the side panels. The air knives 215 can blow the side panels 34, 134 against skid plates 216 positioned transversely outward from the upper folding conveyor belt 212. Alternatively, or in addition thereto, the upper folding conveyor 206 can incorporate fluid stabilizing devices (not shown) consisting of fluid manifolds operatively connected to a high pressure fluid source to fluidly shake the side panels 34, 134. The fluid stabilizing devices (not shown) desirably prevent folding of the side panels 34 and 134 as the training pants 102 moves along the upper folding conveyor 206. Sensing devices can also be employed at this point to detect products that have folded side panels or that are misaligned relative to the machine center line.

The product folding nip 204 can be formed between a timed vacuum nose roll 218 of the upper folding conveyor 206 and a timed vacuum nose roll 219 of the lower folding conveyor 208 (FIGS. 5 and 8). As the leading edge of each pair of pants 102 is introduced onto the upper nose roll 218, compressed air can be introduced inside the nose roll to negate vacuum draw of the nose roll. This allows the leading edge of the pants to pass by the nose roll 218 without getting sucked into the nip 204. Alternatively of course, the vacuum source can be temporarily disconnected from the nose roll 218. Any suitable control system can be used to repeatedly activate and deactivate vacuum operation of the nose rolls 218 and 219. In particular embodiments, rotary valves (not shown) can be employed to cycle vacuum to the nose rolls 218 and 219.

A product control drum 220 can guide the leading half of the training pants 102 onto a curved transfer plate 222 (FIGS. 5 and 8). The product control drum 220 can comprise a plurality of vacuum pucks 224 which rotate in the direction of arrow 225. The illustrated product control drum 220 includes four vacuum pucks 224 to guide four training pants 102 per revolution. Rotation of the product control drum 220 can be timed so that a vacuum puck 224 grabs the leading half of training pants 102 and transfers the leading edge onto the curved transfer plate 222. The absorbent chassis 32 and/or side panels 134 of the leading half can be carried on a vacuum puck 224 past the nose roll 219 of the lower folding conveyor 208. Compressed air can be introduced inside this lower nose roll 219 at this point to negate vacuum draw and to permit the entire leading edge and side panels 134 to transfer onto the curved transfer plate 222. Alternatively of course, the vacuum source can be temporarily disconnected from the nose roll 219.

With reference to FIG. 9, the opposed tucker blades 240 move in an orbital manner to pass through the vertical path of the training pants 102. The tucker blades 240 can contact the crotch region 26 of the pants 102 and insert the crotch region into the folding nip 204. As this happens, the leading half of the pants 102 reverses direction over the lower folding conveyor 208 and is pulled into the nip 204. The vacuum puck 224 can cease drawing vacuum at this point to release the leading half. Correspondingly, the trailing half of the pants 102 is pulled around the upper nose roll 218. Thus, both halves of the training pants 102 can change from motion in a generally vertical plane to motion between the folding conveyors 206 and 208 in a generally horizontal plane.

Figure 10:
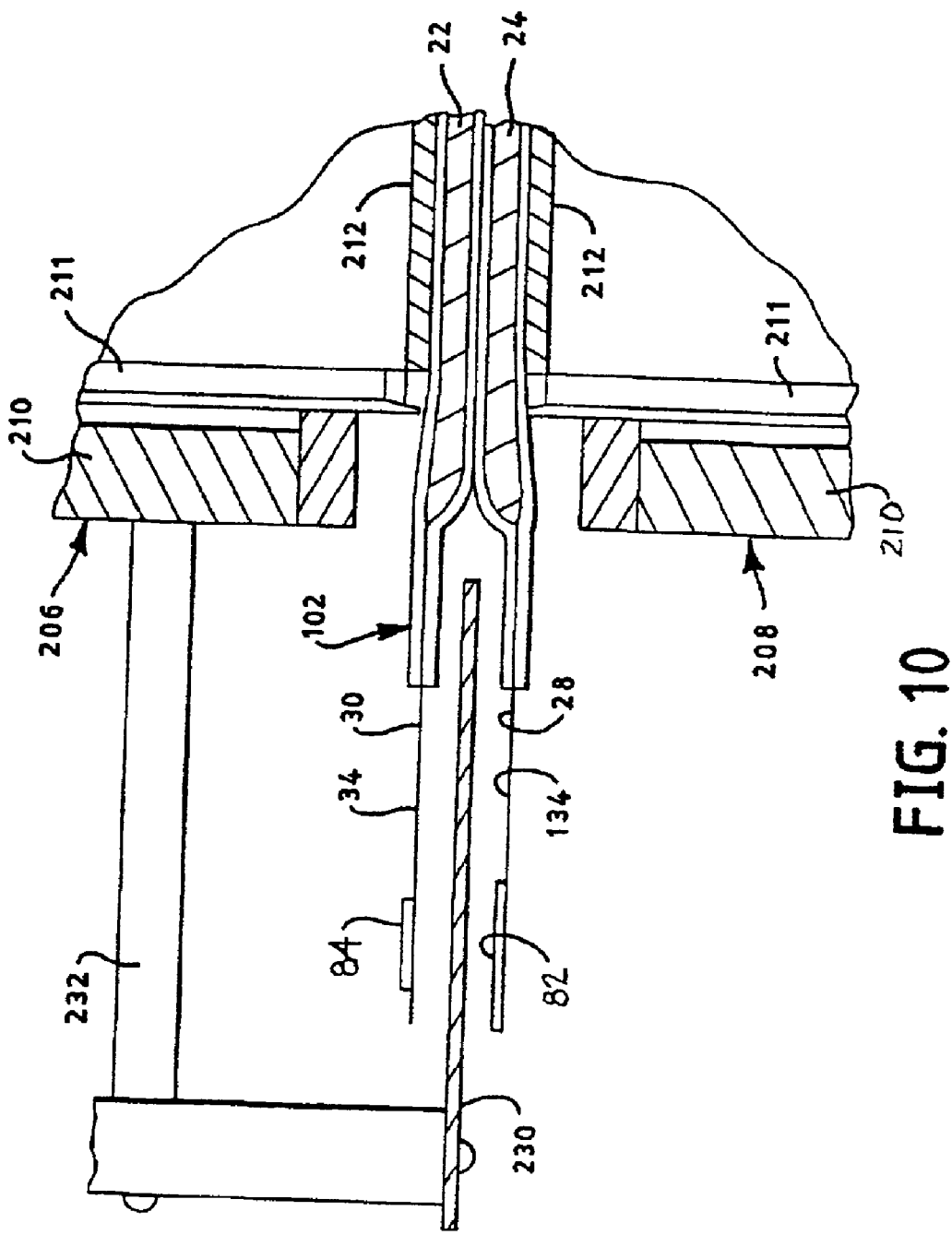
FIG. 10 is an enlarged section view of a portion of a pair of training pants at a position within the folding section shown in FIGS. 5, 8 and 9.

The illustrated folding mechanism 202 can maintain separation between the front and back side panels 34 and 134. As the pants 102 enters the folding nip 204, compressed air can be shut off to the upper nose roll 218 so that the side panels 34 of the trailing half are drawn by vacuum to the upper nose roll. The trailing side panels 34 are thus drawn to the upper nose roll 218 and follow its rotation around the roll and over a side panel separation plate 230 (FIGS. 8 and 10). Similarly, as the leading half of the pants 102 is pulled into the folding nip 204, compressed air can be shut off to the lower nose roll 219 so that the side panels 134 of the leading half are drawn by vacuum to the lower nose roll.

The leading side panels 134 are thus drawn to the lower nose roll 219 and follow its rotation around the roll and beneath the side panel separation plates 230.

FIG. 10 illustrates a portion of a partially assembled pair of training pants 102 positioned between the upper and lower folding conveyors 206 and 208 at a location downstream from the nose rolls 218 and 219. At this point, the pair of pants 102 has been folded in half and is being transported in the machine direction 108 (FIG. 8) by the conveyors 206 and 208. The illustrated folding mechanism 202 can thus maintain the front side panels 34 separated from the back side panels 134 during folding.

Each folding conveyor 206 and 208 as illustrated in greater detail in FIG. 10 can comprise a frame structure 210, a plurality of rotatable pulleys 211 associated with the frame structure, and a continuous belt 212 carried on the pulleys. A drive system and conveyor shaft (not shown) can be used to rotatively drive one or more of the pulleys. The folding conveyors 206 and 208 can comprise vacuum conveyors as are well known in the art, in which case the continuous belt can be formed of a fluid permeable material. The folding conveyors desirably transport the training pants 102 with the longitudinal center line of the pants traveling on the longitudinal center line of the conveyors. As depicted, the front and back side panels 34 and 134 can project laterally outward from the frame structure 210, outstretched in the cross-machine direction.

While traveling on the folding conveyors 206 and 208, the side panels 34 and 134 can be smoothed out or straightened if desired by various means including fluid stabilizing devices (not shown). Suitable fluid stabilizing devices can comprise air knives, air bars, air nozzles, vacuum devices or the like to provide a stream of fluid directed toward the side panels. The fluid stabilizing devices can be incorporated within either or both of the folding conveyors 206 and 208, or can comprise separate devices positioned in proximity to the conveyors.

As a result of the illustrated folding mechanism 202, the front waist region 22 and front side panels 34 of the partially assembled training pants 102 as shown in FIG. 10 are disposed above the back waist region 24 and back side panels 134. The first fastening component 82 is disposed on the inner surface 28 of the back side panel 134 and the second fastening component 84 is disposed on the outer surface 30 of the front side panel 34. The separation plates 230 can extend in the machine direction 108 to maintain separation between the front and back side panels 34, 134. The separation plates 230 can comprise a low friction material or coating, such as: stainless steel; Teflon®; aluminum; ultra-high molecular weight polyethylene (UHMW-PE); polyoxymethylene (acetals), for instance a homopolymer available from E. I. Du Pont de Nemours and Company, Wilmington, Del., USA under the tradename DELRIN; or the like. In particular embodiments, the separation plates 230 can comprise a thin layer of Teflon®, UHMW-PE, DELRIN or the like glued to a plate formed of steel, aluminum or the like. The separation plates can be mounted using suitable support members 232 (FIG. 10) to either the folding conveyors 206 or 208 or other suitable frame structures (not shown).

Now referring to FIG. 6, the continuous stream of discrete, partially assembled and folded training pants 102 is delivered from the folding section 200 to the seaming section 250. The seaming section 250 can encompass apparatus for controlling the unattached side panels 34 and 134, arranging the side panels in an aligned, overlapping or opposed orientation, and engaging the side panels together to form an engagement seam 88. In general, the apparatus can bend the front or back side panels 34 or 134 approximately 90 degrees using an air flow device (see FIG. 14). After one pair of side panels 34 is oriented in this manner, a panel folding mechanism can fold the other pair of side panels 134 so that they are positioned transversely outward from the first pair of side panels (see FIG. 18) in opposed relationship therewith. The second pair of side panels can then be brought into contact with the first pair of side panels. In the embodiment shown in FIG. 1, the side panels 34, 134 are refastenably secured together using mating mechanical fastening components 82, 84, although other refastenable or permanent bonding arrangements can also be used. The seaming section 250 can thus convert the partially assembled and folded training pants 102 into pre-fastened training pants 20 each having a waist opening 50 and a pair of leg openings 52 (FIG. 1). While not shown in the drawings, it is understood that the illustrated seaming section 250 could of course be inverted so that the lower side panel is first folded upward to form the inner side panel. From the seaming section 250, the training pants 20 can be processed through various finishing stations 254, for operations such as side panel tucking, packaging, or the like.

Figure 13:
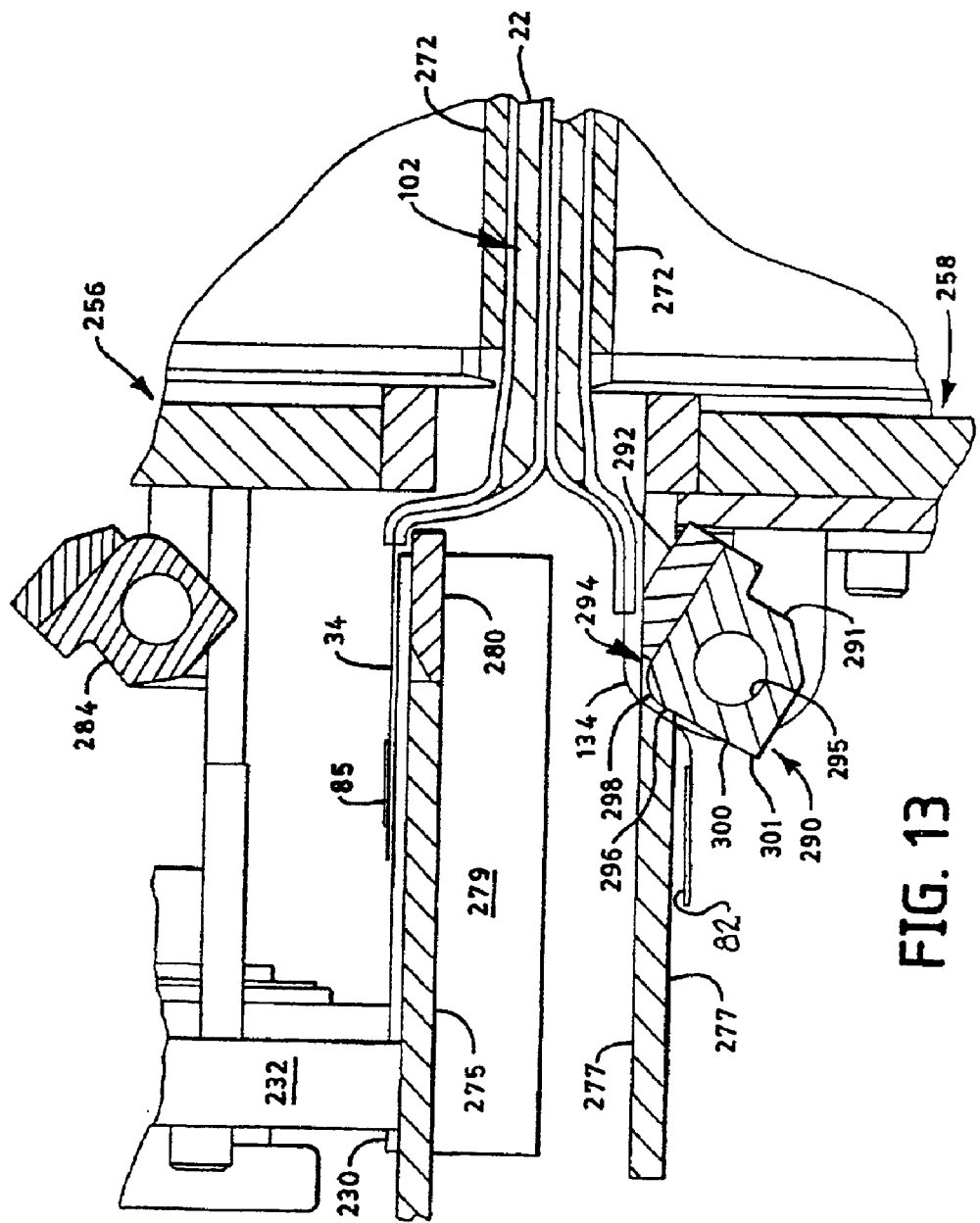
Figure 14:
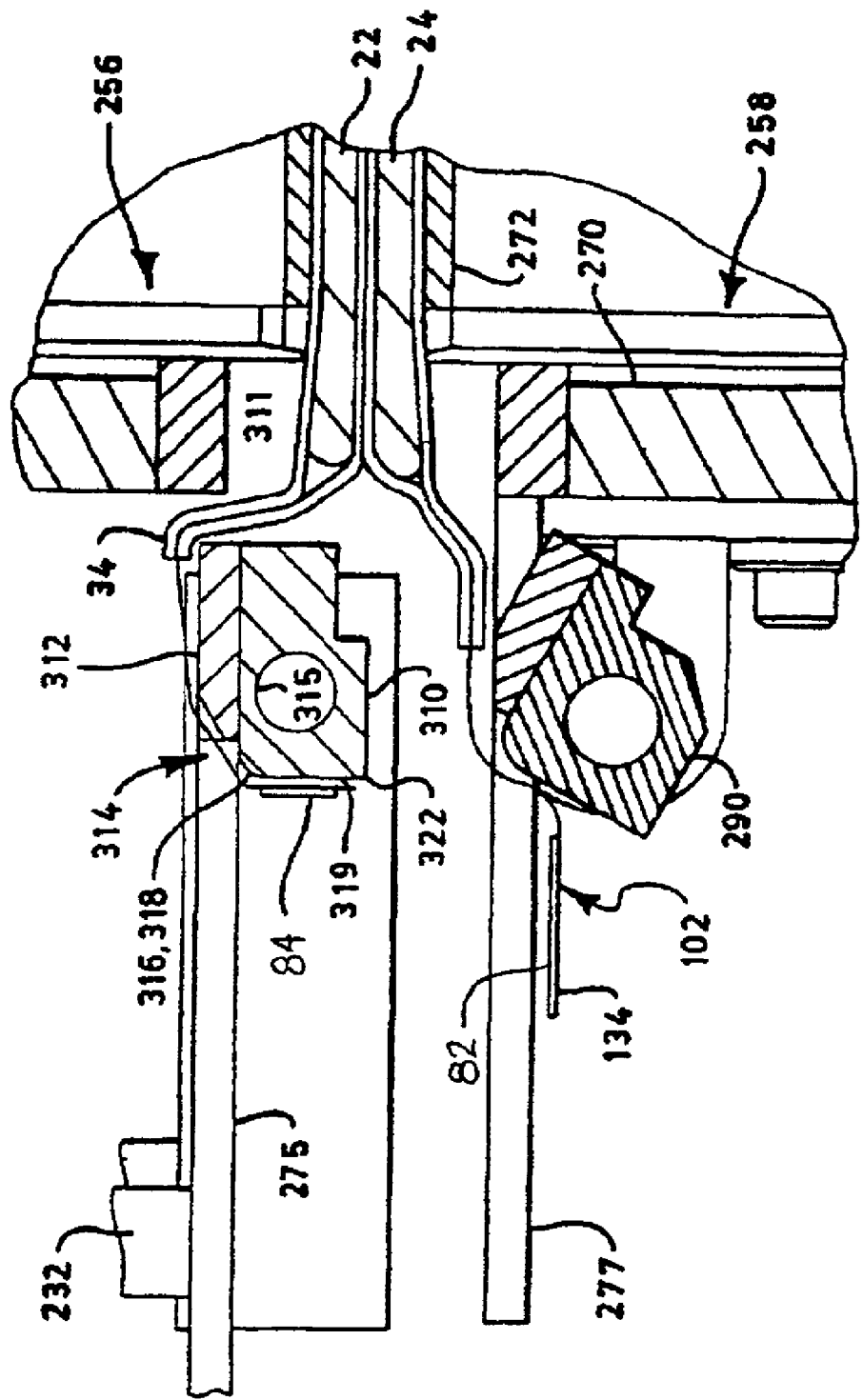
Figure 15:
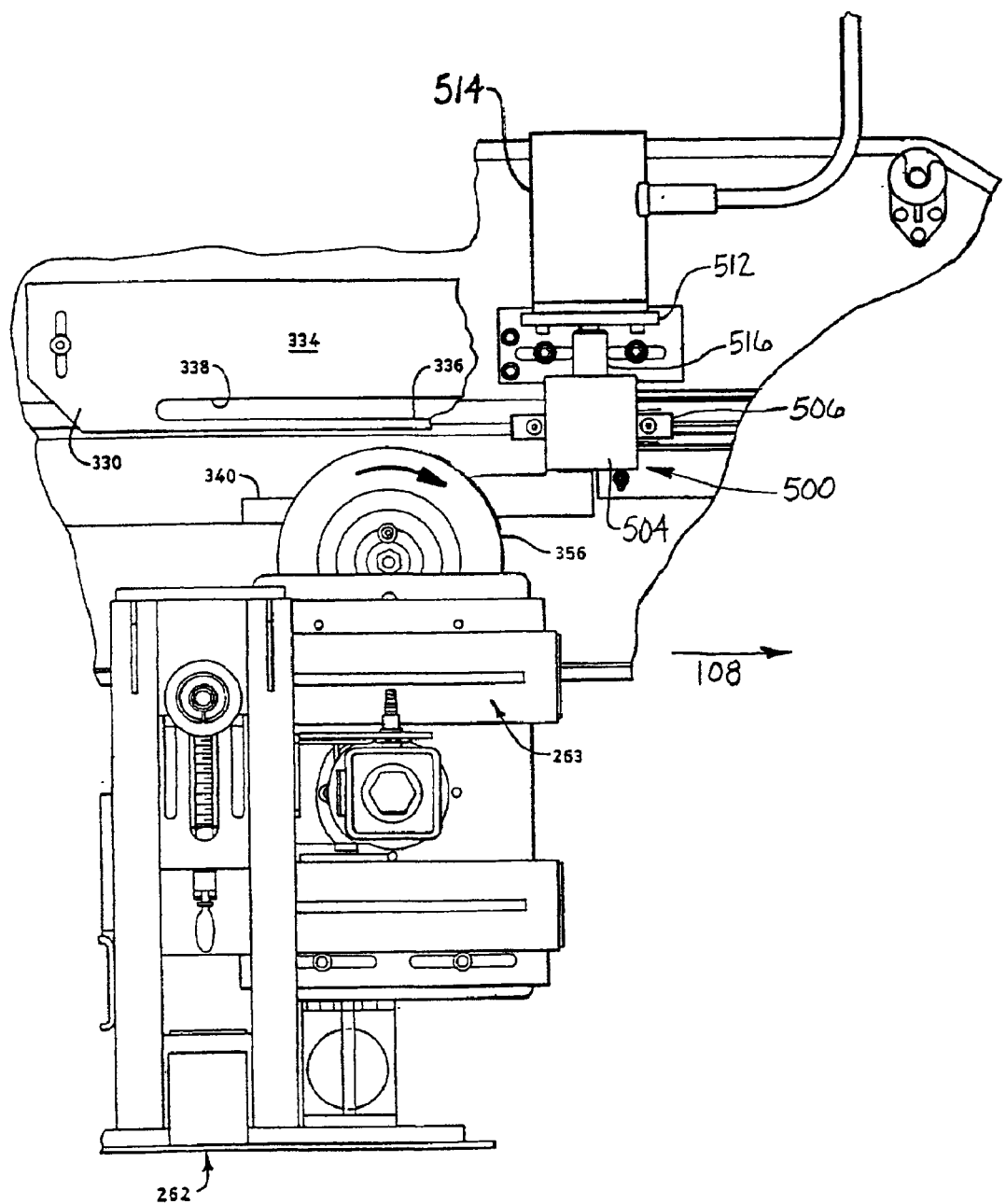
FIG. 15 is an enlarged side view of an exterior panel positioning station of the seaming section and the nip assembly shown in FIG. 6.

The partially assembled training pants 102 can be transported in the machine direction 108 through the seaming section 250 by a transport system, such as conveyors or other suitable means. In the illustrated embodiment, the training pants 102 are transferred from the upper and lower folding conveyors 206 and 208 (FIGS. 5 and 8–10) to upper and lower alignment conveyors 256 and 258 (FIGS. 6, 11–14 and 16–19). The alignment conveyors 256 and 258 transport the training pants 102 through an interior panel positioning station 260 (FIGS. 6 and 11) and an exterior panel positioning station 262 (FIGS. 6 and 15). Suitable conveyor mechanisms such as vacuum conveyors or non-vacuum conveyors are available from various commercial vendors. Alternatively, the transport system can comprise any means to transport the folded products in the machine direction.

Figure 11:
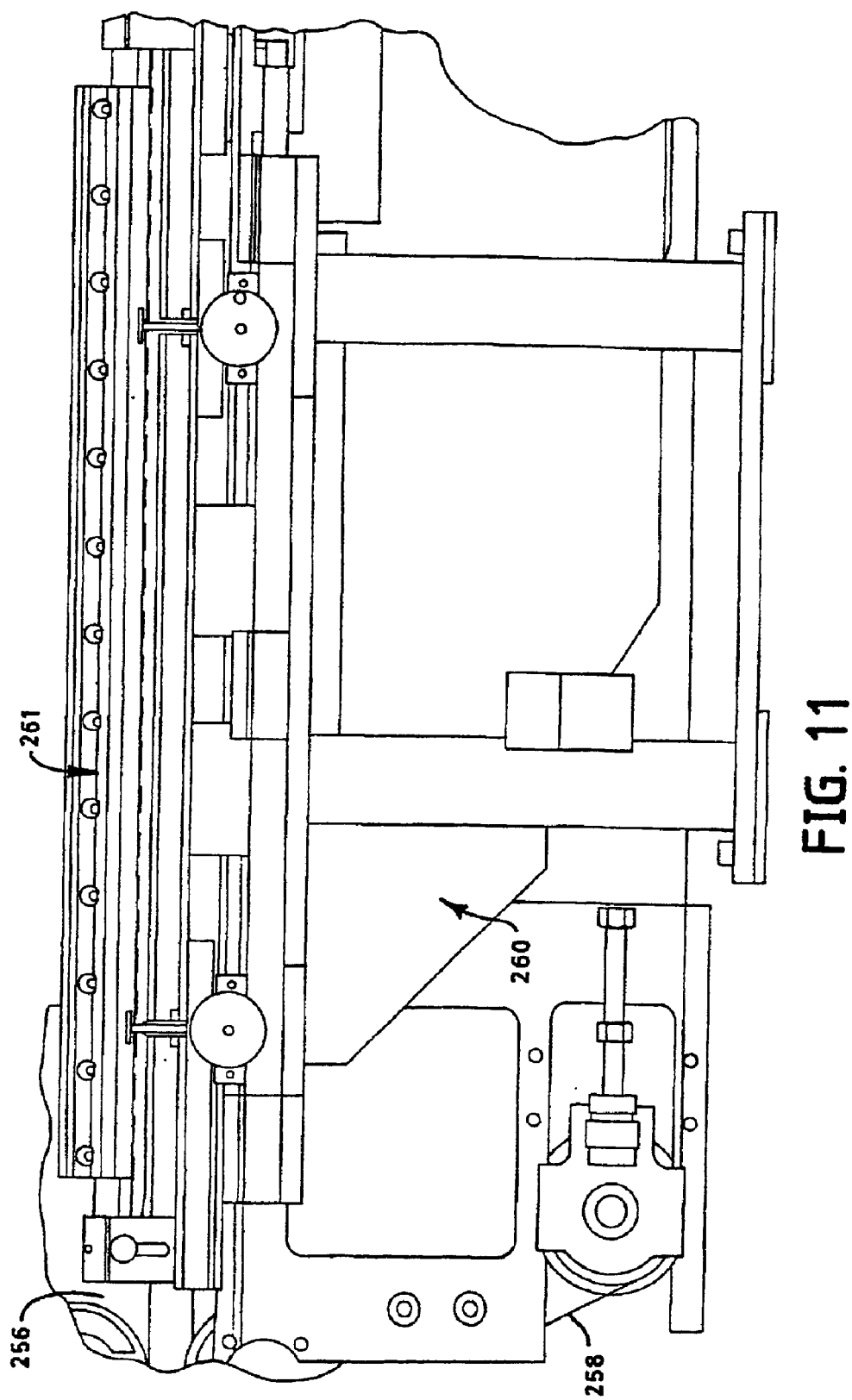
FIG. 11 is an enlarged side elevation of an internal panel positioning station of the seaming section of FIG. 6.
Figure 12:
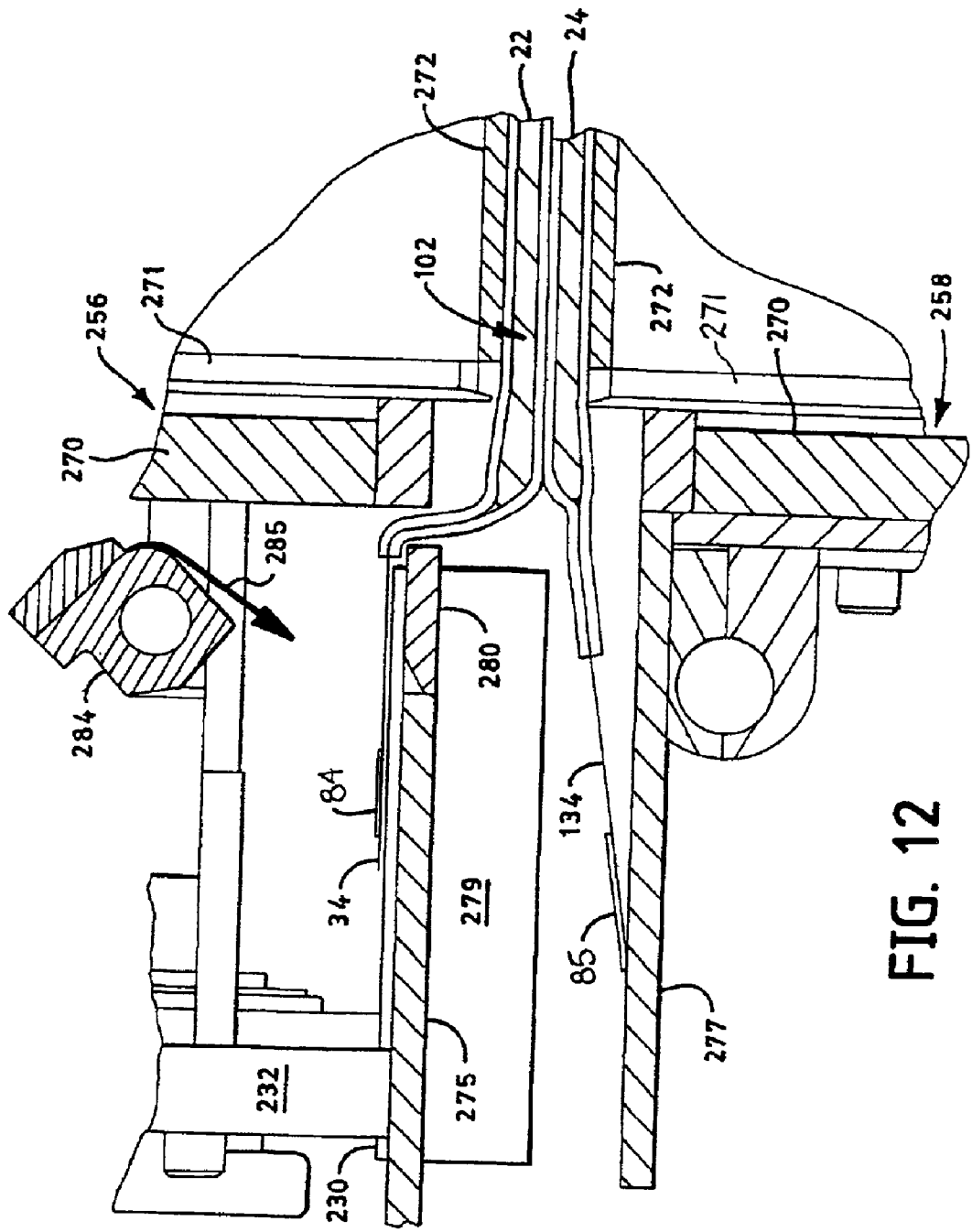
FIGS. 12–14 are enlarged section views of a portion of a pair of training pants at sequential positions within the seaming section of FIG. 11.

Formation of the side panel engagement seam 88 will now be described in greater detail with particular reference to FIGS. 11–19. FIG. 11 separately illustrates the interior panel positioning station 260 of the seaming section 250, where an interior panel positioning mechanism 261 positions the front side panels 34 on each side of the training pants 102 to form the interior side panel of the engagement seam 88. FIGS. 12–14 are section views of a portion of a pair of training pants 102 at a series of continually advancing positions within the interior panel positioning station 260. FIGS. 6 and 15 illustrate the exterior panel positioning station 262 of the seaming section 250, where an exterior panel positioning mechanism 263 positions the back side panels 134 on each side of the training pants 102 to form the exterior side panel of the engagement seam 88. In the illustrated embodiment, the front side panels 34 carrying the second fastening components 84 form the interior side panels of the engagement seam 88, and the back side panels 134 carrying the first fastening components 82 form the exterior side panels of the engagement seam. FIGS. 16-19 illustrate section views of a pair of training pants 102 at a series of continually advancing positions within the exterior panel positioning station 262. The description will focus on the formation of the engagement seam 88 and bonding the side panels 34, 134 together on one side of the training pants 102, it being understood that an engagement seam is also formed on the other side of the training pants in a similar manner. The engagement seams 88 can be formed simultaneously or sequentially on the right and left sides of the pants 102.

FIG. 12 illustrates the training pants 102 positioned between the upper and lower alignment conveyors 256 and 258 at a location downstream from the location illustrated in FIG. 10. Each alignment conveyor 256 and 258 comprises a frame structure 270, a plurality of rotatable pulleys 271 supported by the frame structure, and a continuous belt 272 carried by the pulleys. A drive system and conveyor shaft (not shown) can be used to rotatively drive one or more of the pulleys 271. The alignment conveyors 256 and 258 can comprise vacuum conveyors or other suitable transport devices.

At the location illustrated in FIG. 12, the front side panel 34 is disposed on or in close proximity to an upper skid plate 275 and the back Bide panel 134 is disposed on or in close proximity to a lower skid plate 277. The skid plates support the side panels 34, 134 and maintain separation between the side panels for subsequent folding operations. The front side panel 34 is transitioned onto the upper skid plate 275 with a ramp section 279 of the separation plate 230, or by other suitable means. The upper skid plate 275 and the separation plate 230 can be rigidly bonded together or integrally formed. The upper skid plate 275 can also be rigidly mounted on the upper alignment conveyor 256 or other suitable structure by support members 232 such as brackets or the like. The lower skid plate 277 can be rigidly mounted on the lower alignment conveyor 258 or other suitable member by any suitable means. The skid plates 275, 277 can be formed of the same materials as the separation plates 230.

As illustrated in FIG. 12, the front side panel 34 can also be supported in part by an interior support member 280. The interior support member 280 can comprise an integral portion of the upper skid plate 275, or it may be formed separately therefrom disposed on or bonded to the upper skid plate, such as by mechanical fasteners, welding, adhesives, or the like. As described in greater detail below, the interior support member 280 can comprise a cap of an air knife used in positioning the front side panel 34.

One or both of the side panels 34,134 can be smoothed out or straightened if desired by various means including fluid stabilizing devices. For example, as shown in FIG. 12, an air knife 284, air bar, air nozzle or the like can be mounted above the front side panel 34 to provide a stream of fluid generally in the direction of arrow 285 to stabilize and/or straighten the front side panel against the upper skid plate 275. A fluid stabilizing device (not shown) can also be mounted on the interior support member 280 to stabilize and/or straighten the back side panels 134. In an alternative embodiment, the folding conveyors 206 and 208 and/or the alignment conveyors 256 and 258 can incorporate fluid stabilizing devices consisting of fluid manifolds (not shown) operatively connected to a high pressure fluid source to fluidly shake the side panels. Suitable mechanisms for smoothing and straightening the side panels 34 and 134 are disclosed in U.S. Pat. No. 5,046,272 issued Sep. 10, 1991 to Vogt et al., which is incorporated herein by reference. The terms air and fluid are used interchangeably herein to refer to any gaseous substance, for example, air at ambient temperature. Where the specific application permits, the term "fluid" also includes any liquid medium.

FIG. 13 illustrates the training pants 102 between the upper and lower alignment conveyors 256 and 258 at a location downstream of the location illustrated in FIG. 12. In FIG. 13, the back side panel 134 has been transferred from the lower skid plate 277 to a lower air knife 290. The lower air knife 290 can further control and guide the position of the back side panel 134 in preparation for subsequent operations. At the location illustrated in FIG. 13, the front side panel 34 can continue to reside on or remain in close proximity to the upper skid plate 275 and the interior support member 280.

The lower air knife 290 of the illustrated embodiment comprises an air plenum 291 and a cap 292 attached to the plenum with suitable fasteners (not shown). The plenum 291 and the cap 292 are spaced apart slightly to form a thin nozzle 294 therebetween. The plenum 291 can define an internal chamber 295 and channels (not shown) which provide fluid communication between the internal chamber and the nozzle 294. The air knife 290 can also comprise a port (not shown) which provides fluid communication between the internal chamber 295 and a source of pressurized air (not shown). The port can be located at one end of the air knife 290 or at one or more other locations along the length of the air knife. The length of the lower air knife 290 can be oriented generally parallel to the machine direction 108 (which extends generally into the page in FIG. 13), with the nozzle 294 extending over substantially the full length of the air knife. The air knife 290 can have any desired length, such as in the range of about 0.1 to about 1 meter, and more preferably about 0.6 to about 0.7 meters.

As viewed in FIG. 13, the nozzle 294 expels air toward the back side panel 134 generally parallel to the plane formed at the interface between the plenum 291 and the cap 292. For purposes of the present application, the direction air is expelled from the nozzle 294 at the moment when the air knife is activated will be referred to as the nozzle flow direction. The nozzle flow direction is generally toward the upper left of FIG. 13.

The lower air knife 290 further comprises a surface 296 adjacent to and extending laterally outward from the nozzle 294, which surface will be referred to further herein as a Coanda surface. The Coanda surface 296 is the surface that the air from the nozzle 294 will follow under normal operating conditions. In the illustrated embodiment, the Coanda surface 296 is formed by a portion of the outer surface of the plenum 291 which extends beyond the cap 292. In this particular application, the Coanda surface 296 is curved relative to the nozzle flow direction. Specifically, the illustrated Coanda surface 296 in cross section is generally parallel to the nozzle flow direction at the nozzle 294 and gradually curves away from the nozzle and cap 292 to form a 90 degree curved portion 298. Further from the nozzle 294, the 90 degree curved portion 298 is followed by a generally planar portion 300. For purposes of the present invention, the Coanda surface 296 will be referred to as having a terminal edge 301, beyond which air from the nozzle 294 diverges and loses velocity. In the illustrated embodiment, the terminal edge 301 is a 90 degree edge of the outer surface of the air knife 290.

The Coanda surface 296 in cross section defines a curvature from the nozzle 294 to the terminal edge 301. The Coanda surface 296 desirably has a curvature of about 0 to about 180 degrees, and more desirably about 90 degrees to about 180 degrees. The curvature of the Coanda surface 296 can also represent the angle through which the resulting sheet of air bends relative to the nozzle flow direction. It is understood that the Coanda surface 296 can employ a variety of configurations beyond those specifically illustrated herein, such as a plurality of smaller curved portions separated by generally planar portions; larger or smaller radius curved portions; a generally planar portion between the nozzle and the initial curved portion; a completely curved surface; or the like. Moreover, the air knives described herein can employ integral or separate plena, caps and/or Coanda surfaces.

In operation, compressed air is delivered to the internal chamber 295 and expelled from the nozzle 294 in the form of a jet. Due to the nozzle 294 configuration, the jet generally forms a sheet of air which further entrains ambient air. Based on the Coanda effect, which is sometimes referred to as the wall-attachment principle, the presence of the Coanda surface 296 creates a pressure differential across the two sides of the air sheet, causing the sheet to attach to and follow the curved Coanda surface. Once the back side panel 134 passes beyond the downstream end of the lower skid plate 277, the back side panel is drawn toward the lower air knife 290 by the laminar flow of the air sheet over the Coanda surface 296. The nozzle 294 is desirably but not necessarily located immediately beyond the downstream end of the lower skid plate 277. The air flow through the nozzle 294 can be adjusted to establish the desired position of the side panel 134. For the illustrated embodiment, the air flow need not draw the side panel 134 fully parallel to the generally planar portion 300.

The lower air knife 290 can be formed from stainless steel, aluminum, or other suitable materials. Typical operating ranges for the air supply source are about 1.4 to about 6.9 bars (20–100 pounds per square inch) with air consumption of about 37 to about 116 standard liters per minute (SLPM) (1.3–4.1 standard cubic feet per minute) per 25 millimeter length of nozzle. For example, the air supply pressure can be 2.8 bars (40 psi) with air consumption of about 57 SLPM (2 SCFM). The aperture of the nozzle 294 can be adjusted with shims (not shown) to obtain the desired air velocity. In one particular embodiment, the nozzle 294 opening is about 0.05 millimeters (0.002 inch). As an alternative to a continuous nozzle opening, the nozzle 294 can comprise a different configuration such as a large number of individual, closely spaced apertures. Suitable air knives 290 are available from various commercial vendors, such as ITW Vortec, or EXAIR Corporation, both of Cincinnati, Ohio, U.S.A.

FIG. 14 illustrates the pair of training pants 102 between the upper and lower alignment conveyors 256 and 258 at a location downstream from the location illustrated in FIG. 13. The back side panel 134 generally can remain in the position established previously by the lower air knife 290. With the side panels 34, 134 sufficiently separated, the front side panel can be folded inward to form the interior panel of the engagement seam 88. As shown in FIG. 14, the front side panel 34 has been transferred from the upper skid plate 275 into operative proximity with an upper air knife 310.

Figure 20:
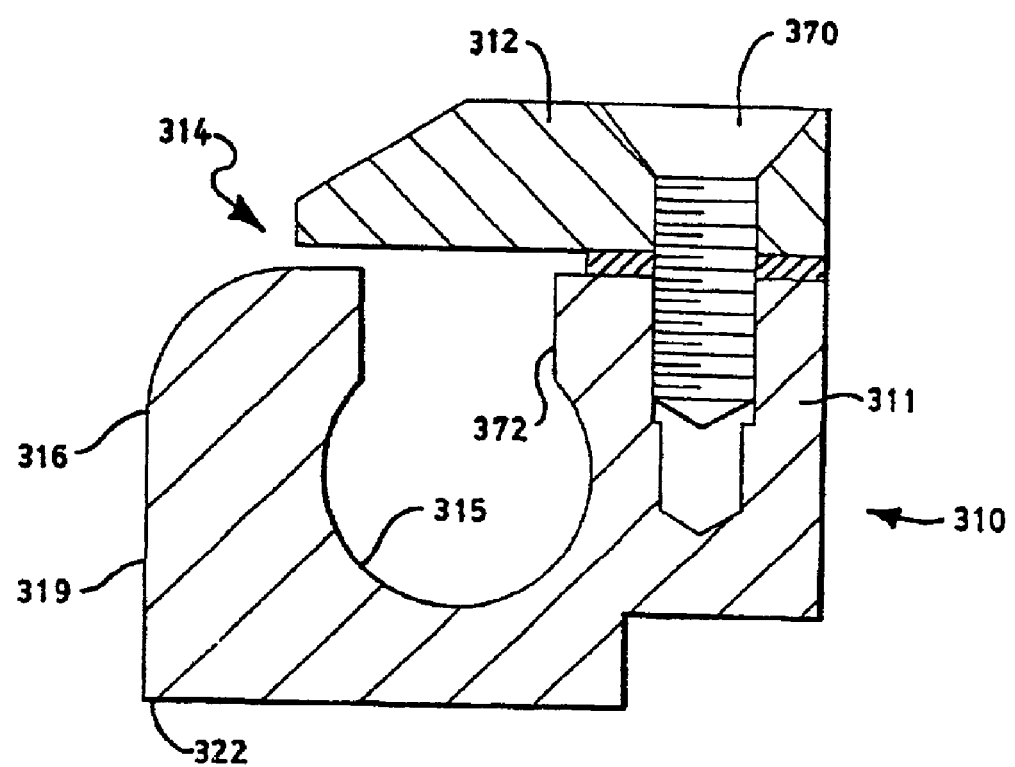
FIG. 20 is an enlarged section view of an air knife of the seaming section as shown in FIG. 14.

The upper air knife 310 can be constructed of the same materials and can operate in the same general manner as the lower air knife 290. The upper air knives 310 can be mounted on opposite sides of the alignment conveyors 256 and 258 and hence on opposite sides of the machine center line at fixed locations in the machine direction. The upper air knives 310 can but need not necessarily be aligned generally parallel to the machine center line such that a nozzle flow direction is generally perpendicular to the machine direction. With additional reference to FIG. 20 which shows an enlarged section view of the upper air knife 310, the upper air knife 310 can comprise an air plenum 311 and a cap 312 attached to the plenum with suitable fasteners 370. The plenum 311 and the cap 312 form a thin nozzle 314 therebetween. The plenum 311 defines an internal chamber 315 and channels 372 which provide fluid communication between the internal chamber and the nozzle 314. A port (not shown) provides fluid communication between the internal chamber 315 and a source of pressurized air (not shown). The length of the upper air knife 310 can be oriented in the machine direction 108, (e.g., into the page in FIG. 14) although rotated relative to the angular position of the lower air knife 290 such that the nozzle flow direction of the upper air knife is generally horizontal. The nozzle flow direction of the upper air knife 310 of the illustrated embodiment is toward the left-hand side of FIGS. 14 and 20. The upper air knife 310 can be mounted on the support members 232 in a cantilevered configuration, so that the side panels 34, 134 can pass the downstream end of the upper air knife after the fastening components 82, 84 are engaged along the engagement seam 88.

The upper air knife 310 can comprise a Coanda surface 316 that is adjacent to and extends laterally outward of the nozzle 314. In the illustrated embodiment, the Coanda surface 316 is formed by a portion of the outer surface of the plenum 311 which extends beyond the cap 312. The Coanda surface 316 is curved relative to the nozzle flow direction. Specifically, the illustrated Coanda surface 316 in cross section is generally parallel to the nozzle flow direction at the nozzle 314, and gradually curves away from the nozzle and cap 312 to form a curved portion 318. Thereafter, the Coanda surface 316 can include a generally planar portion 319 followed by a terminal edge 322, which can be a 90 degree edge of the outer surface of the air knife beyond which air from the nozzle diverges. The curved portion 318 preferably has an angle in the range of about 0 to about 270 degrees, more preferably about 0 to about 90 degrees, and still more preferably about 90 degrees. The generally planar portion 319 can be less curved than the curved portion 318, and is desirably flat.

The Coanda surface 316 in cross section defines a curvature from the nozzle 314 to the terminal edge 322 of greater than 0 degrees, for example from greater than 0 to about 270 degrees, particularly about 20 degrees or greater, more particularly about 30 degrees or greater, more particularly about 45 degrees or greater, more particularly about 60 degrees or greater, more particularly about 80 degrees or greater, more particularly about 90 degrees or greater, such as about 90 to about 270 degrees, more particularly about 135 degrees or greater, such as about 135 to about 225 degrees, and in particular embodiments about 180 degrees. The curvature of the Coanda surface 316 can also represent the angle that the resulting sheet of air bends relative to the nozzle flow direction. The Coanda surface 316 can employ a variety of configurations. In this particular embodiment, the cap 312 of the upper air knife 310 extends upstream beyond the nozzle 314 to form the interior support member 280 (FIGS. 12 and 13).

In operation, compressed air is delivered to the internal chamber 315 and expelled from the nozzle 314. The resulting air jet forms an air sheet that further entrains ambient air and becomes attached to the Coanda surface 316 due to the Coanda effect. Once the front side panel 34 passes downstream from the upper skid plate 275, the front side panel is drawn toward the upper air knife 310 by the laminar flow of the air sheet over the Coanda surface 316. A supplemental air nozzle (not shown) may also be employed to ensure that the front side panel 34 is in close proximity to the air knife 310. Sufficient air can be supplied to the nozzle 314 so that the resulting air sheet follows the curvature of the Coanda surface through the curved portion 318 and the generally planar region 319. The air sheet dissipates beginning at the terminal edge 322. In this manner, the air sheet from the upper air knife 310 passes through an angle of about 180 degrees. The nozzle 314 is desirably but not necessarily located immediately downstream from the upper skid plate 275. The upper air knife 310 can be operated at the same or different air flow rates as the lower air knife 290.

As best shown in FIG. 14, the size and position of the upper air knife 310 is selected so that the second fastening component 84 is centered on the generally planar portion 319 of the upper air knife, for example in a vertical orientation. This generally planar portion 319 can subsequently provide a flat surface for engagement of the fastening components 82, 84. Thus, at this point in the process, the folded training pants 102 can be transported downstream in the machine direction 108 with the front side panels 34 curved downward to a flat and stable position around the upper air knives 310. Due to the air stream expelled by the upper air knives 310, the front side panels can be supported on a cushion of air provided on the surfaces 316 of the air knives. Desirably, the cushion of air minimizes drag and skewing of the side panels as they are transported in the machine direction.

Use of the terms "vertical" and "horizontal" herein and variations thereof have their usual meaning, however, the present invention contemplates that vertical surfaces can be "generally vertically" disposed if desired and would thus be oriented between the true vertical position and about a 45 degree position relative to the true vertical position. The same interpretation for "generally horizontally" disposed means an orientation between the true horizontal and about a 45 degree position relative thereto. The terms "upper" and "lower" are provided for ease of understanding, and it should be recognized that the spatial arrangement of the elements being described could be inverted or arranged in another manner, such as side-by-side.

FIGS. 16–19 illustrate the pair of training pants 102 between the upper and lower alignment conveyors 256 and 258 at a series of locations downstream of the location illustrated in FIG. 14. The locations illustrated in FIGS. 16–19 are within the exterior panel positioning station 262 (FIG. 15), where the exterior panel positioning mechanism 263 guides the back side panel 134 into aligned, overlapping orientation with the front side panel 34. The exterior panel positioning mechanism 263 can comprise any suitable device for moving the back side panels 134 into the desired overlapping orientation, including but not limited to folding boards, folding skis, paddles, fingers, vacuum devices, air blasts, mechanical devices with reciprocating motion such as tuckers, four-bar linkages, slide-crank mechanisms, or the like and combinations thereof. In the illustrated embodiment, as the back side panel 134 is transported in the machine direction 108, a panel folding mechanism comprising a panel folding head 340 is reciprocated into and out of the plane formed between the alignment conveyors 256 and 258 to intersect the path of travel of the back side panel 134 and move the back side panel into overlapping (e.g., opposed) relationship with the front side panel 34. In the illustrated embodiment, beginning with FIG. 16, the panel folding head 340 moves vertically into contact with the back side panel 134. The panel folding head 340 can continue to move upward and push the back side panel 134 farther upward.

The exterior panel positioning station 262 also includes a separator panel 330 (FIGS. 6 and 15–19) to maintain the established shape and position of the front side panel 34 during positioning of the back side panel 134. The separator panel 330 can alternatively or additionally form a folding edge 332 (FIG. 16) to facilitate positioning of the back side panel 134. The illustrated separator panel 330 comprises a body portion 334 and an elongated finger portion 336. The body portion 334 and finger portion 336 can be connected near the upstream end of the separator panel 330, with the finger portion projecting downstream in a cantilevered orientation (FIG. 15). A slot 338 is formed between the body portion 334 and the cantilevered finger portion 336.

Figure 17:
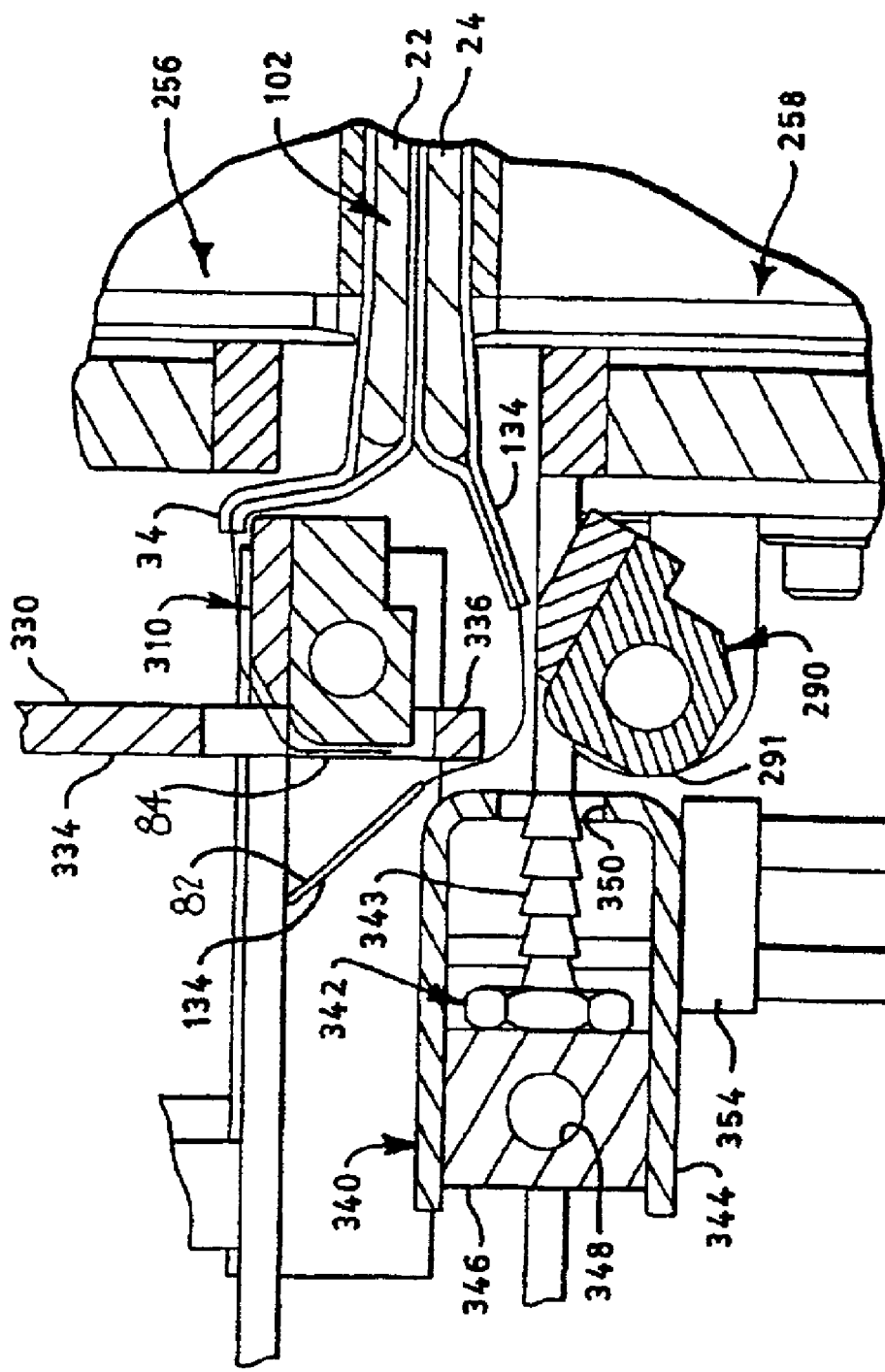
Figure 18:
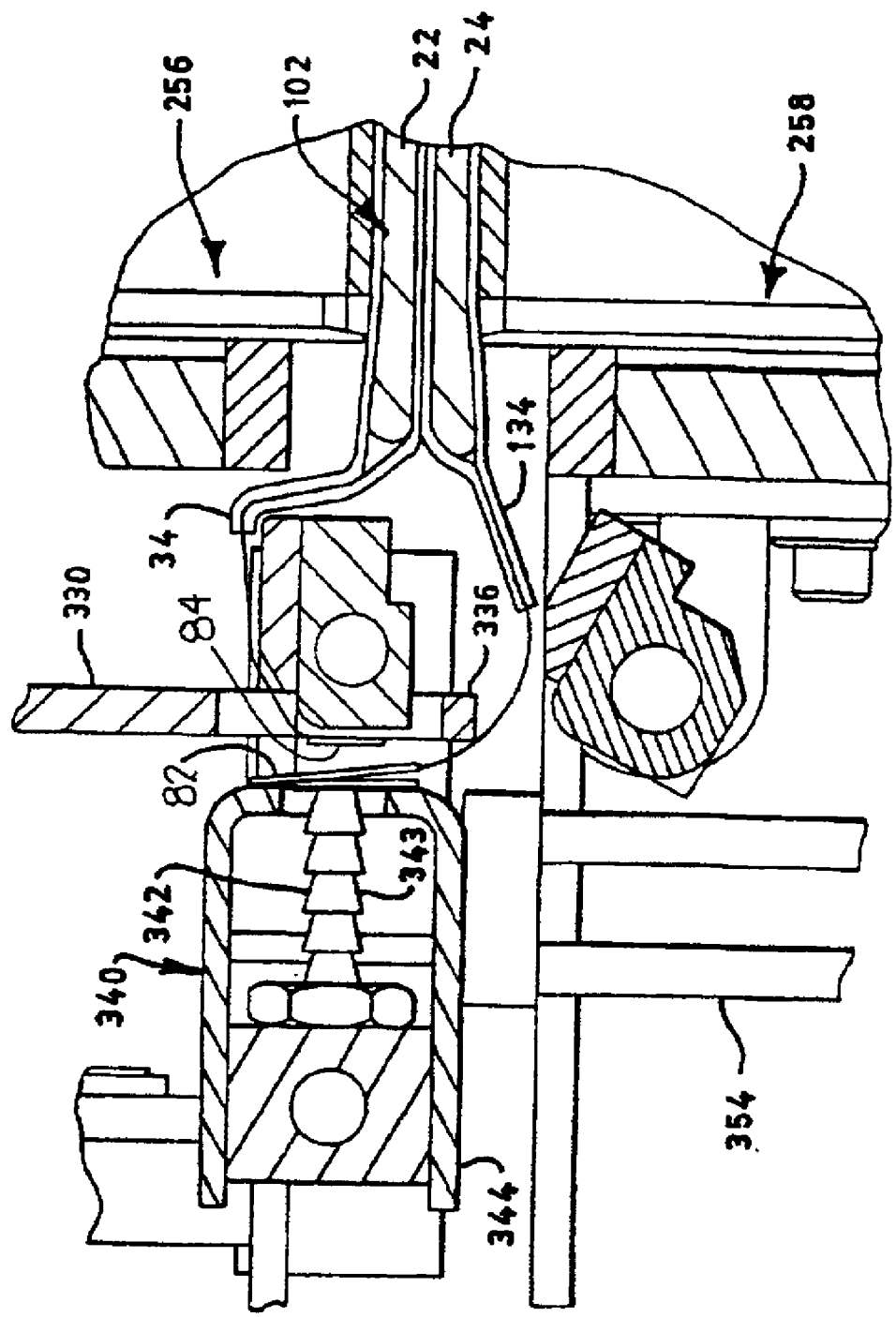
Figure 19:
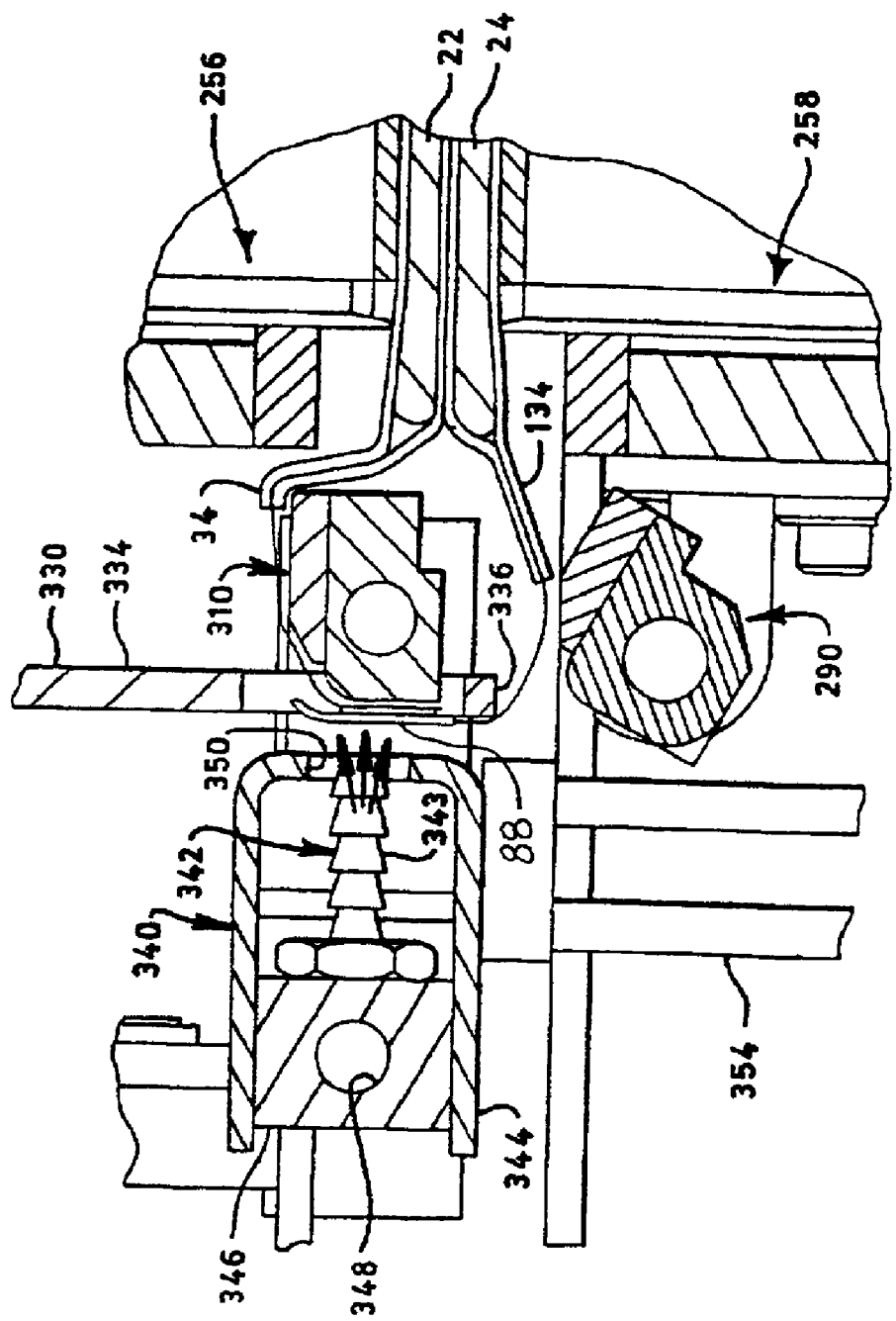

The separator panel body portion 334 can be mounted to the upper alignment conveyor 256 or other suitable frame structure. The separator panel 330 can be spaced outward from the upper alignment conveyor 256 at a transverse location generally corresponding to the location of the generally planar surface 319 of the upper air knife 310. As shown in FIGS. 17–19, the finger portion 336 of the separator panel 330 is positioned so that the first fastening components 82 will overlap and subsequently engage the second fastening components 84 when the back side panel 134 is folded over the finger portion. The size of the slot 338 can be selected to allow room for the fastening components 82, 84 to be engaged in the region formed by the slot.

Figure 16:
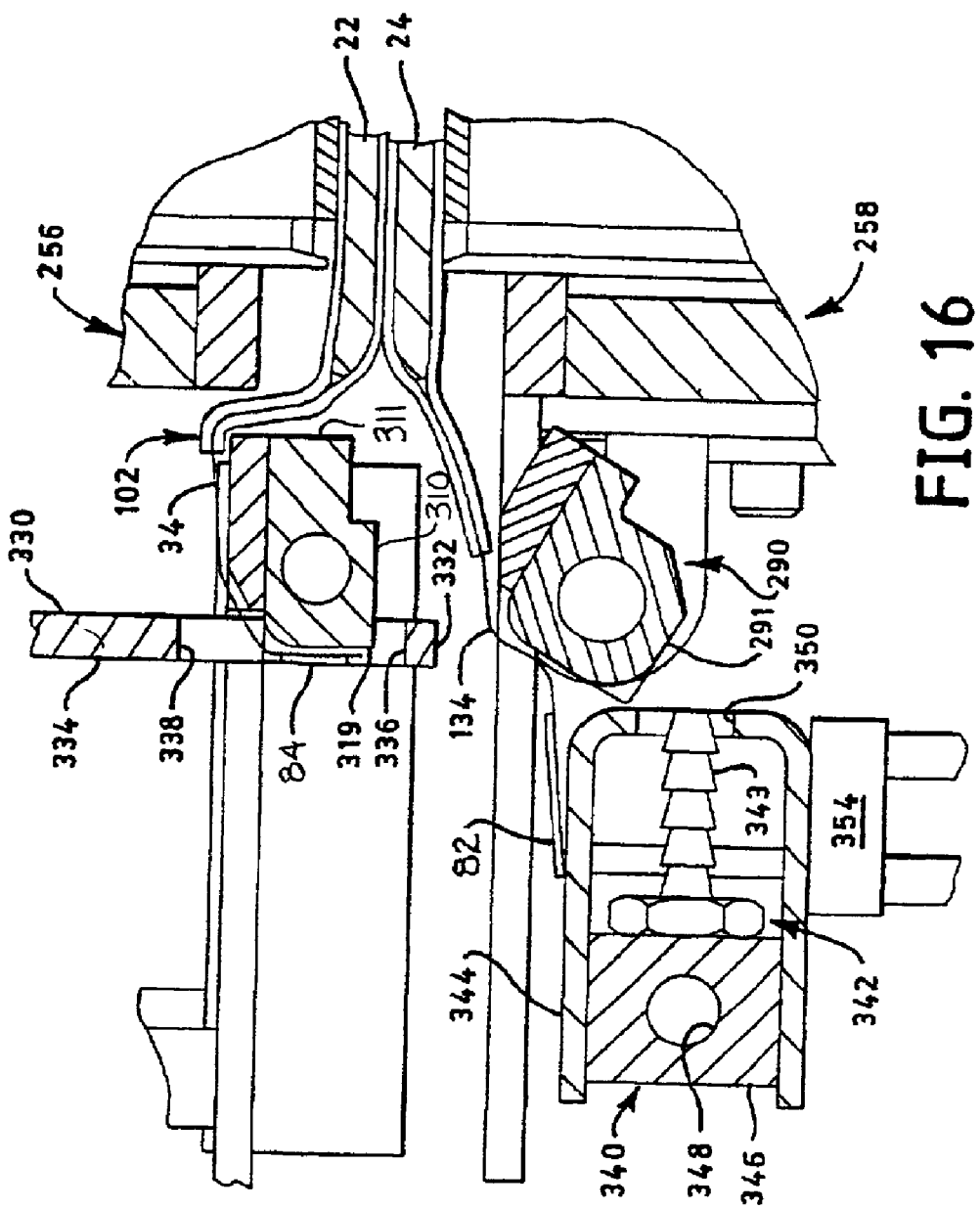
FIGS. 16–19 are enlarged section views of a portion of a pair of training pants at sequential positions within the exterior panel positioning station of FIG. 15.

The lower air knife 290 can be positioned or controlled so that air from the lower air knife nozzle 294 does not interfere with or deflect off the panel folding head 340 beginning at about the location illustrated in FIG. 16. The plenum 291 of the lower air knife 290 can be chamfered if necessary so as not to interfere with movement of the panel folding head 340. The front side panel 34 can remain in the position established previously by the upper air knife 310 during the sequence illustrated in FIGS. 16–19.

Once the back side panel 134 overlaps the front side panel 34 in opposed relationship therewith as illustrated in FIG. 18, a fastener engagement mechanism 342 urges the first and second fastening components 82 and 84 to engage one another along the engagement seam 88. As illustrated in FIGS. 16 and 19, the fastener engagement mechanism 342 can comprise one or more air nozzles 343 that exhaust air in the direction of the arrows to blow (see flow arrows in FIG. 19) the first fastening component 82 of the back side panel 134 into engagement with the second fastening component 84 of the front side panel 34. Alternatively, the panel folding head 340 can function as the fastener engagement mechanism 342. For example, the panel folding head 340 can be positioned so that movement of the panel folding head causes the first fastening component 82 to engage the second fastening component 84. In one embodiment, the panel folding head 340 can provide initial contact between the fastening components and the air nozzles 343 can provide more secure attachment of the fastening components 82, 84. Alternatively, the fastener engagement mechanism 342 can comprise an air knife or air bar, rollers, vacuum wheels, magnets, a funnel or disc folding device, a folding board, a blade on a shaft, an air cylinder, or the like. The side panels 34, 134 pass the downstream end of the upper air knife 310 and the separator panel finger portion 336 after the fastening components 82, 84 are engaged.

With reference to FIGS. 16 and 19, the panel folding head 340 can comprise a cover 344 with the fastener engagement mechanism 342 mounted within the cover. The cover 344 desirably has a length measured in the machine direction 108 that is the same or slightly greater than the machine direction length of the back side panel 134, particularly adjacent the distal edges 68. The fastener engagement mechanism 342 comprises a manifold block 346, an internal chamber 348, a plurality of air nozzles 343, a port for connecting the internal chamber to a source of pressurized air (not shown), and channels (not shown) within the manifold block providing fluid communication between the internal chamber and the air nozzles. The cover 344 has one or more apertures 350 for the air nozzles 343. In one particular embodiment, the fastener engagement mechanism 342 comprises five air nozzles 343 which expel air through a slot 350 in the cover 344. This configuration desirably allows the entire first fastening component 82 to move in step-wise fashion into engagement with the second fastening component 84. The cover 344 can be formed of any suitable material such as stainless steel, or the like.

Figure 21:
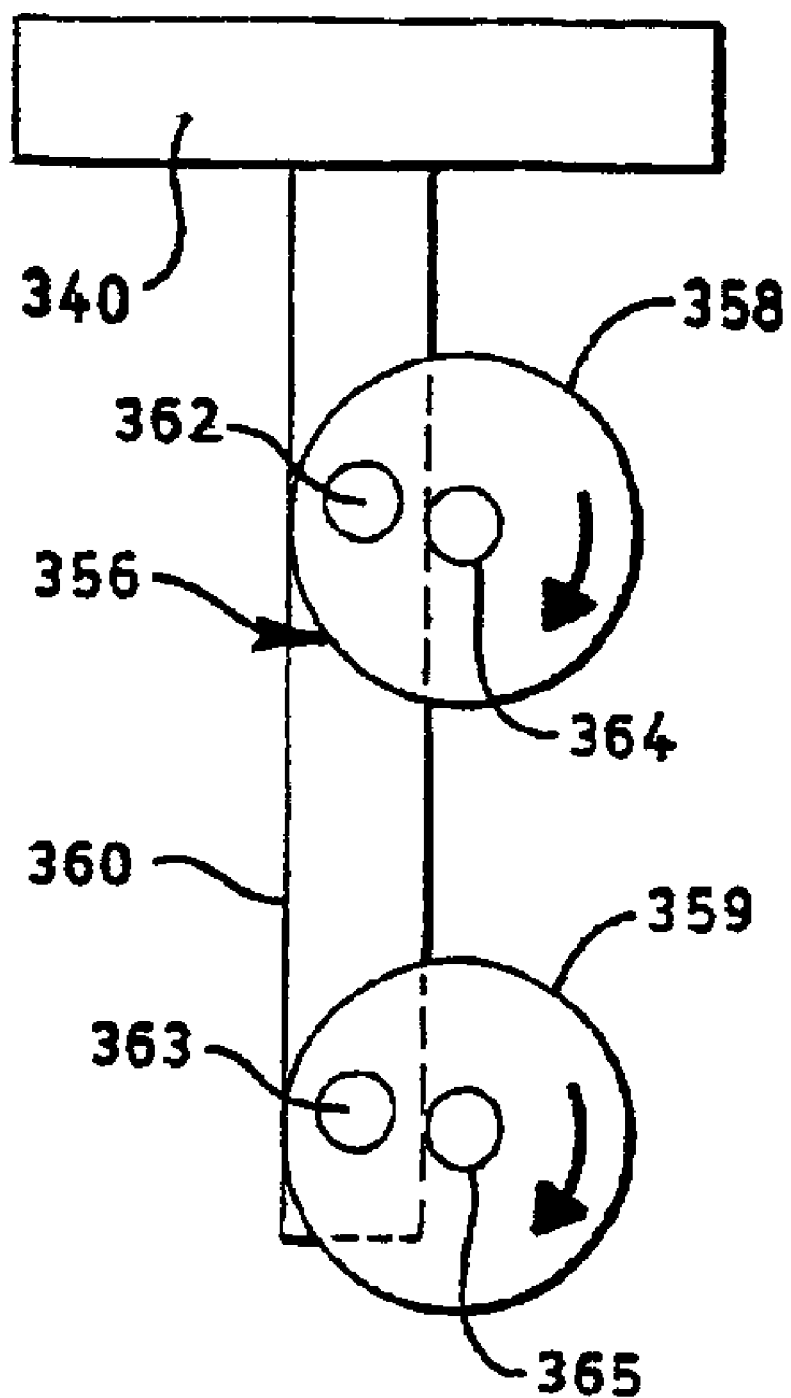
FIG. 21 is a schematic side view of an orbital motion device of the apparatus.

The panel folding head 340 is mounted on a suitable support structure 354. The support structure 354 can comprise a rigid connection, such as one or more brackets, or a moveable connection that permits movement of the panel folding head for access to various components, such as a piston and cylinder combination, slideable brackets, or the like. With reference to FIGS. 15 and 21, the panel folding head 340 can be connected either directly or indirectly to a suitable drive mechanism 356 for moving the panel folding head so that the back side panel 134 overlaps the front side panel 34. The drive mechanism 356 can comprise, for example, a four-bar linkage system as illustrated, including a pair of vertically-stacked rotatable discs 358 and 359, a connecting rod 360 rotatably mounted at single points 362 and 363 to each of the discs, rotational drive shafts 364 and 365, and a motor (not shown) for rotating the drive shafts and discs.

The timing and rotation of the drive mechanism 356 can desirably be controlled to provide one complete cycle of the panel folding head 340 for the training pants 102. This creates repeatable points of contact between the back side panel 134 and the cover 344. As the pair of training pants 102 travels in the machine direction 108 with the back side panel 134 outstretched, the top surface of the cover 344 makes uniform contact on the underside of the back side panel. Due to the orbital travel of the panel folding head 340, it can not only lift the back side panel, but can also carry it in the machine direction 108. The cover 344 can be coated, such as with an aluminum-manganese composite or the like, to provide a positive gripping surface on the back side panel 134 while the side panel is carried into opposed, overlapping alignment with the front side panel 34. The drive mechanism 356 can be configured so that, as the panel folding head achieves its maximum vertical position (e.g., FIGS. 18 and 19), the horizontal machine direction speed approximates the machine direction speed of the training pants 102. Other arrangements for panel folding are disclosed in Published U.S. patent application No. US2002-0007773 filed on May 15, 2001 by L. C. Hietpas et al. and titled "Orbital Motion Device For Seaming Garments," the entire disclosure of which is incorporated herein by reference. Alternative drive mechanisms 356 can include a stepper motor, a lineshaft drive, or the like.

Figure 22:
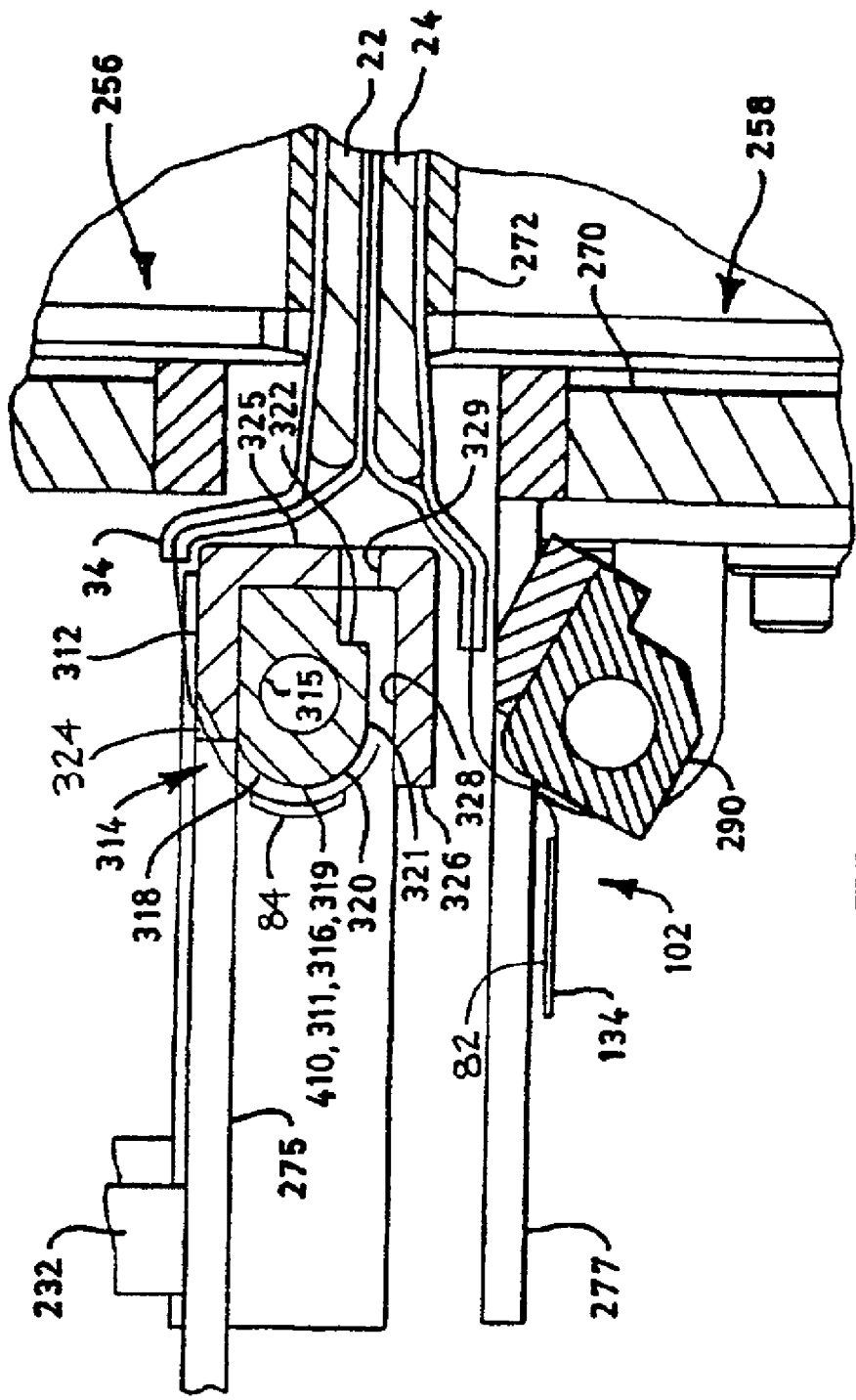
FIGS. 22 and 23 are enlarged section views of a portion of a pair of training pants at sequential positions within an alternative interior panel positioning station of the apparatus.
Figure 23:
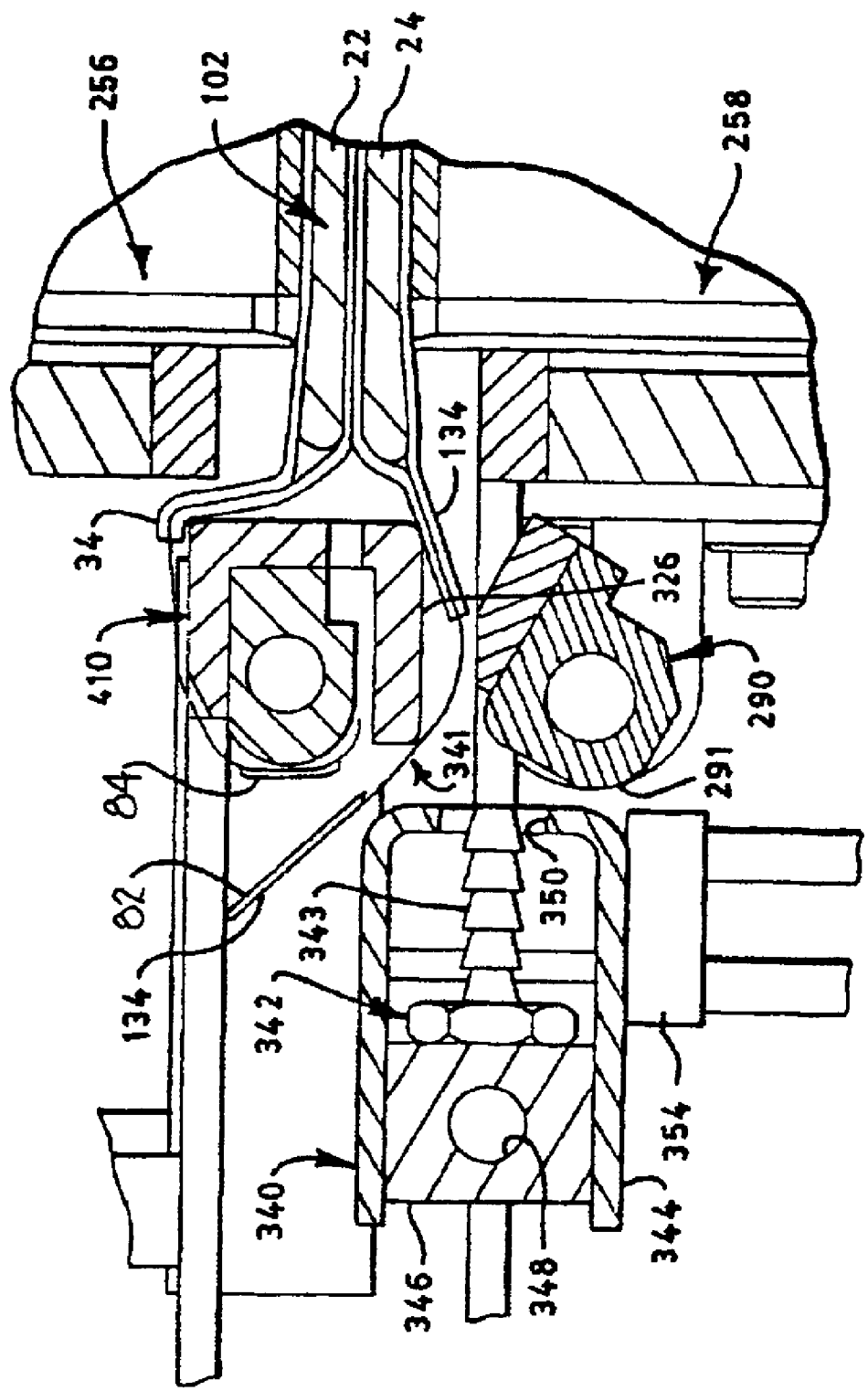

An alternative configuration of an upper air knife 410 is illustrated in FIGS. 22 and 23. The location of FIGS. 22 and 23 within the interior panel positioning station 260 corresponds generally to FIGS. 14 and 17. The illustrated upper air knife 410 comprises a plenum 311 defining an internal chamber 315, a cap 312 attached to the plenum and defining a nozzle 314 therebetween, and a Coanda surface 316 adjacent to and extending laterally outward from the nozzle. The Coanda surface 316 is curved relative to the nozzle flow direction. Specifically, the illustrated Coanda surface 316 in cross section is generally parallel to the nozzle flow direction at the nozzle 314, and gradually curves away from the nozzle and cap 312 to form a first curved portion 318. Thereafter, the Coanda surface 316 includes a first generally planar portion 319, followed by a second curved portion 320, followed by a second generally planar portion 321. The Coanda surface 316 has a terminal edge 322, which can be a 90 degree edge of the outer surface of the air knife beyond which air from the nozzle diverges. The individual curved portions 318 and 320 can have angles from 0 to about 180 degrees, more preferably from about 0 to about 90 degrees, and more preferably about 90 degrees. The generally planar portions 319 and 321 are less curved than either of the curved portions, and are desirably flat surfaces.

The Coanda surface 316 in cross section defines a curvature from the nozzle 314 to the terminal edge 322 of greater than about 0 degrees, for example from greater than 0 to about 270 degrees, particularly about 20 degrees or greater, more particularly about 30 degrees or greater, more particularly about 45 degrees or greater, more particularly about 60 degrees or greater, more particularly about 80 degrees or greater, more particularly about 90 degrees or greater, such as about 90 to about 270 degrees, more particularly about 135 degrees or greater, such as about 135 to about 225 degrees, and in particular embodiments about 180 degrees. The Coanda surface 316 can employ a variety of configurations.

In this particular embodiment, the cap 312 can be constructed to have a C-shaped cross section including a first flange 324, a second flange 326 and an intermediate member 325 connecting the first and second flanges. The first flange 324 can be positioned in close proximity to the plenum 311 to define the nozzle 314 therebetween. The second flange 326 can be spaced from but positioned in close proximity to the plenum 311. For example, the second flange 326 can be spaced from the outer surface of the plenum 311 by from about 1 to about 10 millimeters, such as about 3.2 millimeters. Desirably, the second flange 326 can be positioned opposite the second generally planar portion 321 of the Coanda surface 316 to define therebetween an exhaust passage 328 for air. The intermediate member 325 can interconnect the first and second flanges 324 and 326 and define a plurality of apertures 329 which are open to and in fluid communication with the exhaust passage 328. These apertures 329 can be a variety of shapes and sizes which permit air to exhaust from the upper air knife 410. In one embodiment, the apertures 329 define a plurality of slots each having a length in the machine direction of about 5 centimeters. The flanges 324 and 326, and the intermediate member 325 if employed, can be integrally formed or can comprise separate structures bonded together.

In operation, compressed air is delivered to the internal chamber 315 and expelled from the nozzle 314. The resulting air jet forms a sheet of air which further entrains ambient air and becomes attached to the Coanda surface 316. The front side panel 34 is drawn toward the upper air knife 410 by the laminar flow of the air sheet over the Coanda surface 316. A supplemental air nozzle (not shown) can also be employed to ensure that the front side panel 34 is in close proximity to the air knife 410. Sufficient air is supplied to the nozzle 314 so that the resulting air sheet follows the curvature of the Coanda surface through the first curved portion 318, the first generally planar region 319, and the second curved portion 320. The air sheet enters the exhaust passage 328 and dissipates as it is directed through the apertures 329 and toward the composite structure 33 of the training pants 102. In this manner, the air sheet from the upper air knife 410 passes through an angle of about 180 degrees and does not affect the position of the back side panel 134. The nozzle 314 is desirably but not necessarily located immediately downstream from the upper skid plate 275. The upper air knife 410 can be operated at the same or different air flow rates as the lower air knife 290.

With reference to FIG. 23, the second flange 326 of the upper air knife 410 can define a folding edge 341. As the panel folding head 340 moves vertically into contact with the back side panel 134, the back side panel can contact folding edge 341 to facilitate panel folding.

Figure 24:
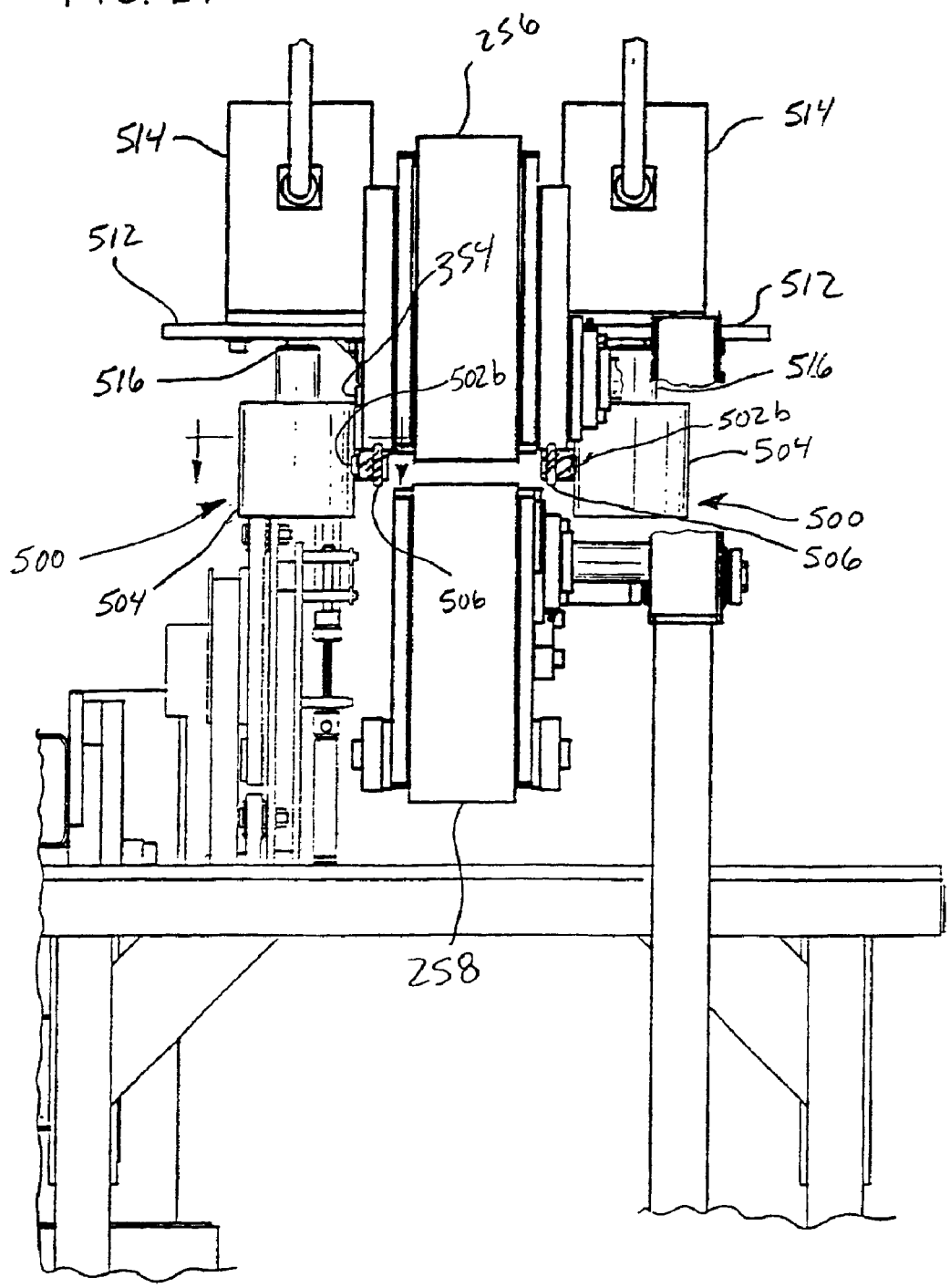
FIG. 24 is a rear fragmented elevation of the seaming section and nip assembly of FIG. 6.
Figure 25:
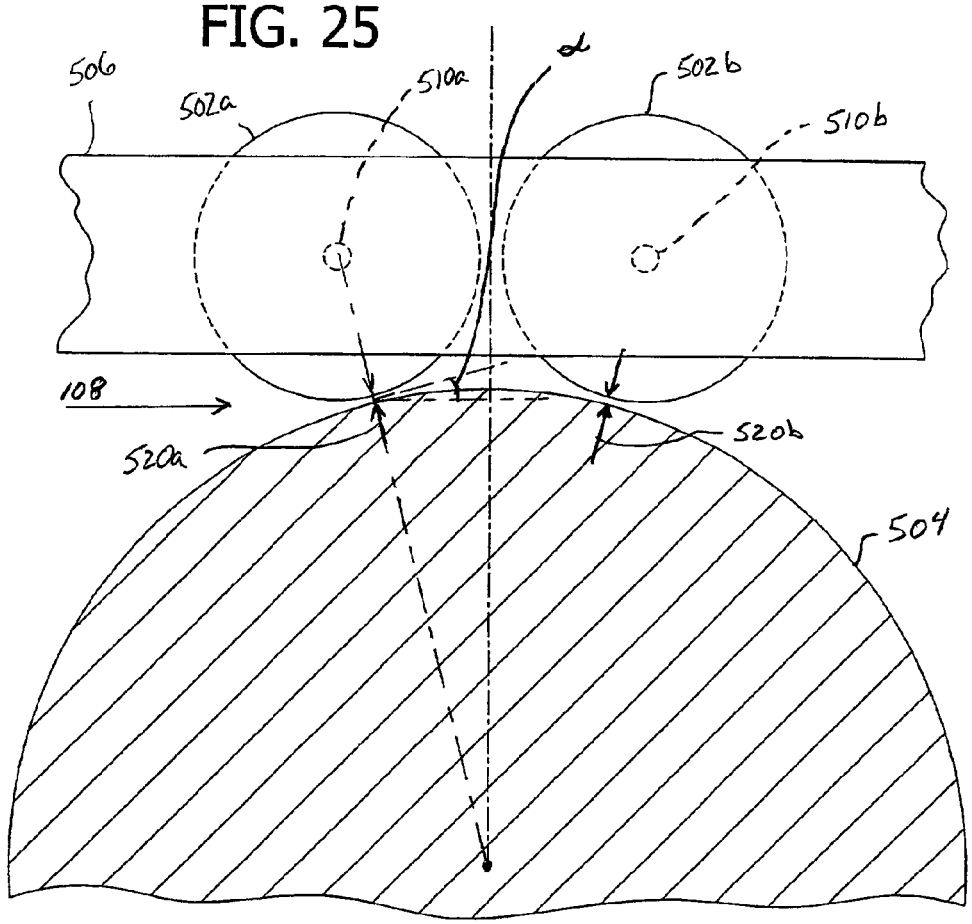
FIG. 25 is a fragmented and sectioned top view of a portion of the nip assembly.
Figure 27:
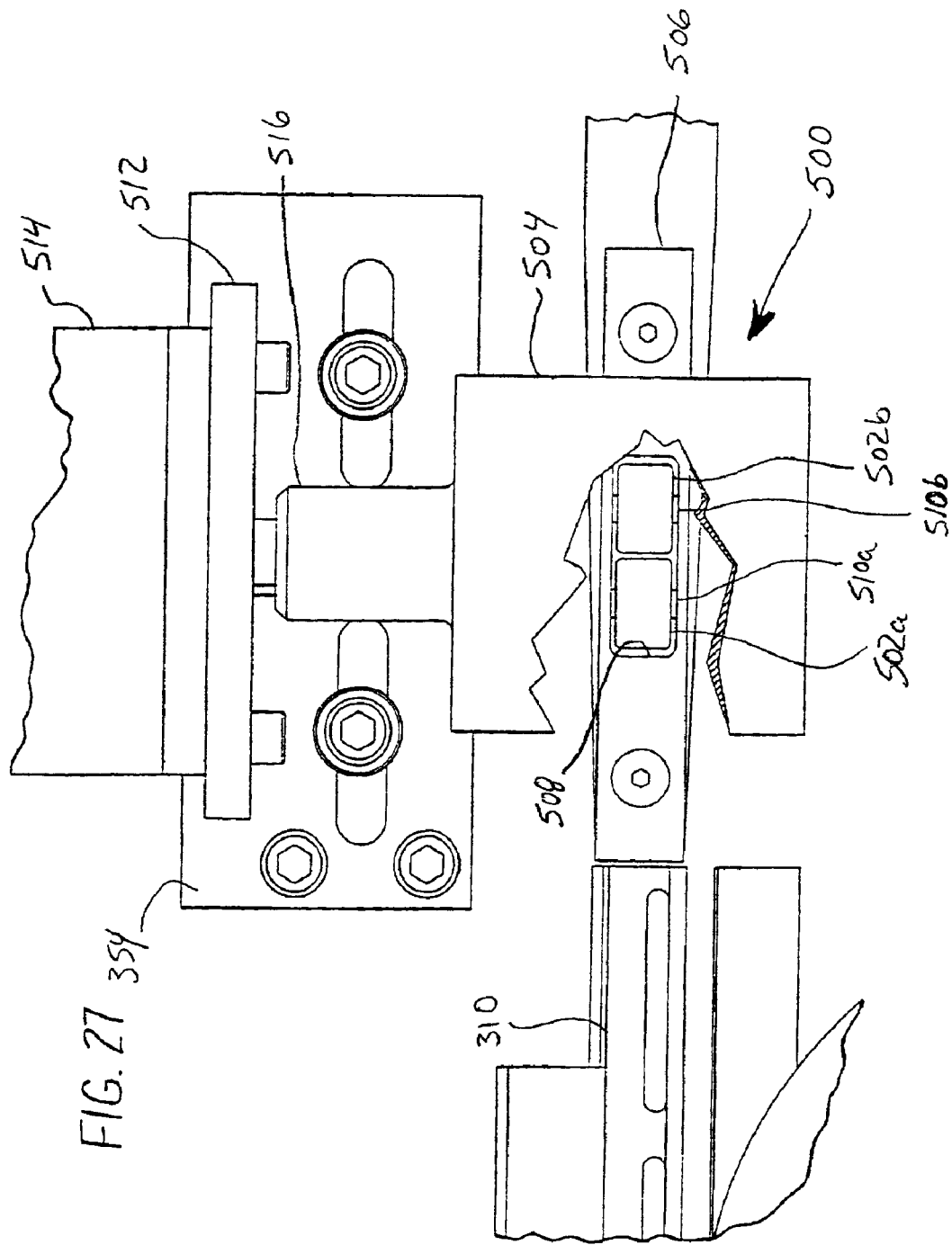
FIG. 27 is a fragmented exterior side elevation of the nip assembly.

In accordance with the present invention, nip assemblies, one of which is shown in FIGS. 6 and 15 and generally indicated at 500, are positioned downstream (e.g., in the machine direction 108) from the upper air knife 310. As shown in FIG. 24, the nip assemblies 500 are positioned laterally outward from the upper and lower conveyors 256, 258 for receiving the front and rear side panel fastening components 82, 84 generally along the engagement seams 88. For ease of illustration, construction and operation of the nip assemblies 500 will be described further herein with respect to only one such assembly, it being understood that the other nip assembly is constructed and operates in substantially the same manner. With particular reference to FIG. 25, each nip assembly 500 comprises a pair of non-driven rollers 502a, 502b and a driven roller 504 in close, generally transversely spaced relationship with the non-driven rollers. A mounting bracket 506 is cantilevered to the downstream end of the upper air knife 310 (FIG. 15) to extend longitudinally downstream therefrom generally in the machine direction 108 and has a central, generally rectangular opening 508 (FIG. 27). Two axles 510a, 510b extend vertically (e.g., normal to the machine direction 108) across the opening and are secured to the bracket, such as by being welded thereto, in longitudinally spaced relationship with each other. The non-driven rollers 502a, 502b are mounted on the axles 510a, 510b, respectively, for rotation thereon about rotation axes defined by the axles.

Figure 26:
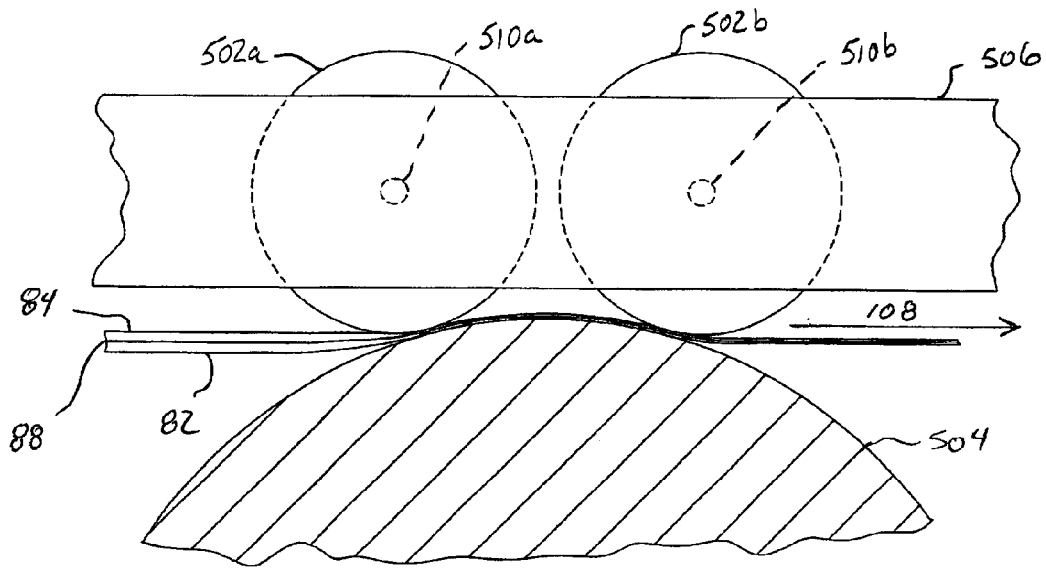
FIG. 26 is a view similar to FIG. 25 with fastening components of a pair of training pants passing through the nip assembly along with an engagement seam.
Figure 28:
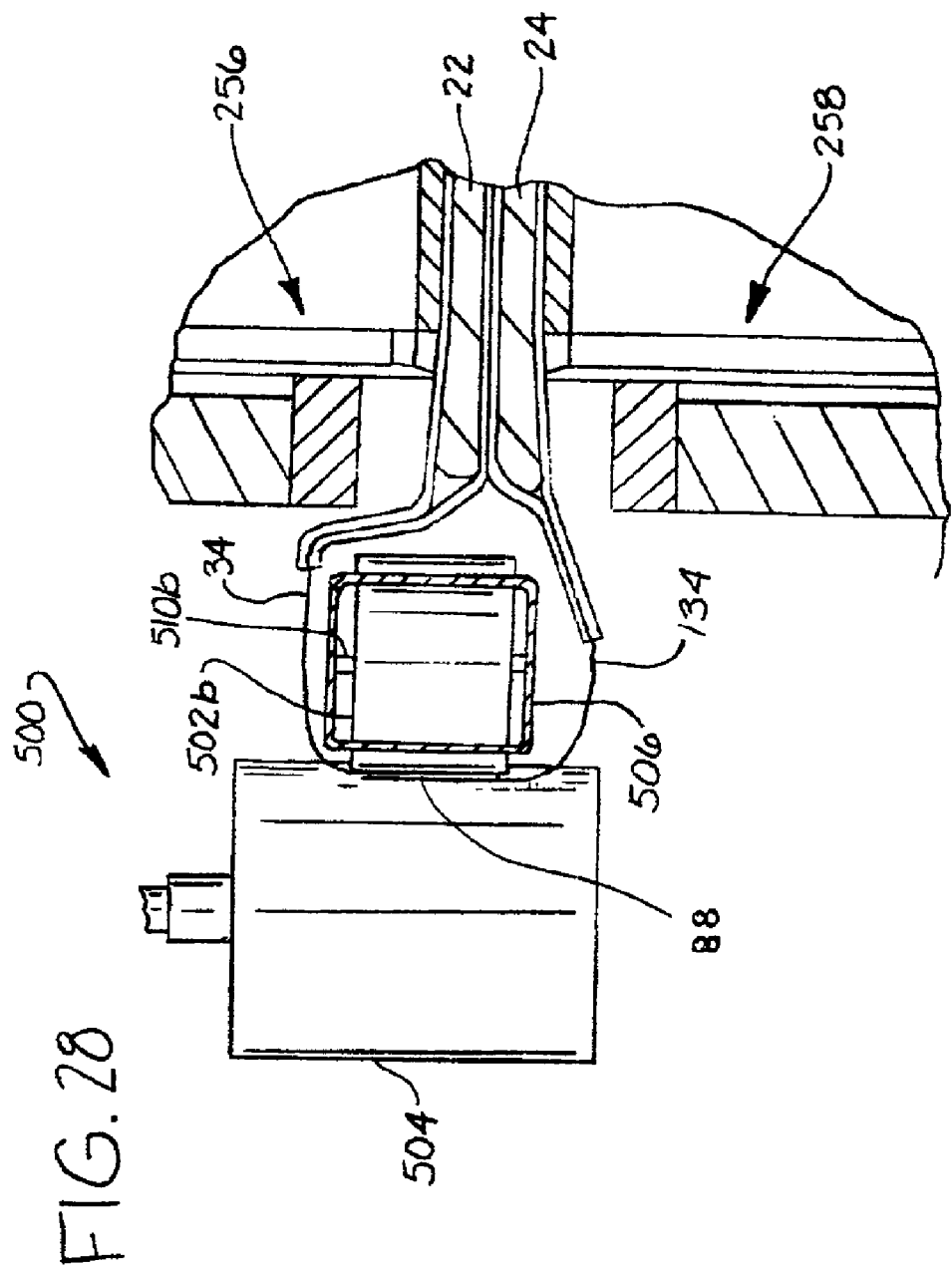
FIG. 28 is an enlarged section view of a portion of a pair of training pants passing through the nip assembly.

With particular reference to FIGS. 25 and 26, the non-driven rollers 502a, 502b are sized to extend radially outward from the mounting bracket 506 (e.g., transverse to the machine centerline) such that the face of each roller is disposed generally in the path along which the front and rear side panel fastening components 82, 84 are delivered to the nip assembly 500 as the pair of pants 102 is conveyed by the conveyors 256, 258 past the nip assembly. However, the dimensions (e.g., the diameter and the width) of each of the non-driven rollers 502a, 502b, as well as the dimensions of the mounting bracket 506, are preferably sufficiently small so that the rollers and mounting bracket do not interfere with the travel of the pants 102 past the nip assembly 500. More particularly, as shown in FIG. 28, the rollers 502a, 502b and mounting bracket 506 are sized such that the front and rear side panels 34, 134 extending laterally out from the absorbent chassis 32 pass respectively above and below the non-driven rollers and the mounting bracket, with the faces of the non-driven rollers disposed transversely inward from the engagement seam 88 formed by the fastening components 82, 84. As an example, the non-driven rollers 502a, 502b of the illustrated embodiment each have a diameter of about 0.75 inches and a face width of about 0.5 inches. The longitudinal (e.g., machine direction 108) spacing between the rotation axes defined by the axles 510a, 510b of the non-driven rollers 502a, 502b is about 0.875 inches.

A motor support frame 512 (FIGS. 15, 24 and 27) is mounted on the frame structure 354 of the seaming section 250 and supports a motor 514 generally above the upper conveyor 256. A drive shaft 516 depends from the motor 514 in operative connection therewith. The driven roller 504 is mounted on the drive shaft for conjoint driven rotation on a rotation axis defined by the drive shaft. As best seen in FIGS. 25 and 26, the rotation axis of the driven roller 504 is spaced generally transverse from the rotation axes of the non-driven rollers 502*a*, 502*b* relative to the machine direction 108 generally in the path along which the fastening components 82, 84 are delivered to the nip assembly 500. The rotation axis of the driven roller 504 is also disposed generally centrally between the rotation axes of the non-driven rollers 502*a*, 502*b* in the machine direction 108. The driven roller 504 has a diameter sized so that the roller is in close, generally transversely spaced relationship with both non-driven rollers 502*a*, 502*b* whereby the face of the driven roller and the face of the upstream non-driven roller together define an upstream nip 520*a* of the nip assembly 500 and the driven roller and downstream non-driven roller together define a downstream nip 520*b* of the nip assembly.

In the illustrated embodiment, the driven roller 504 is transversely positioned relative to the machine centerline such that the face of the driven roller is generally interposed between the faces of the non-driven rollers 502*a*, 502*b*. As such, the upstream and downstream nips 520*a*, 520*b* of the nip assembly 500 are skewed relative to the machine centerline, and more particularly relative to the machine direction in which the fastening components 82, 84 are delivered to the nip assembly. As used herein in reference to the nips 520*a*, 520*b*, the skew of each nip is defined by an angle ∝ (FIG. 25) formed between the machine centerline (e.g., also the machine direction 108 in the illustrated embodiment) and a line extending perpendicular to a line which extends between the rotation axis of the driven roller 504 and the rotation axis of the respective non-driven roller 502*a*, 502*b*. As an example, the driven roller 504 may have a diameter of about three inches and a face width of about 0.75 inches. The nips 520*a*, 520*b* formed between the driven roller 504 and the non-driven rollers 502*a*, 502*b* are preferably smaller than the thickness of the engagement seam 88 formed by the fastening components 82, 84. For example, the nips 520*a*, 520*b* may have widths in the range of about 0.01 inches to about 0.0625 inches. The nips 520*a*, 520*b* may be skewed relative to the machine direction 108 at an angle ∝ in the range of about 1° to about 90°, more desirably in the range of about 1° to about 30°, and still more desirably in the range of about 1° to about 15°.

It is understood that each of the rollers 502*a*, 502*b*, 504 of the illustrated nip assembly 500 may all be driven, either independently or by a common drive motor such as the motor 514, or they may all be non-driven. It is also contemplated that any one of the rollers 502*a*, 502*b*, 504, or a combination thereof, may be driven while the remaining rollers are non-driven. Moreover, one of the non-driven rollers 502*a*, 502*b* may be omitted altogether, and the rotation axis of the driven roller 504 may be offset from the rotation axis of the remaining non-driven roller relative to the machine direction 108, and remain within the scope of this invention.

Also, as shown in FIG. 25, the non-driven rollers 502*a*, 502*b* are of equal diameter and have rotation axes aligned in spaced relationship with each other in the machine direction 108, and the driven roller 504 is centrally positioned between the non-driven rollers in the machine direction so that the upstream and downstream nips 520*a*, 520*b* are of substantially equal size. However, the relative sizes of the nips 520*a*, 520*b* may vary, such as by sizing the downstream nip smaller than the upstream nip, without departing from the scope of this invention. For example, the rotation axis of the driven roller 504 may be disposed other than centrally between the rotation axes of the non-driven rollers 502*a*, 502*b* in the machine direction 108, i.e., longitudinally closer to one non-driven roller than the other. Alternatively, or additionally, the non-driven rollers 502*a*, 502*b* may be of different diameters, or the rotational axes of the non-driven rollers may be offset transversely from each other relative to the machine direction, so that one non-driven roller extends transversely into more closely spaced relationship with the driven roller 504 than the other non-driven roller. Not only would this result in different sized nips 520*a*, 520*b*, but the skew of the nips may also vary, e.g., the skew of the downstream nip may be other than the negative of that of the upstream nip.

The driven roller 504 and non-driven rollers 502*a*, 502*b* of the illustrated embodiment are each constructed of steel. However, it is understood that the rollers 504, 502*a*, 502*b* may be constructed from other metals, plastic, rubber or other suitable materials without departing from the scope of this invention. It is also contemplated that the driven roller 504 may be constructed of a magnetically attracting material while the non-driven rollers 502*a*, 502*b* are constructed of steel or other suitable metal attracted to the magnetically attracting material of the driven roller. In such an embodiment, the drive shaft 516 of the driven roller 504 may be flexible, or the non-driven rollers 502*a*, 502*b* may be mounted for movement generally transverse to the machine direction 108, such that magnetic attraction between the driven and non-driven rollers pulls the rollers toward each other to apply additional squeezing force to the fastening components 82, 84 when passing through the nips 520*a*, 520*b*.

The motor 514 drives rotation of the driven roller 504 in a direction such that the face of the driven roller passes tangentially through the nips 520*a*, 520*b* in a generally downstream direction, e.g., clockwise in FIG. 25. The motor 514 is desirably a variable speed motor to permit selective adjustment of the rotational velocity of the driven roller 504 depending on the speed at which the pair of pants 102 is transported in the machine direction 108 past the nip assembly 500, i.e., the speed at which the fastening components 82, 84 are delivered in the machine direction to the upstream nip 520*a* of the nip assembly. As an example, the upper and lower conveyors 256, 258 may transport the pants 102 past the nip assembly 500 at a speed in the range of about 100 ft./min. to about 1000 ft./min. The rotational velocity of the driven roller 504 is such that the tangential velocity of the face of the driven roller as it passes through the nips 520*a*, 520*b* is preferably at least about equal to and is more preferably greater than the speed at which the pair of pants 102 is conveyed in the machine direction 108 past the nip assembly 500. More particularly, the tangential velocity of the face of the driven roller 504 at each nip 520*a*, 520*b* is preferably in the range of about 0.01 percent to about five percent greater than the speed at which the pair of pants 102 is conveyed past the nip assembly 500, and more preferably in the range of about one percent to about three percent greater.

In operation, following engagement of the front and rear side panel fastening components 82, 84 as shown in FIG. 19 to form the engagement seam 88, the pair of pants 102 is transported by the conveyors 256, 258 in the machine direction 108 downstream to the nip assembly 500 so that the engagement seam is received by the nip assembly in a generally upright orientation (FIG. 28). Since the tangential velocity of the driven roller 504 is greater than the speed at which the pants 102, and more particularly the fastening components 82, 84, are delivered to the nip assembly 500, the fastening components are drawn (e.g., pulled) by the driven roller generally along the engagement seam 88 into the upstream nip 520a. Drawing or pulling on the fastening components 82, 84 in this manner pulls the fastening components taut along the engagement seam 88 to maintain engagement between the fastening components when entering the upstream nip 520a. If the tangential velocity of the driven roller 504 at the upstream nip 520a is too slow, such as below the speed at which the pair of pants 102 is delivered to the nip assembly 500, the fastening components 82, 84 tend to bunch slightly as they enter the nip. This increases the risk that the fastening components 82, 84 will partially or wholly separate and become misaligned along the engagement seam 88 when the fastening components enter the upstream nip 520a.

As the fastening components 82, 84 are drawn through the upstream nip 520a (FIG. 26), the driven roller 504 and the upstream non-driven roller 502a together apply a compression, or squeezing force, thereby urging the fastening components together to promote increased engagement between the fastening components along the engagement seam 88. The skew of the upstream nip 520a relative to the machine direction 108 causes the fastening components 82, 84 to flex (e.g., bend or fold) along the engagement seam 88 as they pass through the nip. This flexing of the fastening components 82, 84 at the engagement seam 88 tends to urge the fastening components to slide, or shift relative to each other at the engagement seam, thus generating a shear stress at the engagement seam which promotes increased engagement between the fastening components.

For example, where the fastening components 82, 84 are hook and loop fasteners, generating a shear stress at the engagement seam 88 urges sliding movement of one fastening component relative to the other such that the hooks become further embedded or otherwise entangled in the loops, thereby strengthening the engagement between the fastening components. Where the base material of the loop fastener is constructed of an elastic material, the applied shear stress may alternatively, or may additionally, result in stretching (which is also broadly considered herein as a sliding movement) of the loop fastener relative to the hook fastener, thereby increasing the spacing between the loops to allow the hooks to embed deeper therein.

Still referring to FIG. 26, the fastening components 82, 84 are then drawn by the driven roller 504 through the downstream nip 520b between the driven roller 504 and the downstream non-driven roller 502b. As with the upstream nip 502a, the driven roller 504 and downstream non-driven roller 502b together apply a compression or squeezing force to the fastening components along the engagement seam 88, thereby urging the fastening components together to promote increased engagement therebetween. The skew of the downstream nip 520b relative to the machine centerline also causes the fastening components 82, 84 to flex (e.g., bend or fold) at the engagement seam 88 as they pass through the nip to thereby further promote increased engagement between the fastening components.

It is understood herein that the rotational velocity of the driven roller 504 need not be such that the tangential velocity of the face of the driven roller as it passes through the nips 520a, 520b is equal to or greater than the speed at which the pair of pants 102 is conveyed past the nip assembly 500 to remain within the scope of this invention. Rather, flexing of the fastening components 82, 84 at the engagement seam 88 to generate a shear stress at the seam is advantageous independent of whether a driven roller 504 is provided. It is also understood that the fastening components 82, 84 need not be flexed at the engagement seam 88 upon passing through the nips 520a, 520b to derive advantages associated with driving the rotational velocity of the driven roller 504 such that the tangential velocity of the face of the driven roller as it passes through the nips is equal to or greater than the speed at which the pair of pants 102 is conveyed past the nip assembly 500.

Also, the nip assembly 500 shown and described herein more broadly defines a flexing assembly for flexing the fastening components 82, 84 at the engagement seam 88. However, it is contemplated that the flexing assembly need not comprise a nip assembly 500 or other device for squeezing the fastening components together at the engagement seam as the fastening components are flexed. For example, the flexing assembly may comprise a single roller, such as rollers 502a, 502b, 504 or other structural member (not shown) over which the fastening components 82, 84 pass as the pair of pants 102 is conveyed past the flexing assembly. Such a roller 502a, 502b, 504 or other structure may be positioned sufficiently outward from the machine centerline so that the fastening components 82, 84 at the engagement seam 88 are flexed (e.g., bent or folded) around a portion of the face or laterally outermost extent of such a roller or other structure to generate a shear stress at the engagement seam.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

When introducing elements of the present invention or the preferred embodiment(s) thereof, the articles a, an, the and said are intended to mean that there are one or more of the elements. The terms comprising, including and having are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A method for securing engagement between fastening components of a pre-fastened garment upon initial assembly thereof, the fastening components being capable of fastening engagement with each other, the method comprising the steps of:
    arranging the fastening components in at least partially opposed relationship with each other;
    engaging the fastening components with each other to define an engagement seam; and
    flexing the fastening components at the engagement seam whereby said flexing generates a shear stress at the engagement seam to promote increased engagement between the fastening components.

2. A method as set forth in claim 1 wherein flexing of the fastening components at the engagement seam causes at least one of sliding movement of one of said fastening components relative to the other one of said fastening components and stretching of at least one of said fastening components.

3. A method as set forth in claim 1 further comprising urging the fastening components generally toward each other while flexing the garment at the engagement seam.

4. A method as set forth in claim 1 wherein the fastening components are releasable from and re-engageable with each other.

5. A method as set forth in claim 4 wherein the fastening components are hook and loop fasteners.

6. A method as set forth in claim 1 wherein the step of flexing the fastening components at the engagement seam comprises delivering the fastening components in a predetermined direction to a flexing assembly whereby the flexing assembly flexes the fastening components at the engagement seam in a direction other than said predetermined direction to generate a shear stress at the engagement seam.

7. A method as set forth in claim 6 wherein the flexing assembly comprises a nip assembly through which the fastening components pass in a direction generally other than in the predetermined direction in which the fastening components are delivered to the nip assembly such that the fastening components generally flex at the engagement seam upon passing through the nip assembly.

8. A method as set forth in claim 1 wherein the step of flexing the fastening components at the engagement seam comprises:
delivering the fastening components in a predetermined direction to a nip; and
passing the fastening components through the nip generally at the engagement seam to urge the fastening components toward each other, the nip being skewed relative to said predetermined direction such that the fastening components generally flex at the engagement seam as the fastening components pass through the nip.

9. A method as set forth in claim 1 wherein the prefastened garment comprises an absorbent chassis having a front waist region, a back waist region and a crotch region extending longitudinally therebetween, a front side panel extending laterally out from the front waist region, a back side panel extending laterally out from the back waist region, one of the fastening components being disposed on the front side panel and the other one of the fastening components being disposed on the back side panel, said arranging step comprising arranging the front and back aide panels relative to each other such that the respective fastening components thereof are in at least partially opposed relationship with each other.

10. A method as set forth in claim 9 wherein the step of arranging the front and back side panels relative to each other comprises folding the absorbent chassis at the crotch region such that the front and back waist regions are in generally opposed relationship with each other and the front and back side panels are in at least partially opposed relationship with each other.

11. A method as set forth in claim 1 wherein the step of flexing the fastening components at the engagement seam comprises delivering the fastening components in a predetermined direction to a nip assembly through which the fastening components pass in a direction generally other than in the predetermined direction in which the fastening components are delivered to the nip assembly such that the fastening components generally flex at the engagement seam upon passing through the nip assembly.

12. A method for securing engagement between fastening components of a pre-fastened garment upon initial assembly thereof, the fastening components being capable of fastening engagement with each other, the method comprising the steps of:
arranging the fastening components in at least partially opposed relationship with each other;
engaging the fastening components with each other to define an engagement seam;
delivering the fastening components in a predetermined direction to a nip;
passing the fastening components through the nip generally at the engagement seam to urge the fastening components toward each other; and
flexing the fastening components at the engagement seam whereby said flexing generates a shear stress at the engagement seam as the fastening components pass through the nip to promote increased engagement between the fastening components, the nip being skewed relative to said predetermined direction such that the fastening components generally flex at the engagement seam, the nip being defined by a pair of rollers disposed in generally transverse, closely spaced relationship with each other relative to the predetermined direction in which the fastening components are delivered to the nip, each roller being rotatable on a rotation axis, said rotation axes of the rollers being generally spaced from each other in said predetermined direction such that the nip formed by the rollers is skewed relative to said predetermined direction.

13. A method as set forth in claim 12 further comprising driving rotation of at least one of the rollers such that the tangential velocity of said at least one roller at the nip is at least about equal to the speed at which the fastening components are delivered to the nap.

14. A method as set forth in claim 13 wherein the tangential velocity of said at least one roller at the nip as greater than the speed at which the fastening components ire delivered to the nip.

15. A method as set forth in claim 14 wherein the tangential velocity of said at least one roller at the nip is in the range of about 0.01 percent to about five percent greater than the speed at which the fastening components are delivered to the nip.

16. A method as set forth in claim 15 wherein the tangential velocity of said at least one roller at the nip is in the range of about one percent to about three percent greater than the speed at which the fastening components are delivered to the nip.

17. A method for securing engagement between fastening components of a pre-fastened garment upon initial assembly thereof, the fastening components being capable of fastening engagement with each other, the method comprising the steps of:
arranging the fastening components in at least partially opposed relationship with each other;
engaging the fastening components with each other to define an engagement seam;
delivering the fastening components in a predetermined direction to a first nip;
passing the fastening components through the first nip generally at the engagement seam to urge the fastening components toward each other;

flexing the fastening components at the engagement seam whereby said flexing generates a shear stress at the engagement seam to promote increased engagement between the fastening components as the fastening components pass through the first; nip, the first nip being skewed relative to said predetermined direction such that the fastening components generally flex at the engagement seam; and passing the fastening components through a second nip after passing said fastening components through the first nip, the second nip being skewed relative to the predetermined direction in which the fastening components are delivered to the first nip.

18. A method as set forth in claim 17 wherein the second nip is skewed relative to the first nip.

19. A method for securing engagement between fastening components of a pre-fastened garment upon initial assembly thereof, the fastening components being capable of fastening engagement with each other, the method comprising the steps of:

arranging the fastening components in at least partially opposed relationship with each other;

engaging the fastening components with each other to define an engagement seam;

delivering the fastening components in a predetermined direction to a first nip;

passing the fastening components through the first nip generally at the engagement seam to urge the fastening components toward each other;

flexing the fastening components at the engagement seam whereby said flexing generates a shear stress at the engagement seam to promote increased engagement between the fastening components as the fastening components pass through the first nip, the first nip being skewed relative to said predetermined direction such that the fastening components generally flex at the engagement seam; and passing the fastening components through a second nip after passing said fastening components through the first nip, the second nip being skewed relative to the skew of the first nip such that the fastening components are flexed at the engagement seam while passing through the second nip.

20. A method as set forth in claim 19 wherein the skew of the second nip is substantially the opposite of the skew of the first nip.

21. A method as set forth in claim 19 further comprising passing the fastening components through the second nip generally at a downstream portion of the engagement seam while concurrently passing the fastening components through the first nip generally at an upstream portion of the engagement seam.

22. A method for securing engagement between fastening components of a pro-fastened garment upon initial assembly thereof, the fastening components being capable of fastening engagement with each other, the method comprising the steps of:

arranging the fastening components in at least partially opposed relationship with each other;

engaging the fastening components with each other to define an engagement seam; and mechanically handling the garment to generate a shear stress along the engagement seam to promote increased engagement between the fastening components.

23. A method as set forth in claim 22 wherein the shear stress is generated by urging sliding movement of one fastening component relative to the other fastening component.

24. A method as set forth in claim 23 wherein said sliding movement comprises at least one of sliding movement and stretching of said one fastening component relative to the other fastening component.

25. A method as set forth in claim 23 wherein said step of urging sliding movement comprises flexing the fastening components at the engagement seam.

26. A method as set forth in claim 22 further comprising urging the fastening components toward each other while generating the shear stress along the engagement seam.

27. A method as set forth in claim 22 wherein the pre-fastened garment comprises an absorbent chassis having a front waist region, a back waist region and a crotch region extending longitudinally therebetween, a front side panel extending laterally out from the front waist region, a back side panel extending laterally out from the back waist region, one of the fastening components being disposed on the front side panel and the other one of the fastening components being disposed on the back side panel, said arranging step comprising arranging the front and back side panels relative to each other such that the respective fastening components thereof are in at least partially opposed relationship with each other.

28. A method as set forth in claim 27 wherein the step of arranging the front and back side panels relative to each other comprises folding the absorbent chassis at the crotch region such that the front and back waist regions are in generally opposed relationship with each other and the front and back side panels are in at least partially opposed relationship with each other.

29. A method for securing engagement between fastening components of a pre-fastened garment, the fastening components being generally flexible and capable of fastening engagement with each other, the method comprising the steps of:

aligning the fastening components in at least partially opposed relationship with each other;

engaging the fastening components with each other to define an engagement seam;

delivering the fastening components at said engagement seam to a nip;

drawing the fastening components into the nip at said engagement seam at a speed greater than the speed at which the fastening components are delivered to the nip; and passing the fastening components through the nip generally at said engagement seam to urge the fastening components together for promoting increased engagement between the fastening components.

30. A method as set forth in claim 29 wherein the nip is defined by at least one driven roller, said step of drawing the fastening components into said nip at said engagement seam comprising driving rotation of said at least one driven roller such that the tangential velocity of said at least one roller at the nip is greater than the speed at which the fastening components are delivered to the nip.

31. A method for securing engagement between fastening components of a pre-fastened garment, the fastening components being generally flexible and capable of fastening engagement with each other, the method comprising the steps of:

aligning the fastening components in at least partially opposed relationship with each other;

engaging the fastening components with each other to define an engagement seam;

delivering the fastening components at said engagement seam to a nip, the nip being defined by at least one driven roller;

drawing the fastening components into the nip at said engagement seam by driving rotation of said at least one driven roller such that the tangential velocity of said at least one roller at the nip is in the range of about 0.01 percent to about five percent greater than the speed at which the fastening components are delivered to the nip; and passing the fastening components through the nip generally at said engagement seam to urge the fastening components together for promoting increased engagement between the fastening components.

32. A method as set forth in claim 31 wherein the tangential velocity of said at least one roller at the nip is in the range of about one percent to about three percent greater than the speed at which the fastening components are delivered to the nip.

33. Apparatus for making a pre-fastened garment of the type comprising an absorbent chassis having a front waist region, a back waist region and a crotch region extending longitudinally therebetween, a front side panel extending laterally out from the front waist region and a back side panel extending laterally out from the back waist region, the front side panel having a fastening component adapted for fastening engagement with a corresponding fastening component of the back side panel, the pre-fastened garment being conveyed in a machine direction through the apparatus, said apparatus comprising:

an assembly section adapted to at least partially assemble the garment such that the garment exits the assembly section with the fastening components of the front and back side panels generally disconnected from each other;

a seaming section adapted to orient the front and back side panels relative to each other such that the fastening components are in at least partially opposed relationship with each other, and to engage the fastening components together to form an engagement seam of the garment; and a flexing assembly for generally flexing the fastening components at the engagement seam to generate a shear stress at said engagement seam to thereby promote increased engagement between the fastening components.

34. Apparatus as set forth in claim 33 further comprising a folding section intermediate the assembly section and the seaming section, said folding section being adapted to fold the garment generally at the crotch region thereof such that the front and rear waist regions of the absorbent chassis are generally in opposed relationship with each other and the front side panel is in at least partially opposed relationship with the back side panel.

35. Apparatus as set forth in claim 33 wherein the flexing assembly is adapted to convey the fastening components at the engagement seam through a generally tortuous path relative to the machine direction in which the garment is delivered to said flexing assembly.

36. Apparatus as set forth in claim 33 wherein the flexing assembly comprises a nip assembly adapted for receiving the fastening components generally at the engagement seam, said nip assembly comprising a nip through which the fastening components are passed whereby the fastening components are urged toward each other while passing through the nip, said nip assembly being configured to generally flex the fastening components at the engagement seam as the fastening components pass through the nip.

37. Apparatus for making a pre-fastened garment of the type comprising an absorbent chassis having a front waist region, a back waist region and a crotch region extending longitudinally therebetween, a front side panel extending laterally out from the front waist region and a back side panel extending laterally out from the back waist region, the front side panel having a fastening component adapted for fastening engagement with a corresponding fastening component of the back side panel, the pre-fastened garment being conveyed in a machine direction through the apparatus, said apparatus comprising:

an assembly section adapted to at least partially assemble the garment such that the garment exits the assembly section with the fastening components of the front and back side panels generally disconnected from each other;

a seaming section adapted to orient the front and back side panels relative to each other such that the fastening components are in at least partially opposed relationship with each other, and to engage the fastening components together to form an engagement seam of the garment, and a flexing assembly for generally flexing the fastening components at the engagement seam to generate a shear stress at said engagement seam to thereby promote increased engagement between the fastening components, the flexing assembly comprising a nip assembly adapted for receiving the fastening components generally at the engagement seam, said nip assembly comprising a nip through which the fastening components are passed whereby the fastening components are urged toward each other while passing through the nip, said nip assembly being configured to generally flex the fastening components at the engagement seam as the fastening components pass through the nip, the nip being skewed relative to the machine direction in which the fastening components are delivered to the nip.

38. Apparatus as set forth in claim 37 wherein the nip assembly comprises first and second rollers disposed in generally transverse, closely spaced relationship with each other to define the nip therebetween, each roller being rotatable on a rotation axis, the rotation axes of the rollers being generally spaced from each other in the machine direction such that the nip formed by the rollers is skewed relative to said machine direction.

39. Apparatus as set forth in claim 38 wherein at least one of the rollers is operatively connected to a motor for driven rotation thereof such that the tangential velocity of said at least one roller at the nip is at least about equal to the speed at which the garment is conveyed in the machine direction past the nip assembly.

40. Apparatus as set forth in claim 39 wherein the tangential velocity of said at least one roller at the nip is greater than the speed at which the garment is conveyed past the nip assembly.

41. Apparatus as set forth in claim 40 wherein the tangential velocity of said at least one roller at the nip is in the range of about 0.01 percent to about five percent greater than the speed at which the garment is conveyed past the nip assembly.

42. Apparatus as set forth in claim 41 wherein the tangential velocity of said at least one roller at the nip is in the range of about one percent to about three percent greater than the speed at which the garment is conveyed past the nip assembly.

43. A nip assembly for securing engagement between fastening components of a pre-fastened garment, the fastening components each being flexible and engaged with each other generally along an engagement seam to at least partially form said pre-fastened garment, the nip assembly being oriented for receiving the fastening components generally in a predetermined direction, said nip assembly comprising:

a first roller rotatable on a first rotation axis and a second roller rotatable on a second rotation axis, said second roller being in generally closely spaced relationship with the first roller transverse to the predetermined direction to define a nip therebetween through which the fastening components pass following receipt of the fastening components into the nip assembly such that the rollers urge the fastening components together generally at the engagement seam, the second rotation axis being spaced downstream from the first rotation axis in the predetermined direction such that the nip between the first and second rollers is skewed relative to the predetermined direction in which the fastening components are received by the nip at an angle in the range of about 1° to about 90°.

44. A nip assembly as set forth in claim 43 wherein the nip between the first and second rollers is skewed relative to the predetermined direction at an angle in the range of about 1° to about 30.

45. A nip assembly for securing engagement between fastening components of a pre-fastened garment, the fastening components each being flexible and engaged with each other generally along an engagement seam to at least partially form said pre-fastened garment, the nip assembly being oriented for receiving the fastening components generally in a predetermined direction, said nip assembly comprising:
a first roller rotatable on a first rotation axis;
a second roller rotatable on a second rotation axis, said second roller being in generally closely spaced relationship with the first roller transverse to the predetermined direction to define a first nip therebetween through which the fastening components pass following receipt of the fastening components into the first nip assembly such that the rollers urge the fastening components together generally at the engagement seam, the second rotation axis being spaced downstream from the first rotation axis in the predetermined direction such that the first nip between said first and second rollers is generally skewed relative to said predetermined direction; and
a third roller rotatable on a third rotation axis, said third roller being in generally closely spaced relationship with the second roller transverse to the predetermined direction to define a second nip therebetween through which the fastening components are passed generally at the engagement seam following passage of the fastening components through the first nip.

46. A nip assembly as set forth in claim 45 wherein the second roller is operatively connected to a motor for driven rotation thereof.

47. A nip assembly as set forth in claim 46 wherein the skew of the second nip is substantially the opposite of the skew of the first nip.

48. A nip assembly as set forth in claim 45 wherein the second nip is generally skewed relative to said predetermined direction in which the fastening components are received by the nip assembly.

49. A nip assembly for securing engagement between fastening components of a pre-fastened garment, the fastening components each being flexible and engaged with each other generally along an engagement seam to at least partially form said pre-fastened garment, the nip assembly being oriented for receiving the fastening components generally in a predetermined direction, said nip assembly comprising:
a first roller rotatable on a first rotation axis and a second roller rotatable on a second rotation axis, said second roller being in generally closely spaced relationship with the first roller transverse to the predetermined direction to define a nip therebetween through which the fastening components pass following receipt of the fastening components into the nip assembly such that the rollers urge the fastening components together generally at the engagement seam, the second rotation axis being spaced downstream from the first rotation axis in the predetermined direction such that the nip between said first and second rollers is generally skewed relative to said predetermined direction, one of the first arid second rollers being constructed of a magnetically attractive material and the other one of the first and second rollers being constructed of a metal attracted to said magnetically attractive material.

50. A nip assembly as set forth in claim 49 wherein the second nip is generally skewed relative to the skew of the first nip.

51. A method for securing engagement between fastening components of a pre-fastened garment upon initial assembly thereof, the fastening components being capable of fastening engagement with each other, the method comprising the steps of:
arranging the fastening components in at least partially opposed relationship with each other;
engaging the fastening components with each other to define an engagement seam;
delivering the fastening components in a predetermined direction to a nip;
passing the fastening components through the nip generally at the engagement seam to urge the fastening components toward each other; and
flexing the fastening components at the engagement seam as the fastening components pass through the nip whereby said flexing generates a shear stress at the engagement seam to promote increased engagement between the fastening components as the fastening components pass through the nip, the nip being skewed relative to said predetermined direction at an angle in the range of about 1 degree to about 30 degrees such that the fastening components generally flex at the engagement seam.

52. A method for securing engagement between fastening components of a pre-fastened garment upon initial assembly thereof, the fastening components being capable of fastening engagement with each other and having longitudinal direction in which the components are moved during engagement, and a transverse direction, the method comprising:
arranging the fastening components in at least partially opposed relationship with each other;
engaging the fastening components with each other to define an engagement seam; and
flexing the fastening components at the engagement seam whereby said flexing generates a shear stress at the engagement seam in said longitudinal direction of the fastening components to promote increased engagement between the fastening components.

53. A method as set forth in claim 52 wherein the fastening components of the pre-fastened garment have a longitudinal axis and a lateral axis, and wherein said step of flexing the fastening components flexes the fastening components generally laterally at the engagement seams.

* * * * *